United States Patent
Kashiwagi et al.

(10) Patent No.: US 12,383,157 B2
(45) Date of Patent: Aug. 12, 2025

(54) BRAIN FUNCTIONAL CONNECTIVITY CORRELATION VALUE CLUSTERING DEVICE, BRAIN FUNCTIONAL CONNECTIVITY CORRELATION VALUE CLUSTERING SYSTEM, BRAIN FUNCTIONAL CONNECTIVITY CORRELATION VALUE CLUSTERING METHOD, BRAIN FUNCTIONAL CONNECTIVITY CORRELATION VALUE CLASSIFIER PROGRAM, BRAIN ACTIVITY MARKER CLASSIFICATION SYSTEM AND CLUSTERING CLASSIFIER MODEL FOR BRAIN FUNCTIONAL CONNECTIVITY CORRELATION VALUES

(71) Applicant: ADVANCED TELECOMMUNICATIONS RESEARCH INSTITUTE INTERNATIONAL, Kyoto (JP)

(72) Inventors: Yuuto Kashiwagi, Soraku-gun (JP); Tomoki Tokuda, Soraku-gun (JP); Yuji Takahara, Soraku-gun (JP); Mitsuo Kawato, Soraku-gun (JP); Ayumu Yamashita, Soraku-gun (JP); Okito Yamashita, Soraku-gun (JP); Yuki Sakai, Soraku-gun (JP); Junichiro Yoshimoto, Soraku-gun (JP)

(73) Assignee: ADVANCED TELECOMMUNICATIONS RESEARCH INSTITUTE INTERNATIONAL, Kyoto (JP)

( * ) Notice: Subject to any disclaimer, the term of this patent is extended or adjusted under 35 U.S.C. 154(b) by 458 days.

(21) Appl. No.: 17/914,398

(22) PCT Filed: Apr. 2, 2021

(86) PCT No.: PCT/JP2021/014254
§ 371 (c)(1),
(2) Date: Sep. 26, 2022

(87) PCT Pub. No.: WO2021/205996
PCT Pub. Date: Oct. 14, 2021

(65) Prior Publication Data
US 2023/0107263 A1 Apr. 6, 2023

(30) Foreign Application Priority Data

Apr. 6, 2020 (JP) .................. 2020-068669

(51) Int. Cl.
*A61B 5/055* (2006.01)
*A61B 5/16* (2006.01)
(Continued)

(52) U.S. Cl.
CPC .............. *A61B 5/055* (2013.01); *A61B 5/165* (2013.01); *G06F 18/211* (2023.01); *G06F 18/2415* (2023.01); *G06F 2123/02* (2023.01)

(58) Field of Classification Search
CPC ....... A61B 5/055; A61B 5/165; A61B 5/0042; A61B 5/7267; G06F 18/211;
(Continued)

(56) References Cited

U.S. PATENT DOCUMENTS

| 11,666,219 B2 | 6/2023 | Fox |
| 2007/0055118 A1 | 3/2007 | Kawasaki et al. |

(Continued)

FOREIGN PATENT DOCUMENTS

| CN | 106407733 A | 2/2017 |
| JP | 2015-62817 A | 4/2015 |

(Continued)

OTHER PUBLICATIONS

"Distance correlation", Wikipedia, retrieved on Jun. 21, 2022, https://en.wikipedia.org/wiki/Distance_correlation.
(Continued)

*Primary Examiner* — Charlotte M Baker
(74) *Attorney, Agent, or Firm* — Birch, Stewart, Kolasch & Birch, LLP

(57) ABSTRACT

A brain functional connectivity correlation value clustering device for clustering subjects having a prescribed attribute on the basis of brain measurement data obtained from a plurality of facilities, wherein a plurality of MRI devices capture resting state fMRI image data of a healthy cohort and a patient cohort; a computing system 300 performs generation of an identifier as ensemble learning of "supervised learning" between harmonized component values of correlation matrixes and disease labels of each of the subjects, selects, during the ensemble learning, features for clustering in accordance with importance from the features
(Continued)

specified for generating an identifier for a disease label, and performs multiple co-clustering by "unsupervised learning."

19 Claims, 55 Drawing Sheets

(51) Int. Cl.
  *G06F 18/211*  (2023.01)
  *G06F 18/2415*  (2023.01)
  *G06F 123/02*  (2023.01)

(58) Field of Classification Search
  CPC ... G06F 18/2415; G06F 2123/02; G06N 7/01;
                       G06N 20/20
  USPC ........................................................ 382/128
  See application file for complete search history.

(56) References Cited

U.S. PATENT DOCUMENTS

| | | | |
|---|---|---|---|
| 2009/0124886 A1 | 5/2009 | Wang et al. | |
| 2013/0102918 A1 | 4/2013 | Elkin et al. | |
| 2013/0211229 A1 | 8/2013 | Rao et al. | |
| 2015/0160322 A1 | 6/2015 | Matthews | |
| 2015/0174362 A1 | 6/2015 | Panova et al. | |
| 2015/0272461 A1 | 10/2015 | Morimoto et al. | |
| 2017/0042474 A1 | 2/2017 | Widge et al. | |
| 2017/0071522 A1 | 3/2017 | Parsey et al. | |
| 2017/0340212 A1* | 11/2017 | Lin | G16H 30/40 |
| 2018/0098738 A1* | 4/2018 | Sutoko | A61B 5/4064 |
| 2019/0090749 A1 | 3/2019 | Leuthardt et al. | |
| 2019/0328782 A1* | 10/2019 | Braithwaite | A61K 35/16 |
| 2019/0374154 A1* | 12/2019 | Wendling | A61B 5/4082 |
| 2019/0392348 A1 | 12/2019 | Ando et al. | |
| 2020/0077947 A1* | 3/2020 | Shi | G06T 7/0014 |
| 2020/0163609 A1 | 5/2020 | Lisi et al. | |
| 2021/0015366 A1* | 1/2021 | Agrawal | G06T 11/008 |
| 2021/0034912 A1 | 2/2021 | Lisi et al. | |

FOREIGN PATENT DOCUMENTS

| | | |
|---|---|---|
| JP | 2015-112474 A | 6/2015 |
| JP | 2017-196523 A | 11/2017 |
| JP | 2018-89142 A | 6/2018 |
| JP | 2019-63478 A | 4/2019 |
| JP | 2019-198376 A | 11/2019 |
| JP | 2020-24139 A | 2/2020 |
| WO | WO 2005/025421 A1 | 3/2005 |
| WO | WO 2006/102370 A2 | 9/2006 |
| WO | WO 2007/014467 A1 | 2/2007 |
| WO | WO 2011/038124 A2 | 3/2011 |
| WO | WO 2016/203456 A1 | 12/2016 |
| WO | WO 2017/090590 A1 | 6/2017 |
| WO | WO 2017/162773 A1 | 9/2017 |
| WO | WO 2018/147193 A1 | 8/2018 |

OTHER PUBLICATIONS

Behzadi et al., "A component based noise correction method (CompCor) for BOLD and perfusion based fMRI", Neuroimage, 2007, 37(1), pp. 90-101.
Blei et al., "Variational inference for Dirichlet process mixtures", Bayesian analysis, 2006, 1(1), pp. 121-144.
Breiman, "Random Forests", Machine Learning, 2001, 45, pp. 5-32.
Dadi et al., "Benchmarking functional connectome-based predictive models for resting-state fMRI", Preprint submitted to NeuroImage, Jan. 14, 2019.
Dinga et al., "Evaluating the evidence for biotypes of depression: Methodological replication and extension of Drysdale et al. (2017)", NeuroImage: Clinical, 2019, 22, 101796, total 11 pages.
Drysdale et al., "Resting-state connectivity biomarkers define neurophysiological subtypes of depression", nature medicine, Jan. 2017, vol. 23, No. 1, total 16 pages.
Finn et al., "Functional connectome fingerprinting: identifying individuals based on patterns of brain connectivity", Nat Neurosci, 2015, 18(11), pp. 1664-1671.
Glasser et al., "A multi-modal parcellation of human cerebral cortex", Nature, 2016, 536(7615), pp. 171-178.
Glasser et al., "The Human Connectome Project's Neuroimaging Approach", Nat Neurosci., 2016, 19(9), pp. 1175-1187.
Guan et al., "Variational inference for nonparametric multiple clustering", In: MultiClust Workshop, KDD-2010, 2010.
International Search Report (PCT/ISA/210), issued in PCT/JP2021/014254, dated Jun. 15, 2021.
Japan Agency for Medical Research and Development, "AI-based Endoscopy Diagnostic Support Program Approved—To be Used to Assist Physicians in Diagnosis—", Press Release, Dec. 10, 2018, https://www.amed.go.jp/news/release_20181210.html.
Jensen, "Sur les fonctions convexes et les inégalités entre les valeurs moyennes", Acta Mathematica, 1905, 30(1), pp. 175-193.
Johnson et al., "Adjusting batch effects in microarray expression data using empirical Bayes methods" Biostatistics, 2007, 8, 1, pp. 118-127.
Kubo, "Data kaiseki no tameno toukei modeling nyu'mon" (Introduction to statistical modeling for data analysis), Iwanami shoten, 1st edition 2012, 14th edition, 2017.
Madeira et al., "Biclustering algorithms for biological data analysis: a survey", IEEE Transactions on Computational Biology and Bioinformatics, 2004, vol. 1, No. 1, pp. 24-45.
Murphy, "Machine Learning: A Probabilistic Perspective", Cambridge, Massachusetts: MIT Press, 2012.
Noble et al., "Multisite reliability of MR-based functional connectivity", Neuroimage, 2017, 146, pp. 959-970.
Pearlson, "Multisite collaborations and large databases in psychiatric neuroimaging advantages, problems, and challenges", Schizophr Bull, 2009, vol. 35, No. 1, pp. 1-2.
Perrot et al., "Cortical sulci recognition and spatial normalization", Medical Image Analysis, 2011, 15, pp. 529-550.
Rosenberg et al., "A neuromarker of sustained attention from whole-brain functional connectivity", Nat Neurosci, 2016, 19(1), pp. 165-171.
Santos et al., "On the Use of the Adjusted Rand Index as a Metric for Evaluating Supervised Classification", ICANN 2009, 2009, Part II, LNCS 5769, pp. 175-184.
Shen et al., "Groupwise whole-brain parcellation from resting-state fMRI data for network node identification", Neuroimage, 2013, 82, pp. 403-415.
Székely et al., "Measuring and testing dependence by correlation of distances", Ann. Statist., 2007, vol. 35, No. 6, pp. 2769-2794.
Tokuda et al., "Identification of depression subtypes and relevant brain regions using a data-driven approach", Scientific Reports, 2018, 8:14082, DOI:10.1038/s41598-018-32521-z, total 13 pages.
Tokuda et al., "Multiple co-clustering based on nonparametric mixture models with heterogeneous marginal distributions", PLOS One, Oct. 19, 2017, pp. 1-29.
Tzourio-Mazoyer et al., "Automated Anatomical Labeling of Activations in SPM Using a Macroscopic Anatomical Parcellation of the MNI MRI Single-Subject Brain", Neuroimage, 2002, 15, pp. 273-289.
Written Opinion of the International Searching Authority (PCT/ISA/237), issued in PCT/JP2021/014254 dated Jun. 15, 2021.
Yahata et al., "A small No. of abnormal brain connections predicts adult autism spectrum disorder", Nat Commun, 2016, 7, 11254.
Yamashita et al., "Harmonization of resting-state functional MRI data across multiple imaging sites via the separation of site differences into sampling bias and measurement bias", PLOS Biology, Apr. 18, 2019, pp. 1-34.
Yamashita et al., "Sparse Estimation automatically selects voxels relevant for the decoding of fMRI activity patterns" NeuroImage, 2008, 42(4), pp. 1414-1429.
U.S. Office Action for U.S. Appl. No. 16/753,291, dated Jul. 19, 2023.

(56) References Cited

OTHER PUBLICATIONS

Journal of International Psychiatry, vol. 42, No. 1, 2015, pp. 73-76.
"r—How to do classification after clustering?—Cross Validated," Feb. 28, 2017, XP093099851, retrieved from the Internet, URL: <https://stats.stackexchange.com/questions/264312/how-to-do-classification-after-clustering>.
Extended European Search Report for European Application No. 21842607.0, dated Nov. 22, 2023.
Yamada et al., "Resting-State Functional Connectivity-Based Biomarkers and Functional MRI-Based Neurofeedback for Psychiatric Disorders: A Challenge for Developing Theranostic Biomarkers," International Journal of Neuropsychopharmacology, vol. 20, No. 10, 2017, pp. 769-781.
Zeng et al., "Unsupervised Classification of Major Depression Using Functional Connectivity MRI," Human Brain Mapping, vol. 35, 2014, pp. 1630-1641.
Extended European Search Report for European Application No. 21785099.9, dated Apr. 3, 2024.

\* cited by examiner

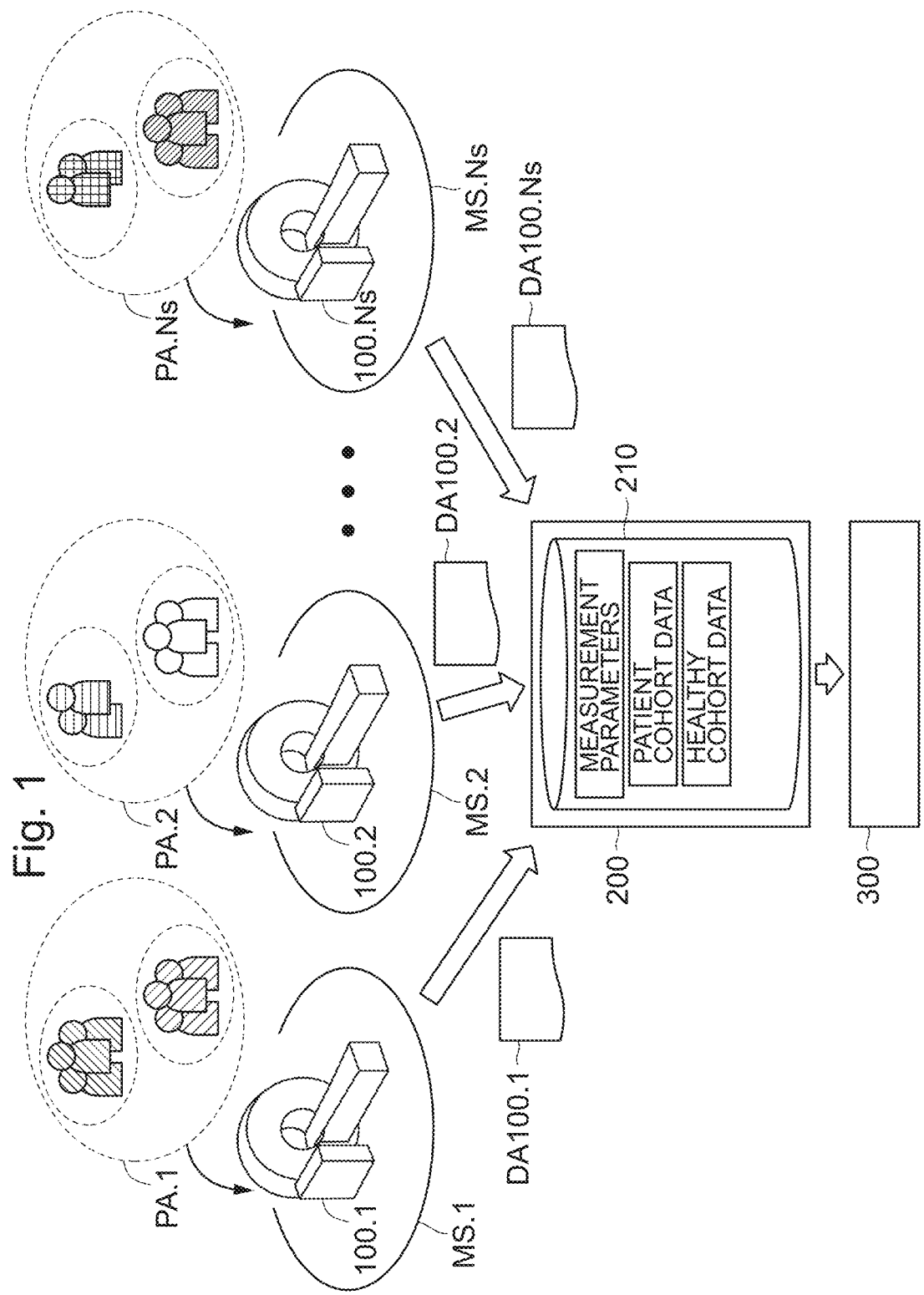

EXTRACTION OF AVERAGE WAVEFORM
IN EACH REGION OF INTEREST

CALCULATE CORRELATION MATRIX
BETWEEN Nc REGIONS

Fig. 3A

| SITE ID | | |
|---|---|---|
| SITE NAME | | |
| CONDITION ID | | |
| MEASURING DEVICE | MANUFACTURER NAME | |
| | MODEL No. | |
| | NUMBER OF RECEIVING COILS | |
| | ... | |
| MEASUREMENT CONDITIONS | DIRECTION OF PHASE ENCODING (P→A,A→P) | |
| | IMAGE TYPE | |
| | IMAGING SEQUENCE | |
| | EYES OPEN/CLOSED | |
| | ... | |

Fig. 3B

| SUBJECT ANONYMIZED ID | | |
|---|---|---|
| CONDITION ID | | |
| SEX | | |
| AGE | | |
| HEALTHY/DISEASE | | |
| DIAGNOSED DISEASE NAME | | |
| MEDICATION PROFILE | (RELATIVE DATE) | MEDICATION 1 |
| | (RELATIVE DATE) | MEDICATION 2 |
| | ... | ... |
| DIAGNOSIS HISTORY | (RELATIVE DATE) | DIAGNOSIS |
| | (RELATIVE DATE) | DIAGNOSIS |
| | ... | ... |

Fig. 10

| DEMOGRAPHIC CHARACTERISTICS OF PATIENTS INCLUDED IN TRAINING DATASET |||||||||||
|---|---|---|---|---|---|---|---|---|---|---|
| SITE | HEALTHY CONTROLS (HCS) ||| MDD PATIENTS (MDDS) ||| SUM ||||
| | NUMBER OF PARTICIPANTS | MALE/FEMALE | AGE | BDI | NUMBER OF PARTICIPANTS | MALE/FEMALE | AGE | BDI | NUMBER OF PARTICIPANTS | MALE/FEMALE | AGE | BDI |
| SITE 1 (COI) | 124 (123) | 46/78 | 51.9± 13.4 | 8.2± 6.3 | 70 (70) | 31/39 | 45.0± 12.5 | 26.2± 9.9 | 194 (193) | 77/117 | 49.4± 13.5 | 14.7± 11.7 |
| SITE 2 (KUT) | 169 (139) | 100/69 | 35.9± 13.6 | 6.0± 5.4 | 17 (17) | 11/6 | 43.9± 13.3 | 27.7± 10.1 | 186 (156) | 111/75 | 36.7± 13.7 | 8.3± 9.1 |
| SITE 3 (SWA) | 101 (97) | 86/15 | 28.4± 7.9 | 4.4± 3.8 | 0 | - | - | - | 101 (97) | 86/15 | 28.4± 7.9 | 4.4± 3.8 |
| SITE 4 (UTO) | 170 (24) | 78/92 | 35.6± 17.5 | 6.7± 6.5 | 62 (32) | 36/26 | 38.7± 11.6 | 20.4± 11.4 | 232 (56) | 114/118 | 36.4± 16.2 | 14.5± 11.8 |
| TOTAL | 564 (383) | 310/254 | 38.0± 16.1 | 6.3± 5.6 | 149 (119) | 78/71 | 42.3± 12.5 | 24.9± 10.7 | 713 (502) | 388/325 | 38.9± 15.5 | 10.7± 10.6 |

Fig. 11

| DEMOGRAPHIC CHARACTERISTICS OF PATIENTS INCLUDED IN INDEPENDENT VALIDATION DATASET | | | | | | | | | | | | |
|---|---|---|---|---|---|---|---|---|---|---|---|---|
| SITE | HEALTHY CONTROLS (HCS) | | | | MDD PATIENTS (MDDS) | | | | SUM | | | |
| | NUMBER OF PARTICIPANTS | MALE/FEMALE | AGE | BDI | NUMBER OF PARTICIPANTS | MALE/FEMALE | AGE | BDI | NUMBER OF PARTICIPANTS | MALE/FEMALE | AGE | BDI |
| SITE 5 (HKH) | 29 (29) | 12/17 | 45.4± 9.5 | 5.1± 4.6 | 33 (33) | 20/13 | 44.8± 11.5 | 28.5± 8.7 | 62 (62) | 32/30 | 45.1± 10.5 | 17.6± 13.7 |
| SITE 6 (HRC) | 49 (49) | 13/36 | 41.7± 11.7 | 9.1± 8.5 | 16 (16) | 6/10 | 40.5± 11.5 | 35.3± 9.5 | 65 (65) | 19/46 | 41.4± 11.5 | 15.6± 14.3 |
| SITE 7 (HUH) | 66 (66) | 29/37 | 34.6± 13.0 | 6.9± 5.9 | 57 (57) | 32/25 | 43.3± 12.2 | 30.9± 9.0 | 123 (123) | 61/62 | 38.6± 13.3 | 18.0± 14.1 |
| SITE 8 (UYA) | 120 (120) | 50/70 | 45.9± 19.5 | 7.1± 5.6 | 79 (78) | 36/43 | 50.3± 13.6 | 29.7± 10.7 | 199 (198) | 86/113 | 47.6± 17.5 | 16.0± 13.6 |
| TOTAL | 264 (264) | 104/160 | 42.2± 16.5 | 7.2± 6.3 | 185 (184) | 94/91 | 46.3± 13.0 | 30.3± 9.9 | 449 (448) | 198/251 | 43.9± 15.3 | 16.7± 13.9 |

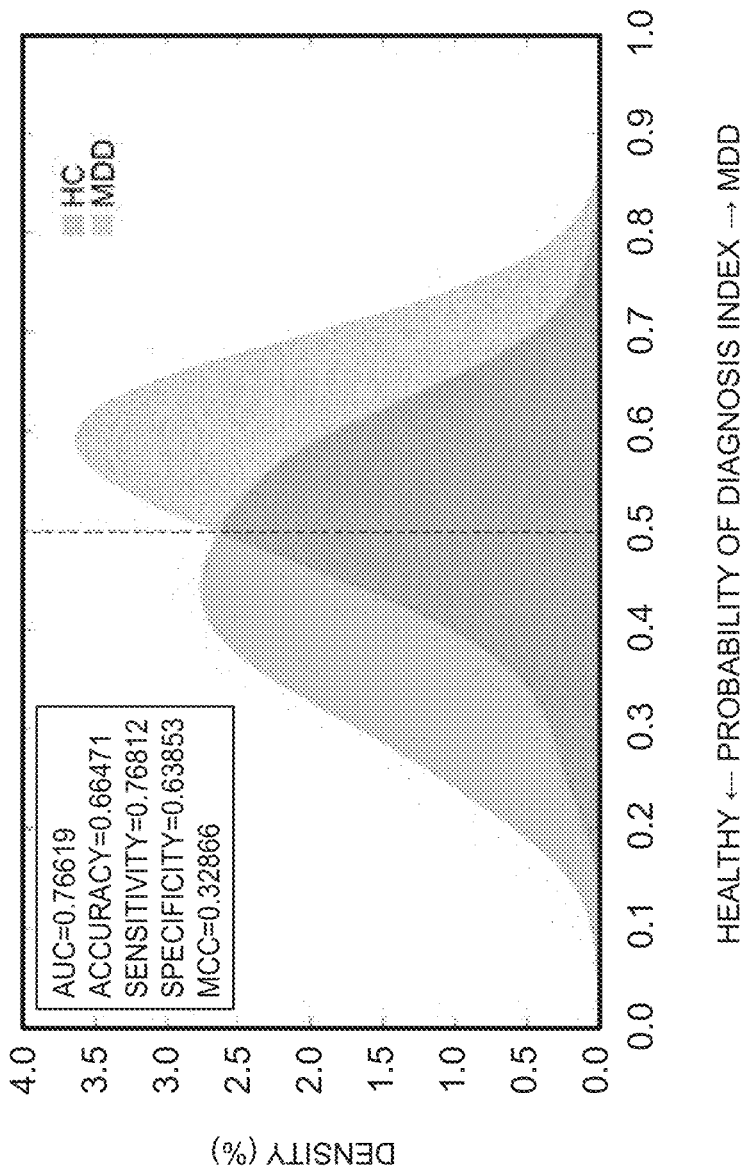

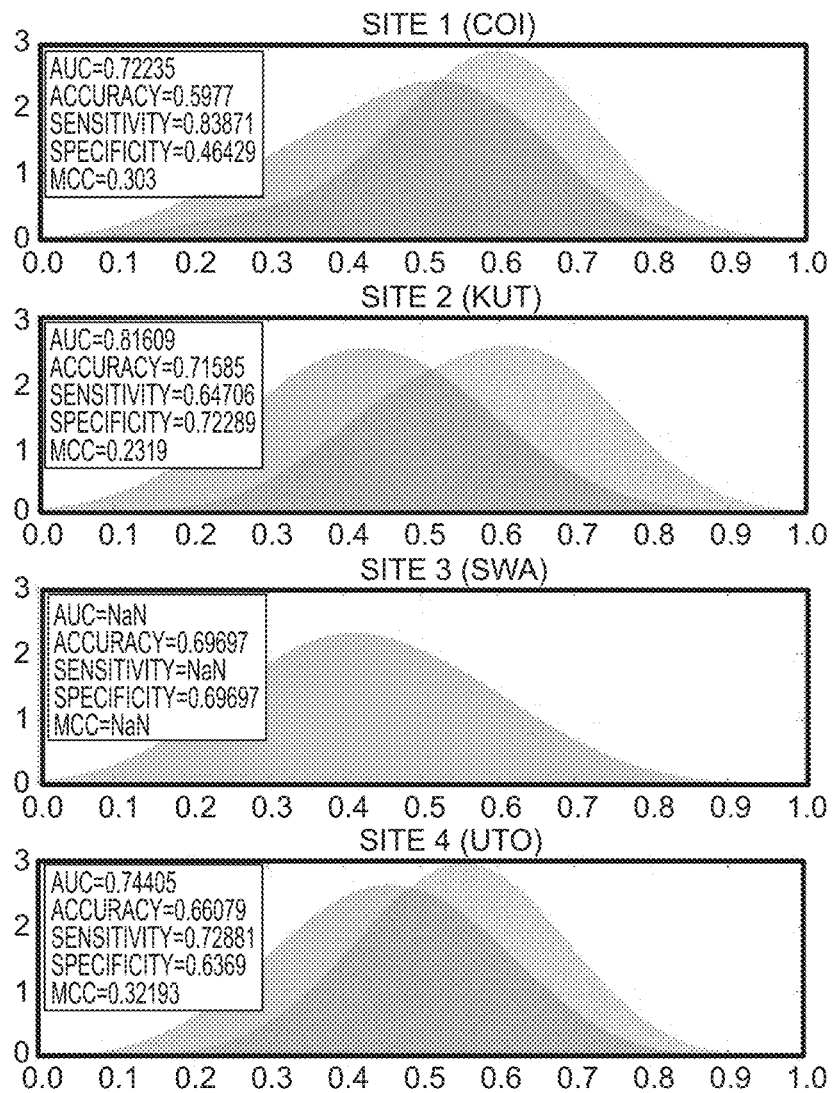

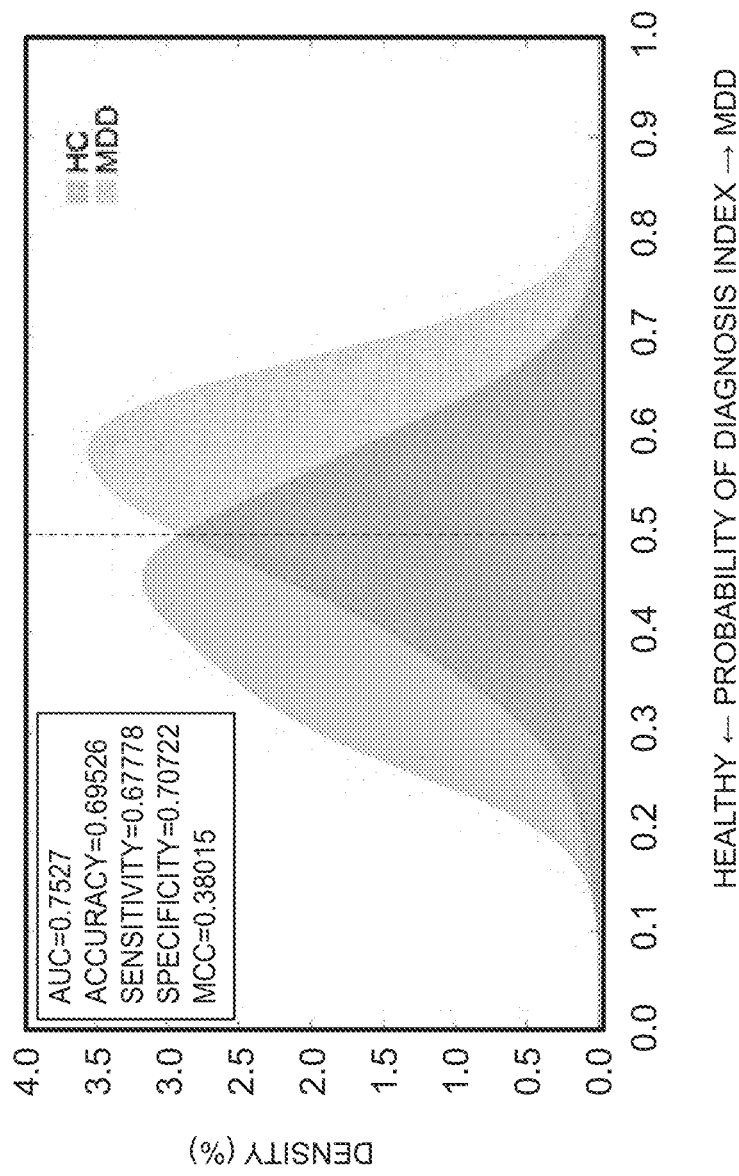

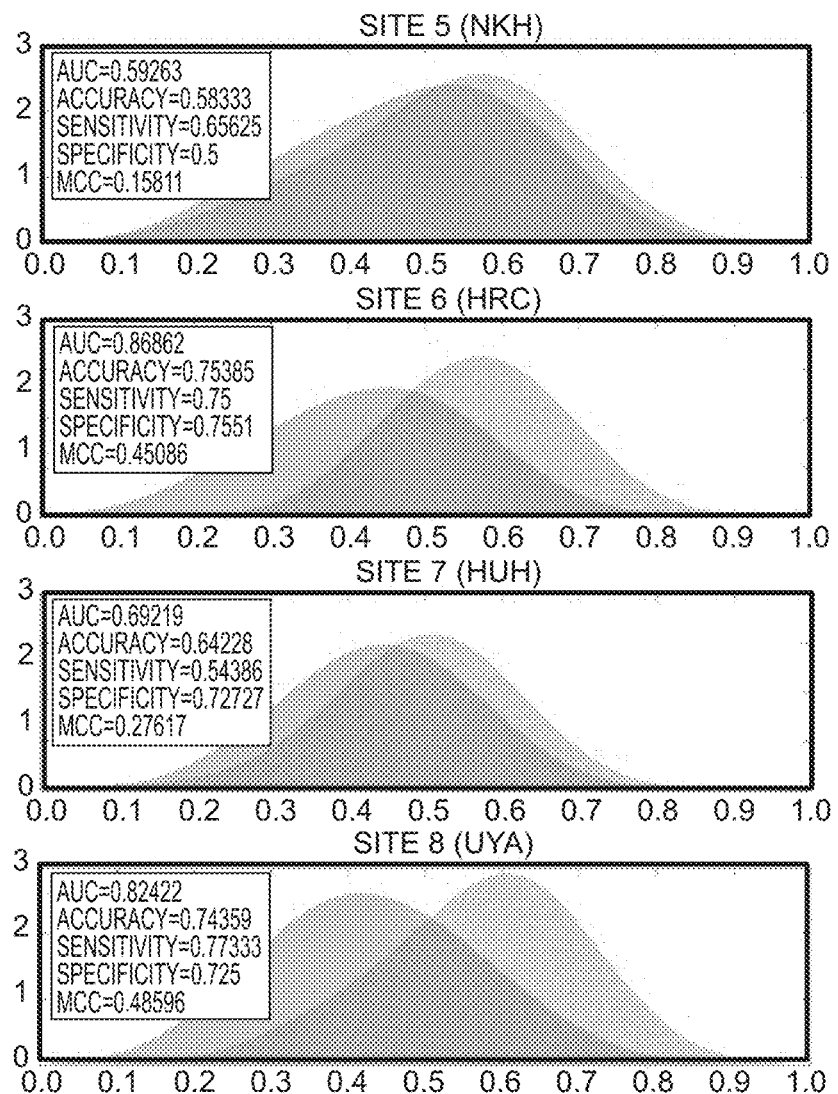

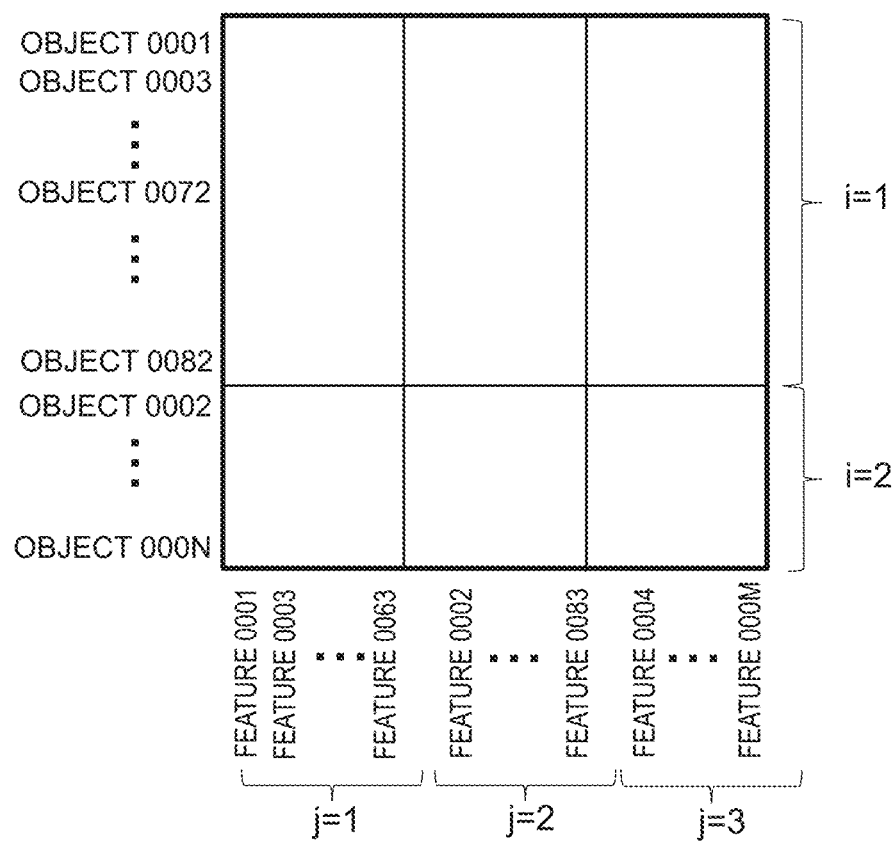

MULTIPLE CLUSTERING

MULTIPLE CO-CLUSTERING

Fig. 23   MULTIPLE CO-CLUSTERING
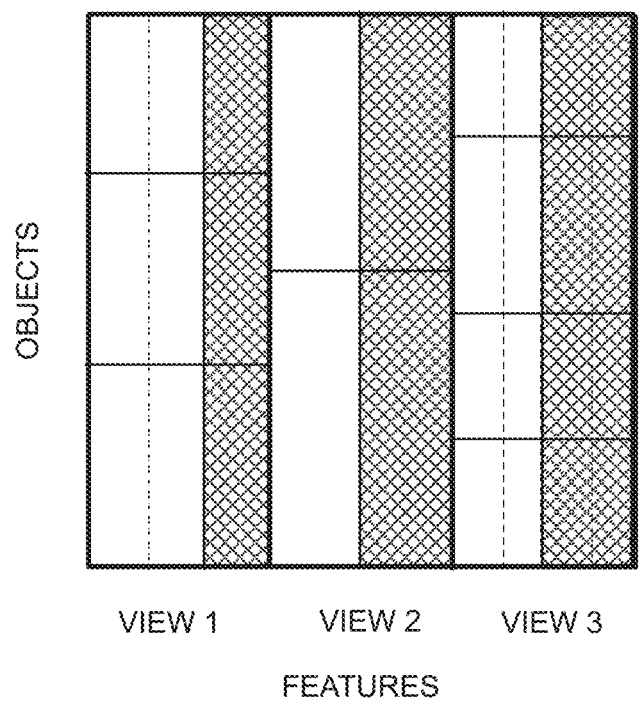
Fig. 27
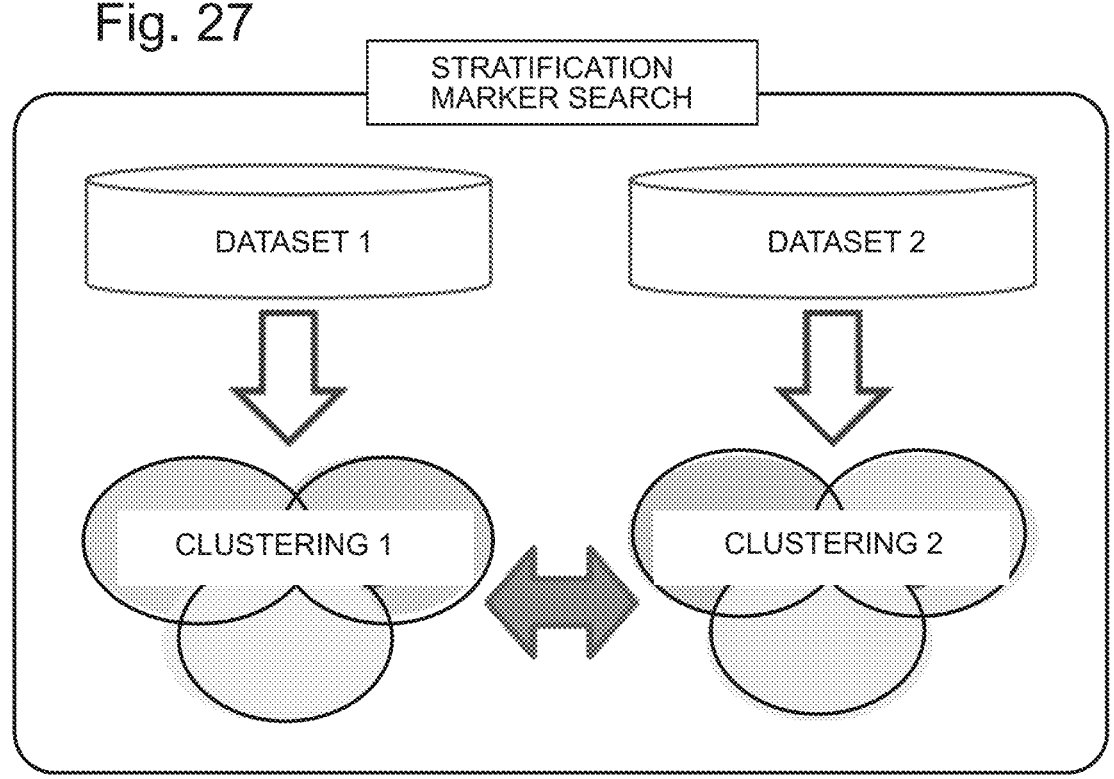

Fig. 26A

| DATASET 1 | | |
|---|---|---|
| FACILITY | HEALTHY SUBJECTS | PATIENTS OF DEPRESSION DISORDER |
| 1 | 112 | 62 |
| 2 | 166 | 17 |
| 3 | 99 | 0 |
| 4 | 168 | 59 |
| TOTAL | 545 | 138 |

Fig. 26B

| DATASET 2 | | |
|---|---|---|
| FACILITY | HEALTHY SUBJECTS | PATIENTS OF DEPRESSION DISORDER |
| 5 | 28 | 32 |
| 6 | 49 | 16 |
| 7 | 66 | 57 |
| 8 | 120 | 76 |
| TOTAL | 263 | 181 |

| NUMBER OF FUNCTIONAL CONNECTIVITY LINKS (FC) | | DATASET 2 | |
|---|---|---|---|
| | | VIEW 1 (93) | VIEW 2 (6) |
| DATASET 1 | VIEW 1 (92) | 92 | 0 |
| | VIEW 2 (7) | 1 | 6 |

CLASSIFIED TO ONE SAME CLUSTER ONCE
BUT TO DIFFERENT CLUSTERS THE NEXT TIME

Fig. 31
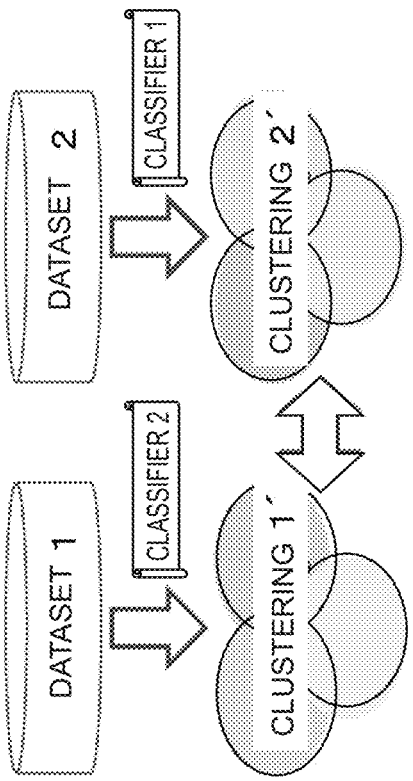
(B) CLUSTER BY USING MUTUAL CLASSIFIERS
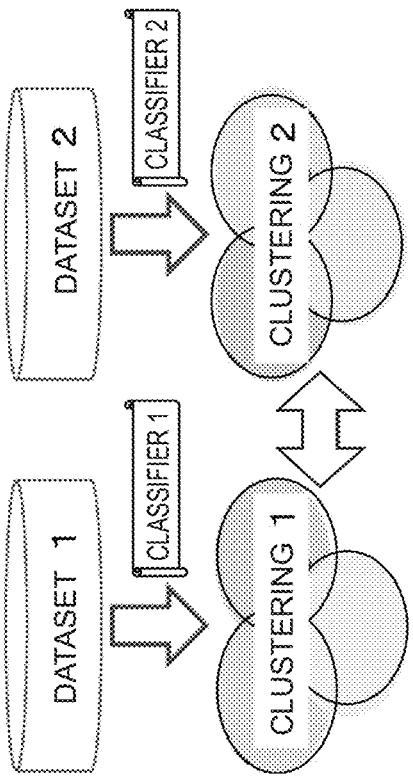
(A) CLUSTER DATASETS 1 AND 2 INDEPENDENTLY

Fig. 33A

| ARI | | DATASET 2 | |
|---|---|---|---|
| | | VIEW 1 | VIEW 2 |
| DATASET 1 | VIEW 1 | 0.47* | 0 |
| | VIEW 2 | 0.02 | 0.51* |

Fig. 34

| | | CLUSTERING 1' (VIEW 1) | | | |
|---|---|---|---|---|---|
| | CLUSTER | 2 | 3 | 1 | 4 |
| CLUSTERING 1 (VIEW 1) | 1 | 47 | 9 | 2 | 0 |
| | 2 | 0 | 24 | 4 | 0 |
| | 4 | 2 | 20 | 0 | 0 |
| | 3 | 2 | 0 | 23 | 1 |
| | 5 | 0 | 0 | 0 | 4 |

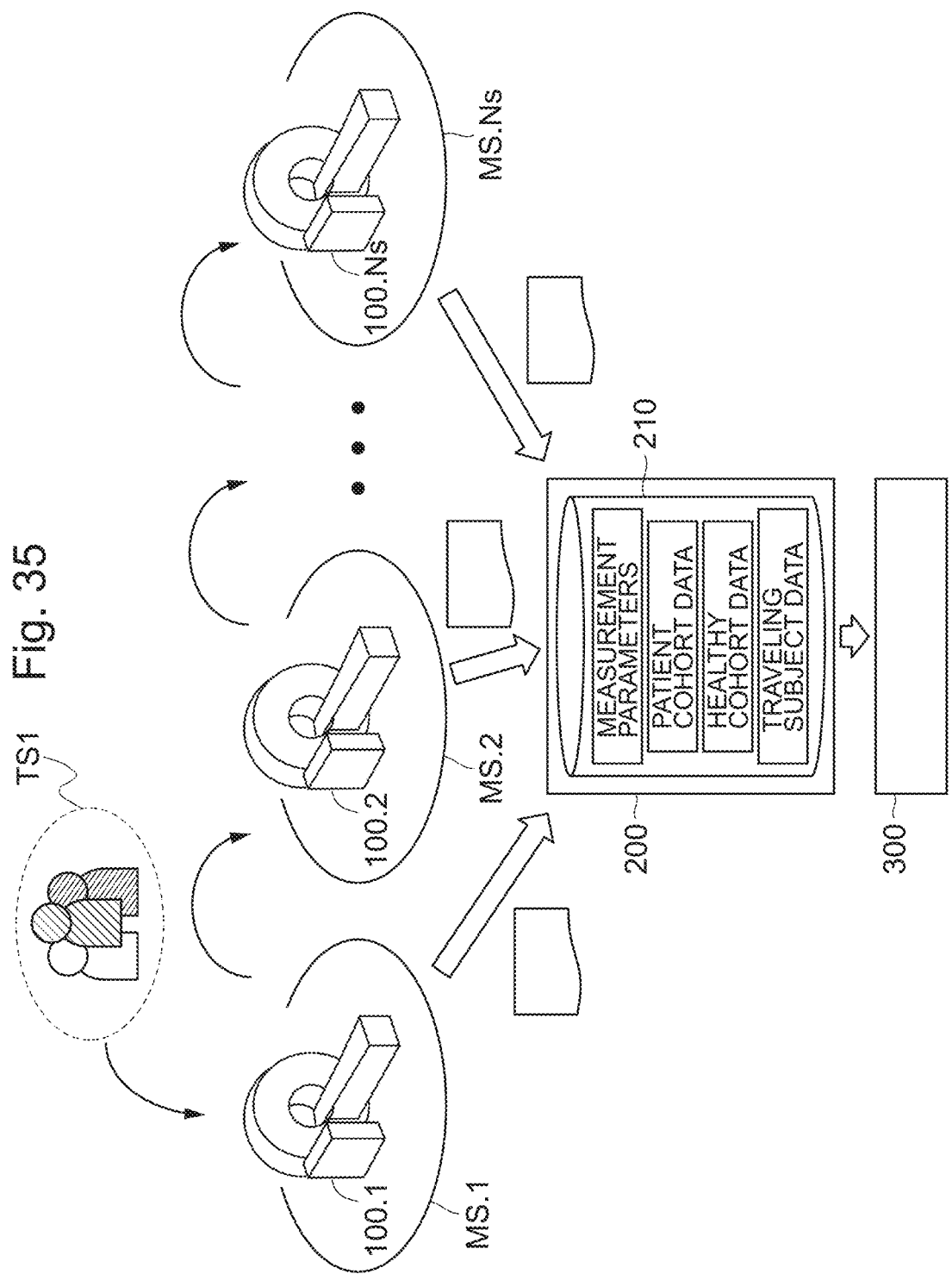

SRPBS MULTI-DISEASE DATASET

TRAVELING SUBJECT DATASET

Fig. 40A

DEMOGRAPHIC CHARACTERISTICS OF PATIENTS IN SRPBS MULTI-DISEASE DATASET

| SITE | HC | | | MDD | | | ASD | | |
|---|---|---|---|---|---|---|---|---|---|
| | NUMBER OF PARTICIPANTS | MALE /FEMALE | AGE (yr) | NUMBER OF PARTICIPANTS | MALE /FEMALE | AGE (yr) | NUMBER OF PARTICIPANTS | MALE /FEMALE | AGE (yr) |
| ATR TIMTRIO (ATT) | 31 | 28/3 | 23.0±1.9 | 0 | - | - | 0 | - | - |
| ATR VERIO (ATV) | 77 | 60/17 | 22.6±2.0 | 0 | - | - | 0 | - | - |
| HIROSHIMA UIVERSITY HOSPITAL (HUH) | 66 | 29/37 | 34.6±13.0 | 57 | 25/32 | 43.3±12.2 | 0 | - | - |
| HIROSHIMA KAJIKAWA HOSPITAL (HKH) | 29 | 12/17 | 45.4±9.5 | 23 | 10/13 | 43.6±11.6 | 0 | - | - |

Fig. 40B

| | OCD | | | SCZ | | | ALL | | | *1 |
|---|---|---|---|---|---|---|---|---|---|---|
| | NUMBER OF PARTICIPANTS | MALE /FEMALE | AGE (yr) | NUMBER OF PARTICIPANTS | MALE /FEMALE | AGE (yr) | NUMBER OF PARTICIPANTS | MALE /FEMALE | AGE (yr) | |
| | 0 | - | - | 0 | - | - | 31 | 28/3 | 23.0±1.9 | ✓ |
| | 0 | - | - | 0 | - | - | 77 | 60/17 | 22.6±2.0 | ✓ |
| | 0 | - | - | 0 | - | - | 123 | 54/69 | 38.6±13.3 | - |
| | 0 | - | - | 0 | - | - | 52 | 22/30 | 44.6±10.5 | - |

Fig. 40C

| | | | | | | | |
|---|---|---|---|---|---|---|---|
| CENTER OF INNOVATION IN HIROSHIMA UNIVERSITY (COI) | 10 | 5/5 | 43.5±13.5 | 38 | 18/20 | 44.0±11.0 | 0 | - |
| KYOTO PREFECTURAL UNIVERSITY OF MEDECINE (KPM) | 52 | 28/24 | 29.1±7.3 | 0 | - | - | 0 | - |
| KYOTO UNIVERSITY (KUT) | 35 | 18/17 | 36.3±8.9 | 9 | 5/4 | 45.2±15.9 | 0 | - |
| SHOWA UNIVERSITY (SWA) | 40 | 32/8 | 30.9±8.5 | 0 | - | - | 49 | 45/4 | 32.9±8.1 |
| UNIVERSITY OF TOKYO (UTO) | 142 | 72/70 | 29.7±11.0 | 34 | 16/18 | 38.5±9.9 | 0 | - |
| SUMMARY | 482 | 284/198 | 30.6±10.9 | 161 | 74/87 | 42.6±11.7 | 49 | 45/4 | 32.9±8.1 |

*1: PARTICIPANTS WERE SCANNED USING STANDARDIZED PROTOCOLS

Fig. 40D

| | | | | | | | | |
|---|---|---|---|---|---|---|---|---|
| 0 | - | - | 0 | - | - | 48 | 23/25 | 43.9±11.4 | ✓ |
| 65 | 30/35 | 31.9±9.8 | 0 | - | - | 117 | 58/59 | 30.6±8.8 | - |
| 0 | - | - | 22 | 11/11 | 40.4±8.4 | 66 | 34/32 | 38.9±10.2 | ✓ |
| 0 | - | - | 12 | 11/1 | 41.8±9.2 | 101 | 88/13 | 33.2±8.9 | ✓ |
| 0 | - | - | 14 | 7/7 | 33.3±14.0 | 190 | 95/95 | 31.6±11.5 | ✓ |
| 65 | 30/35 | 31.9±9.8 | 48 | 29/19 | 38.7±10.8 | 805 | 462/343 | 33.7±11.9 | - |

Fig. 41A

RESTING STATE fMRI IMAGING PROTOCOL IN SRPBS MULTI-DISEASE DATASET

| SITE | ATR TIMTRIO | ATR VERIO | CENTER OF INNOVATION IN HIROSHIMA UNIVERSITY | HIROSHIMA UNIVERSITY HOSPITAL |
|---|---|---|---|---|
| ABBREVIATION | ATT | ATV | COI | HUH |
| MRI SCANNER | Siemens TimTrio | Siemens Verio | Siemens Verio | GE Signa HDxt |
| STATIC MAGNETIC FIELD STRENGTH | 3.0 T | 3.0 T | 3.0 T | 3.0 T |
| NUMBER OF RECEIVING COILS | 12 | 12 | 12 | 8 |
| FIELD OF VIEW (mm) | 212 × 212 | 212 × 212 | 212 × 212 | 256 × 256 |
| MATRIX | 64 × 64 | 64 × 64 | 64 × 64 | 64 × 64 |
| SLICE NUMBER | 40 or 39 | 39 | 40 | 32 |
| VOLUME NUMBER | 240 | 240 | 240 | 143 |

Fig. 41B

| | HIROSHIMA KAJIKAWA HOSPITAL | KYOTO PREFECTURAL UNIVERSITY OF MEDICINE | SHOWA UNIVERSITY | KYOTO UNIVERSITY TIMTRIO | UNIVERSITY OF TOKYO |
|---|---|---|---|---|---|
| | HKH | KPM | SWA | KUT | UTO |
| | Siemens Spectra | Philips Achieva | Siemens Verio | Siemens TimTrio | GE MR750w |
| | 3.0 T | 3.0 T | 3.0 T | 3.0 T | 3.0 T |
| | 12 | 8 | 12 | 32 | 24 |
| | 192 × 192 | 192 × 192 | 212 × 212 | 212 × 212 | 212 × 212 |
| | 64 × 64 | 64 × 64 | 64 × 64 | 64 × 64 | 64 × 64 |
| | 38 | 39 | 40 | 40 | 40 |
| | 107 | 194 | 240 | 240 | 240 |

Fig. 41C

| | | | |
|---|---|---|---|
| IN-PLANE RESOLUTION (mm) | 3.3125 × 3.3125 | 3.3125 × 3.3125 | 3.3125 × 3.3125 | 4.0 × 4.0 |
| SLICE THICKNESS (mm) | 3.2 | 3.2 | 3.2 | 3.2 |
| SLICE GAP (mm) | 0.8 | 0.8 | 0.8 | 0 |
| TR (ms) | 2,500 | 2,500 | 2,500 | 2,000 |
| TE (ms) | 30 | 30 | 30 | 27 |
| TOTAL SCAN TIME (min:s) | 10:00 | 10:00 | 10:00 | 5:00 |
| FLIP ANGLE (deg) | 80 | 80 | 80 | 90 |
| SLICE GETTING ORDER | Ascending | Ascending | Ascending | Ascending (Interleaved) |
| PHASE ENCODING DIRECTION | PA | PA | AP | PA |
| EYES CLOSED (Closed)/FIXATE (fixate) | Fixate | Fixate | Fixate | Fixate |

Fig. 41D

| | | | | |
|---|---|---|---|---|
| 3.0 × 3.0 | 3.0 × 3.0 | 3.3125 × 3.3125 | 3.3125 × 3.3125 | 3.3125 × 3.3125 |
| 3.0 | 3.0 | 3.2 | 3.2 | 3.2 |
| 0 | 0 | 0.8 | 0.8 | 0.8 |
| 2,700 | 2,000 | 2,500 | 2,500 | 2,500 |
| 31 | 30 | 30 | 30 | 30 |
| 5:00 | 6:30 | 10:00 | 10:00 | 10:00 |
| 90 | 80 | 80 | 80 | 80 |
| Ascending | Ascending | Ascending | Ascending | Ascending |
| AP | AP | PA | PA | PA |
| Fixate | Closed | Fixate | Fixate | Fixate |

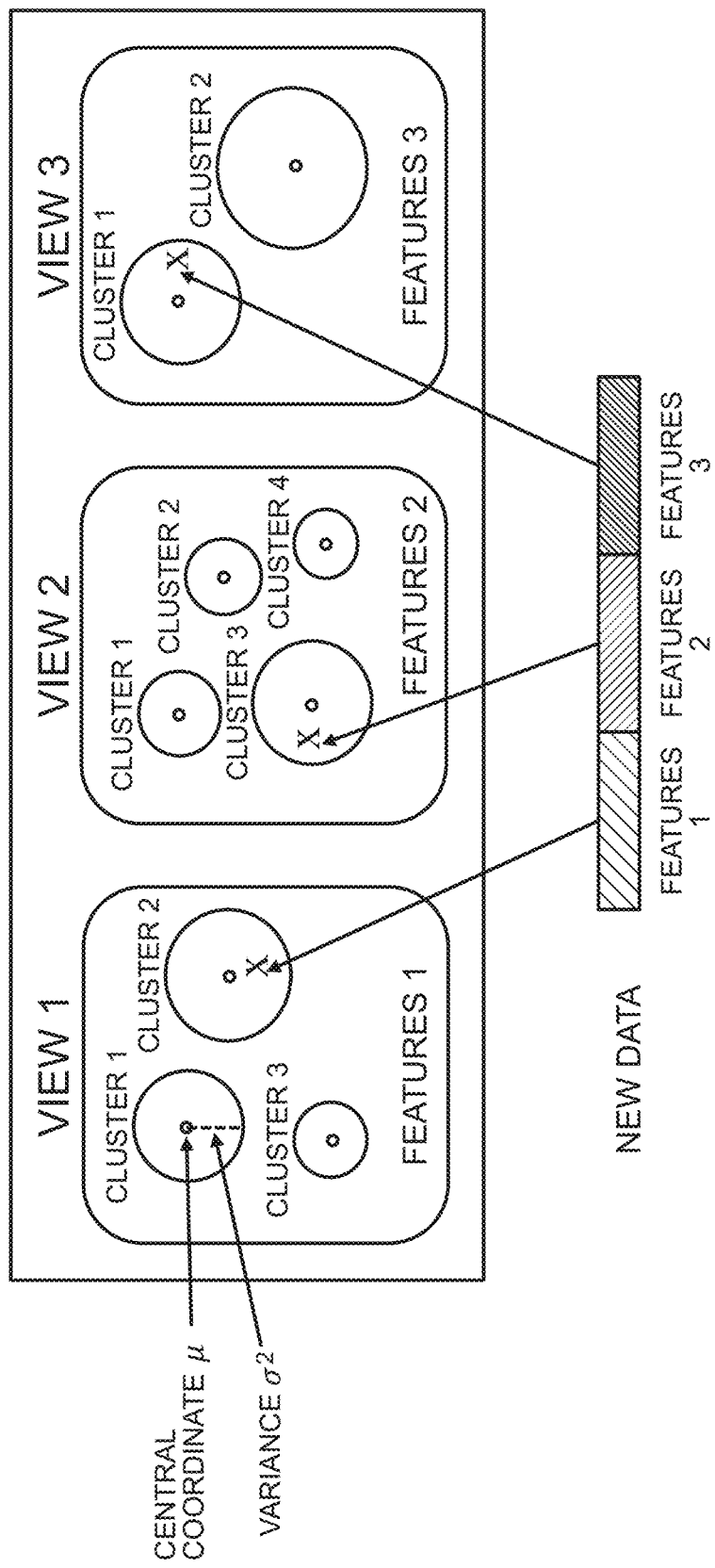

BRAIN FUNCTIONAL CONNECTIVITY CORRELATION VALUE CLUSTERING DEVICE, BRAIN FUNCTIONAL CONNECTIVITY CORRELATION VALUE CLUSTERING SYSTEM, BRAIN FUNCTIONAL CONNECTIVITY CORRELATION VALUE CLUSTERING METHOD, BRAIN FUNCTIONAL CONNECTIVITY CORRELATION VALUE CLASSIFIER PROGRAM, BRAIN ACTIVITY MARKER CLASSIFICATION SYSTEM AND CLUSTERING CLASSIFIER MODEL FOR BRAIN FUNCTIONAL CONNECTIVITY CORRELATION VALUES

TECHNICAL FIELD

The present invention relates to a technique for clustering brain functional connectivity correlation values measured by functional brain imaging by a plurality of devices and, more specifically, to a brain functional connectivity correlation value clustering device, a brain functional connectivity correlation value clustering system, a brain functional connectivity correlation value clustering method, a brain functional connectivity correlation value classifier program, a brain activity marker classification system and a clustering classifier model for brain functional connectivity correlation values. The present application claims convention priority of Japanese Patent Application No. 2020-068669 filed on Apr. 6, 2020, and the entire contents described in this Japanese application are incorporated herein by reference.

BACKGROUND ART (Data Driven Clustering Method)

Recent developments in artificial intelligence technology, particularly in data-driven artificial intelligence technology has realized applications which sometimes rival, and in some aspects surpass, human abilities in the fields of speech recognition, translation, image recognition and so on (for example, see Patent Literature 1).

In the field of medical technology also, use of machine learning including deep learning is increasing in, for example, diagnostic imaging. Deep learning refers to machine learning using multi-layered neural networks and, in the field of image recognition, it is known that a method of learning using Convolutional Neural Network (hereinafter referred to as "CNN") shows a performance significantly higher than conventional methods (for example, see Patent Literature 2).

By way of example, in the fields of endoscopic diagnostic imaging for colorectal cancer and the like, diagnostic devices are now used in practical services which show accuracy of diagnosis higher than those of humans (Non-Patent Literature 1).

It should be noted that, from the viewpoint of classification of machine learning, almost all of such artificial intelligence techniques belong to the category of so-called "supervised learning," which requires preparation of a huge number of pairs of label data and input data (for example, image data) to be used as inputs for training artificial intelligence.

By contrast, data-driven artificial intelligence may be applied to tasks of classifying given data into a number of clusters based on their features. For such applications, "unsupervised learning" is known for which correct data is not available, as well as "semi-supervised learning" combining learning with a small amount of "correct-labeled training data" with a large amount of "unlabeled training data" (for example, Patent Literature 3).

By way of example, according to Patent Literature 3, "semi-supervised learning refers to a method of learning based on a relatively small amount of labeled data and unlabeled data, and it includes, by way of example, a bootstrap method in which learning model for classification is generated using labeled data (teacher data T including state data S and label data L), and the learning model is additionally trained to improve the precision of learning by using the learning model and unlabeled data (state data S), and a graph base algorithm in which a learning model as a classifier is generated by grouping based on labeled and unlabeled data distributions." As described in the examples above, however, in the "semi-supervised learning," only a small number of training data have associated teacher data. It is assumed that with this data, a classifier is generated first, and then the classifier itself is re-trained by using a huge amount of "unlabeled training data."

(Biomarker)

In the following, we take examples of applications of discrimination and clustering using artificial intelligence technology in the medical field.

A "biomarker" refers to biological information converted into a numerical value or quantified as an index for quantitatively comprehending any biological changes in a living body The FDA (the United States Food and Drug Administration) defines a biomarker as "a characteristic that is objectively measured and evaluated as an indicator of normal biological processes, pathogenic processes or pharmacological responses to a therapeutic intervention." Biomarkers representative of a state of or a change in a disease, or a degree of healing are used as surrogate markers (substitute markers) to monitor efficacy in clinical tests of new drugs. The blood sugar level, the cholesterol level and the like, are representative biomarkers used as indexes of lifestyle diseases. Biomarkers include not only substances of biological origin contained in urine or blood but also electrocardiogram, blood pressure, PET (positron emission tomography) images, bone density, lung function and the like. Developments in genomic analysis and proteome analysis have led to the discovery of various biomarkers related to DNA, RNA or biological protein.

Biomarkers are promising for measuring therapeutic efficacy after the onset of a disease and, in addition, as routine preventive indexes, promising for disease prevention. Further, biomarkers are expected to be applied to individualized medicine for selecting effective treatment avoiding side effects.

For example, a biomarker for determining possibility of having a pulmonic disease using genetic information is disclosed (Patent Document 4). According to Patent Literature 4, a "biomarker" or a "marker" is "biological molecules that can be objectively measured as representing features of biological state of the biological system." Patent Literature 4 describes the biomarkers as "typically, biomarker measurements represent information related to quantitative measurement of expression product, which typically is protein or polypeptide. The present invention envisions determining biomarker measurements determined on the RNA (pre-translation) level or on protein level (including post-translational modification)." Patent Literature 4 shows examples of classifiers to be used as the "classification system" of such biomarker measurements, including a decision tree, a Bayesian classifier, a Bayesian belief network, k-nearest neighbor method, case-based reasoning and a support vector machine.

However, because diagnosis at present in the field of neurological/mental disorders is largely based on symptoms in accordance with the Diagnostic and Statistical Manual of Mental Disorders, v.5, it should in fairness be stated that molecular markers and the like are still in a research phase although biomarkers usable as objective indexes from a biochemical or molecular genetics viewpoint have been studied.

Nevertheless, a disease determination system has been reported which uses an NIRS (Near-InfraRed Spectroscopy) technique to classify mental disorders such as schizophrenia and depression based on features of hemoglobin signals measured by biological optical measurement (Patent Literature 5).

(Biomarker Based on Brain Activities)

Meanwhile, in the field of so-called diagnostic imaging, there is a so-called "image biomarker" different from the concept of biomarker as "biological molecules" described above. For example, there are researches related to neurotransmission function or receptor function analysis using PET for molecular imaging in cranial nerve regions.

Further, in nuclear Magnetic Resonance Imaging (MRI), changes appearing in detected signals in accordance with changes in the blood stream make it possible to visualize portions of a brain activated in response to an external stimulus. Such nuclear magnetic resonance imaging is specifically referred to as fMRI (functional MRI).

An fMRI uses a common MRI apparatus with additional hardware and software necessary for fMRI measurement.

The changes in blood stream cause changes in NMR signal intensity, since oxygenated hemoglobin and deoxygenated hemoglobin in the blood have different magnetic properties. Oxygenated hemoglobin is diamagnetic and does not have any influence on relaxation time of hydrogen atoms in the surrounding water whereas deoxygenated hemoglobin is paramagnetic and changes surrounding magnetic field. Therefore, when the brain is stimulated and local blood stream increases, any resulting changes in oxygenated hemoglobin can be detected by MRI signals. Commonly used stimuli to a subject may include, for example, visual stimulus, audio stimulus, or performance of a prescribed task.

In the studies of the brain functions, brain activities are measured by measuring increase in the nuclear magnetic resonance signal (MRI signal) of hydrogen atoms representing a phenomenon where the deoxygenated hemoglobin level in red blood cells decrease in minute veins or capillary vessels (BOLD effect).

The blood oxygen level dependent signal that reflects a brain activity measured by fMRI devices is referred to as a BOLD signal (Blood Oxygen Level Dependent Signal).

Particularly, in studies related to the human motor functions, brain activities are measured by the fMRI as described above while a subject is performing some physical activity.

For human subjects, it is necessary to measure the brain functions in a non-invasive manner. In this aspect, a decoding technique has been developed to extract more detailed information from fMRI data. Specifically, a voxel-by-voxel (voxel: volumetric pixel) brain activity analysis of the brain by the fMRI enables the estimation of stimulus input or the state of recognition from spatial patterns of the brain activities.

Further, as a development of such a decoding technique, Patent Literature 6 discloses a method of brain function analysis for realizing "diagnostic biomarkers" based on functional brain imaging for a neurological/mental disorder. According to this method, from measurement data of resting-state functional connectivity MRI of a healthy cohort and a patient cohort, a correlation matrix (brain functional connectivity parameters) of degrees of activities between prescribed brain regions is derived for each subject. Feature extraction is performed by regularized canonical correlation analysis on the correlation matrix and on the attributes of subjects including diseased/healthy labels of the subjects. Based on the results of regularized canonical correlation analysis, a discriminator that functions as a biomarker is generated from discriminant analysis by sparse logistic regression (SLR). It has been indicated that by such a technique of machine learning, results of mental disease diagnosis can be predicted based on connections among brain regions derived from fMRI data in the resting state. Further, verification of the prediction performance indicated that the prediction is not only applicable to the brain activities measured in a certain facility but also generalizable, to some extent, to the brain activities measured in a different facility.

Further, technical improvements are made to enhance generalization performance of the above-described "diagnostic biomarkers" (Patent Literature 7).

Recently, as in the human connectome project in the United States, obtaining and sharing large scale brain image data come to be recognized as having a significant meaning in filling in the gaps between basic neuro-scientific research and clinical applications such as diagnosis and therapy of mental diseases or psychiatric disorder (Non-Patent Literature 2).

In 2013, Japan Agency for Medical Research and Development, which is one of the Japanese National Research and Development Agencies, organized a Decoded Neurofeedback (DecNef) project, in which eight laboratories collect data of functional magnetic resonance in resting state (resting state functional MRI) covering five diseases and 2,239 samples from a plurality of sites, and the data is shared through a database (https://bicr-resource.atr.jp/decnefpro/) of a plurality of diseases at a plurality of sites mainly of SRPBS (Strategic Research Program for Brain Science, https://www.amed.go.jp/program/list/01/04/001 nopro.html). This project identified biomarkers based on resting state functional connectivity (resting state functional MRI) of several psychiatric disorders that can be generalized to fully independent cohorts.

As described above, diagnosis of a healthy cohort and a patient cohort have attained some positive results. Meanwhile, it is known that the patients' cohort generally diagnosed as having "depression" may actually be divided into several subtypes. For example, common "antidepressant" work so well to achieve remission for some patients while not so well to other patients who are "treatment-resistant."

There has been an attempt to classify such patients of "depression" by applying clustering using data-driven artificial intelligence to the above-described "brain functional connectivity parameters," and some references report that a certain tendency is observed (Non-Patent Literatures 3 and 4).

In order to practically utilize such a method of classifying subtypes of a disorder group, however, it is necessary to obtain large-scale data of the disorder group.

However, large scale collection of brain image data of healthy people, let alone patients, is difficult.

Therefore, when acquiring multisite measurement data to realize large-scale data collection, site differences between measured data in respective measuring sites will be the chief concern. Non-Patent Literature 4 mentioned above notes that the "generalization" of clustering of a huge amount of measurements data from many facilities is a problem to be solved in the future.

For instance, Non-Patent Literature 3 indicated that patients of depression were stratified with four subtypes having different therapeutic responses to TMS (transcranial magnetic stimulation). It is pointed out, however, in a different reference (Non-Patent Literature 5) that in the process of finding brain functional connectivity indexes, data of depression symptoms are used twice, and because of the overtraining, the statistical significance of the relation with depression symptoms could not be confirmed and stratification stability was not satisfactory.

Therefore, at least at present, precision of stratification in independent validation data regarding depression has not been confirmed.

Meanwhile, by way of example, for evaluating the site-to-site differences of measurement data when MRI measurements are done at a plurality of measurement sites, adoption of a so-called "traveling subject" is proposed, wherein a large number of participants travel to and are measured at the plurality of sites, in order to evaluate an effect on measurement bias on the resting state functional connectivity (Non-Patent Literatures 6 and 7).

In any case, when attributes of subjects are to be classified based on fMRI data, in order to avoid the problem of overtraining, it is a common practice in the field of machine learning to evaluate a classifier using leave-one-subject-out cross validation in which one subject is left out to be used for validation, or using 10-fold cross validation in which data is divided to ten groups, nine of which are used for learning and the remaining one is used for validation; however, recently, it is recognized in the field of psychiatry as well that machine learning applied to a small number of samples taken from a single facility possibly leads to inflated prediction.

Machine learning on a small amount of data is highly prone to overtraining because of noises or specific tendencies of training data derived from fMRI devices of specific facilities, or methods of measurement, experimenters or participant groups.

By way of example, it is reported that a classifier discriminating autism spectrum disorder from anatomic brain images shows specificity and sensitivity of 90% or higher when used for training data of United Kingdom that was used for development, while its performance is as low as 50% when applied to data of Japanese people. From the foregoing, we assume that a classifier not validated using an independent validation cohort consisting of a group of subjects and a facility that are totally different from the training data does not bear either scientific or practical significance.

The applicant of the present application reports a "method of harmonization" in order to compensate for the site-to-site differences among measurement sites (Non-Patent Literature 8).

Descriptions of Patent Literatures 1 to 7 and Non-Patent Literatures 1 to 8 are incorporated herein by reference.

CITATION LIST

Patent Literature

PL1: JP2018/147193 A1 (WO2018/147193)
PL2: JP2019-198376 A
PL3: JP2020-024139 A
PL4: JP2019-516950 A (WO2017/162773)
PL5: JP2005/025421 A1 (WO2005/025421)
PL6: JP2015-62817 A
PL7: JP2017-196523 A

Non-Patent Literature

NPL 1: Japan Agency for Medical Research and Development "AI mounting endoscope diagnosis assisting program approved—Expected to assist physicians' diagnosis" https://www.amed.go.jp/news/release 20181210.html
NPL2: Glasser M F, et al. The Human Connectome Project's neuroimaging approach. Nat Neurosci 19, 1175-1187 (2016)
NPL3: Andrew T Drysdale, Logan Grosenick, Jonathan Downar, Katharine Dunlop, Farrokh Mansouri, Yue Mengl, Robert N Fetcho, Benjamin Zebley, Desmond J Oathes, Amit Etkin, Alan F Schatzberg, Keith Sudheimer, Jennifer Keller, Helen S Mayberg, Faith M Gunning, George S Alexopoulos, Michael D Fox, Alvaro Pascual-Leone, Henning U Voss, B J Casey, Marc J Dubin & Conor Liston, "Resting-state connectivity biomarkers define neurophysiological subtypes of depression", nature medicine, VOLUME 23, NUMBER 1, JANUARY 2017
NPL4: Tomoki Tokuda, Junichiro Yoshimoto, Yu Shimizu, Go Okada, Masahiro Takamura, Yasumasa Okamoto, Shigeto Yamawaki, Kenji Doya, "Identification of depression subtypes and relevant brain regions using a data-driven approach", SCIENTIFIC REPORTS (2018) 8:14082 DOI:10.1038/s41598-018-32521-z
NPL5: Richard Dinga, Lianne Schmaal, Brenda W. J. H. Penninx, Marie Josevan Tol, Dick J. Veltman, Laura van Velzen, Maarten Mennes, Nic J. A. van der Wee, Andre F. Marquand, "Evaluating the evidence for biotypes of depression: Methodological replication and extension of Drysdale et al. (2017)", NeuroImage: Clinical 22 (2019) 101796
NPL6: Noble S, et al. Multisite reliability of MR-based functional connectivity. Neuroimage 146, 959-970 (2017)
NPL7: Pearlson G. Multisite collaborations and large databases in psychiatric neuroimaging advantages, problems, and challenges. Schizophr Bull 35, 1-2 (2009)
NPL8: Ayumu Yamashita, Noriaki Yahata, Takashi Itahashi, Giuseppe Lisi, Takashi Yamada, Naho Ichikawa, Masahiro Takamura, Yujiro Yoshihara, Akira Kunimatsu, Naohiro Okada, Hirotaka Yamagata, Koji Matsuo, Ryuichiro Hashimoto, Go Okada, Yuki Sakai, Jun Morimoto, Jin Narumoto, Yasuhiro Shimada, Kiyoto Kasai, Nobumasa Kato, Hidehiko Takahashi, Yasumasa Okamoto, Saori C Tanaka, Mitsuo Kawato, Okito Yamashita, and Hiroshi Imamizu, "Harmonization of resting-state functional MRI data across multiple imaging sites via the separation of site differences into sampling bias and measurement bias.", PLOS Biology. DOI: 10.1371/journal.pbio.3000042, http://journals.plos.org/plosbiology/article?id=10.1371/journal.pbio.3000042

SUMMARY OF INVENTION

Technical Problem

When we consider applying functional brain imaging such as functional Magnetic Resonance Imaging as described above to treatment of a neurological/mental disorder of the brain activity analysis, the analysis of brain activities using functional brain imaging as the above-described biomarker is promising as a non-invasive functional marker, and applications to development of a diagnostic method and to searching/identification of target molecules aiming toward drug discoveries for realizing basic remedies are also expected.

By way of example, consider a mental disorder. Practical biomarkers using genes are not yet established and, therefore, the development of therapeutic agents remains difficult, since it is difficult to determine the effect of medication.

In order to generate an identifier as a diagnostic marker or a classifier as a stratifying marker by machine learning based on the measured data of brain activities and to practically use this as a biomarker, it is necessary to improve the prediction precision of the biomarker generated by machine learning for brain activities measured at one facility. Further, it is also necessary that the biomarker generated in this manner can be generalized to brain activities measured at other facilities.

Specifically, when a discriminator for identifying a disorder or a classifier to subtypes of a disorder is to be built by machine learning based on the measured data of brain activities, the following two main problems must be addressed.

The first problem is the small size of samples.

The amount of data N representing the number of subjects is far smaller than the dimension M of measured data of brain activities, and parameters of the discriminator will easily be over-fitted to the training data.

Because of this over-fitting, the discriminator thus built exhibits very poor performance on newly sampled test data. The reason for this is that the test data were not used for training the discriminator.

Therefore, in order to discriminate and use essential features only with respect to desired generalization of the discriminator, appropriate feature selection and dimension reduction must be introduced.

The second problem is that the discriminator is clinically effective and scientifically reliable only when the built discriminator maintains satisfactory performance on MRI data scanned at an imaging site different from the site where the training data were collected.

This is a so-called generalization capability over a plurality of imaging sites.

Assume that massive brain image data related to psychiatric disorder are to be collected. The amount of data of brain images that can be obtained at one site is limited and, therefore, collection from a plurality of sites becomes necessary.

The site-to-site differences, however, represents a biggest barrier when brain image data are to be obtained from a plurality of sites.

Specifically, in clinical applications, it is often observed that a discriminator trained by using data obtained at a specific site cannot be generalized to data scanned at a different site.

Therefore, in the human connectome project mentioned above, so far, it is assumed that measurements are done at a single site, using a single scanner.

The present invention was made to solve the above-described problem and its object is to provide a brain functional connectivity correlation value clustering device, brain functional connectivity correlation value clustering system, a brain functional connectivity correlation value clustering method, and a clustering classifier model for brain functional connectivity correlation values, performing clustering of subjects having a prescribed attribute based on brain measurement data obtained at a plurality of facilities.

Another object of the present invention is to provide a brain functional connectivity correlation value classifier program and a brain activity marker classification system for realizing a classification marker based on brain activity measurements.

Solution to Problem

According to an aspect, the present invention provides a clustering device for clustering brain functional connectivity correlation values performing, based on measurement results of brain activities of objects, clustering of objects having at least one prescribed attribute among the objects, including a computing system for performing a process of the clustering based on measured values of brain activities, on a plurality of subjects including a first cohort of subjects having the prescribed attribute and a second cohort of subjects not having the prescribed attribute, the computing system including a storage device and a processor; wherein the processor is configured to perform the steps of i) storing, in the storage device, for each of the plurality of subjects, features based on a plurality of brain functional connectivity correlation values respectively representing time-wise correlation of brain activities between each of a prescribed plurality of pairs of brain regions, and ii) based on the features stored in the storage device, conducting supervised machine learning for generating an identifier model for discriminating presence/absence of the attribute; the processor performs, in the machine learning for generating an identifier model, the steps of generating a plurality of training sub-samples by performing under-sampling and sub-sampling from the first cohort of subjects and the second cohort of subjects, and selecting, for each of the training sub-samples, from a sum set of features used for generating the identifier by machine learning, features for clustering in accordance with importance of features belonging to the sum set; and the processor further performs the step of clustering the first cohort of subjects through multiple co-clustering of unsupervised learning, based on the selected features for clustering, and thereby generates a cluster classifier.

Preferably, the clustering device for clustering brain functional connectivity correlation values receives, from a plurality of brain activity measuring devices provided respectively at a plurality of measurement sites, information representing time-wise correlation of brain activities between each of a prescribed plurality of pairs of brain regions of each of a plurality of subjects; wherein the computing system includes a harmonization calculating means for correcting the plurality of brain functional connectivity correlation values of each of the plurality of subjects to remove measurement bias of the measurement sites and thereby storing corrected adjusted values as the features in the storage device.

Preferably, the process of generating an identifier by the machine learning involves ensemble learning of generating a plurality of identifier sub-models respectively for the plurality of training samples, and integrating the plurality of identifier sub-models to generate the identifier model.

Preferably, the attribute is represented by a label of diagnosis result as having a prescribed psychiatric disorder; and the clustering is a process of classifying, by data-driven machine learning, the first cohort of subjects into clusters of at least one subtype.

Preferably, in generating an identifier by the machine learning, the processor performs the steps of i) dividing the adjusted values into a training dataset for machine learning and a test dataset for validation; ii) performing under-sampling and sub-sampling a prescribed number of times on the training dataset to generate the prescribed number of training sub-samples; iii) generating an identifier sub-model for each of the training sub-samples; and iv) integrating outputs of the identifier sub-models and generating an identifier model regarding presence/absence of the attribute.

Preferably, the process of generating an identifier by the machine learning is nested cross-validation having external cross-validation and internal cross-validation; in the nested cross-validation, the processor performs the steps of: i) dividing the adjusted values into a training dataset for machine learning and a test dataset for validation by conducting K-fold cross-validation as the external cross-validation; ii) performing under-sampling and sub-sampling a prescribed number of times on the training dataset to generate the prescribed number of training sub-samples; iii) in each loop of the K-fold cross-validation, adjusting hyperparameters by the internal cross-validation and thereby generating an identifier sub-model for each of the training sub-samples; and iv) generating an identifier model regarding presence/absence of the attribute based on the identifier sub-models.

Preferably, the process of generating an identifier by the machine learning is machine learning with feature selection; and in selecting a feature for the clustering, importance of a feature belonging to the sum set is determined by a ranking of frequency of the feature being selected when the identifier sub-model is selected.

Preferably, the process of generating an identifier by the machine learning is a random forest method; and in selecting a feature for the clustering, importance of a feature belonging to the sum set is an importance calculated in accordance with Gini impurity in the random forest method for each feature.

Preferably, the process of generating an identifier by the machine learning is machine learning by L2 regularization; and in selecting a feature for the clustering, importance of a feature belonging to the sum set is determined by a ranking based on feature weight in the identifier sub-model calculated by L2 regularization.

Preferably, the storage device stores in advance, for a plurality of traveling subjects as common objects of measurements across the plurality of measurement sites, results of measurements of brain activities of a predetermined plurality of brain regions of each of the traveling subjects; the processor performs, for each of the traveling subjects, the steps of calculating a prescribed component of a brain functional connectivity matrix representing time-wise correlation of brain activities of the plurality of pairs of brain regions; and by using Generalized Linear Mixed Model, for each prescribed component of the functional connectivity matrix, calculating the measurement bias as a fixed effect at each measurement site with respect to an average of the component over the plurality of measurement sites and the plurality of traveling subjects.

Preferably, the processor performs the process of classifying into the subtypes based on measurement data of a subject measured at a measurement site other than the plurality of measurement sites.

According to another aspect, the present invention provides a clustering system for clustering brain functional connectivity correlation values performing, based on measurement results of brain activities of objects, clustering of objects having at least one prescribed attribute among the objects, including a plurality of brain activity measuring devices provided respectively at a plurality of measurement sites, for time-sequentially measuring brain activities of a plurality of subjects including a first cohort of subjects having the prescribed attribute and a second cohort of subjects not having the prescribed attribute, and a computing system for performing a process of the clustering based on measured values of brain activities, on the plurality of subjects, the computing system including a storage device and a processor; wherein the processor is configured to perform the steps of i) storing, in the storage device, for each of the plurality of subjects, features based on a plurality of brain functional connectivity correlation values respectively representing time-wise correlation of brain activities between each of a prescribed plurality of pairs of brain regions, and ii) based on the features stored in the storage device, conducting supervised machine learning for generating an identifier model for discriminating presence/absence of the attribute; the processor performs, in the machine learning for generating an identifier model, the steps of generating a plurality of training sub-samples by performing under-sampling and sub-sampling from the first cohort of subjects and the second cohort of subjects, and selecting, for each of the training sub-samples, from a sum set of features used for generating the identifier by machine learning, features for clustering in accordance with importance of features belonging to the sum set; and the processor further performs the step of clustering the first cohort of subjects through multiple co-clustering of unsupervised learning, based on the selected features for clustering, and thereby generating a cluster classifier.

Preferably, the computing system receives, from a plurality of brain activity measuring devices provided respectively at a plurality of measurement sites, information representing time-wise correlation of brain activities between each of a prescribed plurality of pairs of brain regions of each of the plurality of subjects; and includes a harmonization calculating means for correcting the plurality of brain functional connectivity correlation values of each of the plurality of subjects to remove measurement bias of the measurement sites and thereby storing corrected adjusted values as the features in the storage device.

Preferably, the attribute is represented by a label of diagnosis result as having a prescribed psychiatric disorder; and the clustering is a process of classifying, by data-driven machine learning, the first cohort of subjects into clusters of at least one subtype.

According to a still further aspect, the present invention provides a clustering method of clustering brain functional connectivity correlation values allowing a computing system to perform, based on measurement results of brain activities of objects, clustering of objects having at least one prescribed attribute among the objects, wherein the computing system includes a storage device and a processor; the method including the steps of: the processor storing, in the storage device, for each of the plurality of subjects including a first cohort of subjects having the prescribed attribute and a second cohort of subjects not having the prescribed attribute, features based on brain functional connectivity correlation values representing time-wise correlation of brain activities between each of a prescribed plurality of pairs of brain regions, and based on the features stored in the storage device, the processor conducting supervised machine learning for generating an identifier model for discriminating presence/absence of the attribute; wherein the step of machine learning for generating an identifier model includes the steps of: generating a plurality of training sub-samples by performing under-sampling and sub-sampling from the first cohort of subjects and the second cohort of subjects, and selecting, for each of the training sub-samples, from a sum set of features used for generating the identifier by machine learning, features for clustering in accordance with importance of features belonging to the sum set; the method further including the step of: the processor clustering the first cohort of subjects through multiple co-clustering of unsupervised learning, based on the selected features for clustering, and thereby generating a cluster classifier.

According to a still another aspect, the present invention provides a classifier program for classifying brain functional connectivity correlation values, generated by a computing system performing, based on measurement results of brain activities of objects, clustering of objects having at least one prescribed attribute among the objects, allowing a computer to perform classifying of input data into clusters corresponding to the result of clustering, wherein the classifier program has a classifying function allowing the computer to classify into a cluster in which the input data has maximum posterior probability, based on a probability distribution model of each of the clusters; the computing system includes a storage device and a processor; and in the process of generating the classifier program based on the clustering, the computing system performs the steps of: the processor storing, in the storage device, for each of a plurality of subjects including a first cohort of subjects having the prescribed attribute and a second cohort of subjects not having the prescribed attribute, features based on brain functional connectivity correlation values representing time-wise correlation of brain activities between each of a prescribed plurality of pairs of brain regions, and based on the features stored in the storage device, the processor conducting supervised machine learning for generating an identifier model for discriminating presence/absence of the attribute; wherein the step of machine learning for generating an identifier model includes the steps of: generating a plurality of training sub-samples by performing under-sampling and sub-sampling from the first cohort of subjects and the second cohort of subjects, and selecting, for each of the training sub-samples, from a sum set of features used for generating the identifier by machine learning, features for clustering in accordance with importance of features belonging to the sum set; and the processor performs clustering of the first cohort of subjects through multiple co-clustering of unsupervised learning, based on the selected features for clustering, and thereby generates a cluster classifier.

Preferably, the computing system performs the steps of: receiving, from a plurality of brain activity measuring devices provided respectively at a plurality of measurement sites, information representing time-wise correlation of brain activities between each of a prescribed plurality of pairs of brain regions of each of a plurality of subjects; and conducting harmonization for correcting the plurality of brain functional connectivity correlation values of each of the plurality of subjects to remove measurement bias of the measurement sites and thereby storing corrected adjusted values as the features in the storage device.

Preferably, the attribute is represented by a label of diagnosis result as having a prescribed psychiatric disorder; and the clustering is a process of classifying, by data-driven machine learning, the first cohort of subjects into clusters of at least one subtype.

According to a still further aspect, the present invention provides a brain function marker classifying system, generated by a computing system performing, based on measurement results of brain activities of objects, clustering of objects having at least one prescribed attribute among the objects, allowing a computer to perform classifying of input data into clusters corresponding to the result of clustering, wherein the brain activity marker classifying system has a classifying function allowing the computer to classify into a cluster in which the input data has maximum posterior probability, based on a probability distribution model of each of the clusters; the computing system includes a storage device and a processor; and in the process of generating the brain activity marker classifying system based on the clustering, the computing system performs the steps of: the processor storing, in the storage device, for each of a plurality of subjects including a first cohort of subjects having the prescribed attribute and a second cohort of subjects not having the prescribed attribute, features based on a plurality of brain functional connectivity correlation values representing time-wise correlation of brain activities between each of a prescribed plurality of pairs of brain regions, and based on the features stored in the storage device, the processor conducting supervised machine learning for generating an identifier model for discriminating presence/absence of the attribute; wherein the step of machine learning for generating an identifier model includes the steps of: generating a plurality of training sub-samples by performing under-sampling and sub-sampling from the first cohort of subjects and the second cohort of subjects, and selecting, for each of the training sub-samples, from a sum set of features used for generating the identifier by machine learning, features for clustering in accordance with importance of features belonging to the sum set; and the processor performs clustering of the first cohort of subjects through multiple co-clustering of unsupervised learning, based on the selected features for clustering, and thereby generates a cluster classifier.

Preferably, the computing system performs the steps of receiving, from a plurality of brain activity measuring devices provided respectively at a plurality of measurement sites, information representing time-wise correlation of brain activities between each of a prescribed plurality of pairs of brain regions of each of the plurality of subjects; and conducting harmonization for correcting a plurality of brain functional connectivity correlation values representing time-wise correlation of the brain activities of each of the plurality of subjects to remove measurement bias of the measurement sites and thereby storing corrected adjusted values as the features in the storage device.

Preferably, the attribute is represented by a label of diagnosis result as having a prescribed psychiatric disorder; and the clustering is a process of classifying, by data-driven machine learning, the first cohort of subjects into clusters of at least one subtype.

According to a still further aspect, the present invention provides a clustering classifier model for clustering brain functional connectivity correlation values generated by a computing system performing, based on measurement results of brain activities of objects, clustering of objects having at least one prescribed attribute among the objects, allowing a computer to perform classifying of input data into clusters corresponding to the result of clustering, wherein for each of views obtained by partitioning a group of features characterizing the object included in training data, the clustering classifier model has a function of classifying the input data into a cluster in which the input data has maximum posterior probability, based on a value of probability density function calculated for the input data, based on information of the features included in each of the views and based on information specifying cluster-by-cluster probability density function of the object in each of the views; the computing system includes a storage device and a processor; and in the process of generating the clustering classifier model based on the clustering, the computing system performs the steps of: the processor storing, in the storage device, for each of a plurality of subjects including a first cohort of subjects having the prescribed attribute and a second cohort of subjects not having the prescribed attribute, features based on a plurality of brain functional connectivity correlation values representing time-wise correlation of brain activities between each of a prescribed plurality of pairs of brain regions, and based on the features stored in the storage device, the processor conducting supervised machine learning for generating an identifier model for discriminating presence/absence of the attribute; wherein the step of machine learning for generating an identifier model includes the steps of: generating a plurality of training sub-samples by performing under-sampling and sub-sampling from the first cohort of subjects and the second cohort of subjects, and selecting, for each of the training sub-samples, from a sum set of features used for generating the identifier by machine learning, features for clustering in accordance with importance of features belonging to the sum set; and the processor performs clustering of the first cohort of subjects through multiple co-clustering of unsupervised learning, based on the selected features for clustering, partitions the features to the views, and generates the cluster-by-cluster probability density function of the object in each of the views.

Advantageous Effects of Invention

By the present invention, regarding measurement data of brain activities measured at a plurality of facilities, it becomes possible to adjust and correct measurement bias at each of the facilities. Therefore, clustering becomes possible with brain functional connectivity correlation values adjusted, based on the measurement data obtained at a plurality of facilities.

Further, the present invention realizes a brain functional connectivity correlation value clustering device, brain functional connectivity correlation value clustering system, a brain functional connectivity correlation value clustering method, a brain functional connectivity correlation value classifier program and brain activity marker classification system that can harmonize measurement data of brain activities measured across a plurality of facilities and thereby objectively determine subtypes of diseases.

BRIEF DESCRIPTION OF DRAWINGS

FIG. 1 is a schematic diagram illustrating a harmonization process on data measured by the MRI measurement systems installed at a plurality of measurement sites.

FIG. 3A is a schematic illustration showing examples of "measurement parameters."

FIG. 3B is a schematic illustration showing examples of "subject attribute data."

FIG. 10 shows demographic characteristics of the training dataset (Dataset 1).

FIG. 11 shows demographic characteristics of the independent validation dataset (Dataset 2).

FIG. 12 shows the prediction performance (output probability distribution) of MDD on the training dataset for all imaging sites.

FIG. 13 shows the prediction performance (identifier output probability distribution) of the MDD on the training dataset for each imaging site.

FIG. 14 shows identifier output probability distributions of the MDD on the independent validation dataset.

FIG. 15 shows identifier output probability distributions of the MDD with respect to the independent validation dataset for each imaging site.

FIG. 21B is an illustration showing a concept of clustering when a plurality of objects is characterized by a plurality of features.

FIG. 23 is an illustration showing a concept in which probability models of different types of probability distributions are assumed in one view in "multiple co-clustering."

FIG. 26A shows Dataset 1 of a dataset divided into two.

FIG. 26B shows Dataset 2 of the dataset divided into two.

FIG. 27 is an illustration showing a concept of clustering performed on each dataset.

FIG. 31 illustrates methods of evaluating similarity of clustering (generalization performance of stratification).

FIG. 33A shows, in the form of a table, ARIs for respective views of Datasets 1 and 2.

FIG. 34 shows, in the form of a table, distribution of subjects allocated to respective clusters of View 1 in Clustering 1 and Clustering 1'.

FIG. 35 is an illustration showing a method of evaluating the site-to-site differences of the traveling subjects, who travel site-to-site to be subjected to measurements.

FIG. 36 is an illustration showing how to express the b-th functional connectivity of a subject a.

FIG. 40A shows contents of a multi-disease dataset of SRPBS.

FIG. 40B shows contents of a multi-disease dataset of SRPBS.

FIG. 40C shows contents of a multi-disease dataset of SRPBS.

FIG. 40D shows contents of a multi-disease dataset of SRPBS.

FIG. 41A shows imaging protocols at various measurement sites.

FIG. 41B shows imaging protocols at various measurement sites.

FIG. 41C shows imaging protocols at various measurement sites.

FIG. 41D shows imaging protocols at various measurement sites.

FIG. 48 illustrates a configuration of clustering classifier.

DESCRIPTION OF EMBODIMENTS

Figure 2A:
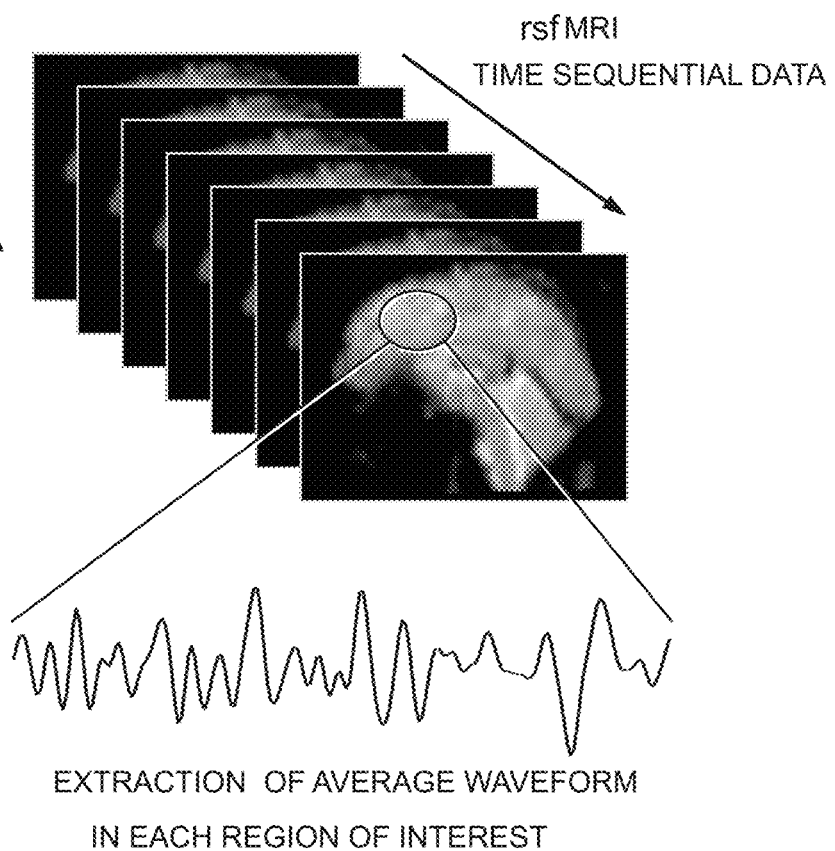
FIG. 2A is a schematic illustration showing a procedure for extracting a correlation matrix representing the correlation of functional connectivity in the resting state of Regions of Interest (ROIs) of a subject's brain, representing time-sequential data of rsfMRI.

In the following, for the description of the present invention directed to "the brain functional connectivity correlation value clustering device," "the brain functional connectivity correlation value clustering method" and so on, "clustering" by artificial intelligence technique on brain functional connectivity image data of subjects (including patients of mental disease/psychiatric disorders) measured by a measurement system including a plurality of brain functional connectivity measuring devices will be taken as an example.

In the following, a configuration of the measurement system, more specifically an MRI measurement system, in accordance with the embodiments of the present invention will be described with reference to the drawings. In the embodiments below, components or process steps denoted by the same reference characters are the same or corresponding components or steps and, therefore, descriptions thereof will not be repeated unless necessary.

In the following embodiments, the present invention is applied for time-sequentially measuring brain activities between a plurality of brain regions using "brain activity measuring devices" or, more specifically, "MRI measurement systems" installed at a plurality of facilities and for classifying subjects of a specific disorder into a plurality of groups (sub-groups) in a manner allowing generalization at a plurality of sites, based on time-correlation patterns (referred to as brain functional connectivity) of these regions.

Though not limiting, "major depressive disorder" will be taken as an example of the "specific disorder." As will be described in the following, however, the disease of subjects is not limited to "major depressive disorder", and it may be any other disorder or disease, as the present invention relates to a technique of classifying "brain functional connectivity correlation values" of subjects in a data-driven manner. Further, any attribute of subjects that can be classified in accordance with the patterns of "brain functional connectivity correlation" may be used, other than the disorder.

In such "MRI measurement systems," a plurality of "MRI devices" are installed at a plurality of different facilities and inherently involve the site-to-site differences in measurements (measurement facilities) including measurement bias derived from differences in measuring devices and differences between populations of subjects (sampling bias), which are independently evaluated as will be described later. Then, for each measurement of each measurement site, a process is applied for correcting the site-to-site differences by removing the effects of measurement biases. Thus, the process of harmonizing the measurement results among the measurement sites (harmonization) is realized. Description will be made assuming that brain functional connectivity values after harmonization are subjected to "feature selection" by ensemble learning using diagnosis labels of a specific disorder as teacher data, followed by clustering through unsupervised learning, so as to classify subjects' attributes (such as subtypes of psychiatric disorder).

First Embodiment

FIG. 1 is a schematic diagram illustrating a clustering (stratification) process of data measured by the MRI measurement systems installed at a plurality of measurement sites.

Referring to FIG. 1, it is assumed that MRI devices 100.1 to 100.$N_s$ are installed at measurement sites MS.1 to MS.$N_s$ ($N_s$: number of sites), respectively.

At measurement sites MS.1 to MS.$N_s$, measurements of subject cohorts PA.1 to PA.$N_s$ are taken. Each of the subject cohorts PA.1 to PA.$N_s$ includes at least two cohorts to be classified, for example, a patient cohort and a healthy cohort. Though not limiting, a patient cohort includes patients of mental disease and, more specifically, a cohort of "patients of major depressive disorder."

Further, it is assumed that at each measurement site, in principle, measurements of subjects are taken through measurement protocols as standardized as possible considering different specifications of MRI devices.

Though not specifically limited here, the measurement protocols define, by way of example, the following:

1) Direction of Scanning Subject's Head

It is necessary to prescribe whether the head scan is to be done in a direction from the back side (posterior: hereinafter denoted as "P") to the front side (anterior: hereinafter denoted as "A") (in the following, this direction will be referred to as "P→A direction") or the opposite direction, that is, from the front side to the back side (hereinafter referred to as "A→P direction"). Circumstances may require scanning in both directions.

Default scanning direction may differ from MRI device to device. In some devices, it is impossible to freely set or change the scanning direction.

The scanning direction possibly defines how an image is "distorted" and, hence, condition is set as a protocol.

2) Imaging Conditions for Brain Structural Images

Conditions are set for taking either "T1 weighted image" or "T2 weighted image" or both by a so-called spin echo.

3) Imaging Conditions for Brain Functional Images

Conditions are set for imaging brain functional images of subjects in the "resting state" by fMRI (functional Magnetic Resonance Imaging).

4) Imaging Conditions for Diffusion Weighted Images

Whether DWI (Diffusion (Weighted) Image) is to be obtained or not, and conditions therefor are set.

The diffusion weighted image is one type of MRI sequence, imaging diffusion of water molecules. In the spin echo pulse sequences usually used, signal attenuation caused by diffusion is negligible. When a large gradient magnetic field is continuously applied for a long time, however, phase shift caused by the movement of each magnetizing vector during that time becomes considerable and a region of more vigorous diffusion comes to appear as having lower signals. The diffusion weighted image utilizes this phenomenon.

5) Imaging for Correcting EPI Distortion by Image Processing

As a method of correcting EPI distortion by image processing, "field mapping" has been known and thus, conditions for imaging with respect to correction of spatial distortion are set.

In field mapping, EPI images are collected by multiple echo times, and based on these EPI images, the amount of EPI distortion is calculated. By applying the field mapping, it is possible to correct EPI distortion included in a new image. On the premise of a set of images of the same anatomical structure with different echo time, EPI distortion can be calculated and image distortion can be corrected.

For example, "field mapping" is described in Reference 1 below. The disclosure of Reference 1 is incorporated herein by reference in its entirety.

Reference 1: JP2015-112474 A

Measurement protocols may include excerpts of necessary sequence portions of the conditions described above, or may have other sequences or conditions added as needed.

Referring to FIG. 1 again, picking up subjects to be measured at respective measurement sites MS.1 to MS.$N_s$ will be referred to as "sampling," and the cause of the site-to-site differences of measurements resulting from the bias in the sampling at various measurement sites will be referred to as a "sampling bias."

In the example above, it is known that patients diagnosed as having "major depressive disorder" actually include several subtypes.

Typical subtypes include "melancholic," "atypical," "seasonal" and "postnatal" depressions. Depression in which "clinically meaningful improvement was not observed following the use of two different antidepressant and middle or severe symptoms continue" is referred to as "treatment resistant depression," and, according to a report, this type may account for 10% to 20% of depressions. Specifically, a patient cohort generally diagnosed as having major depression is known to be far from homogeneous. To date, methods of classifying such subtypes based on objective measurement data have not yet been practically successful.

At the measurement sites, the distribution of subtypes among patients having "major depressive disorder" is not always uniform due to various factors such as bias in nature caused by the locality of patients visiting hospitals of the measurement sites and the tendency of diagnosis at the hospitals. As a result, it is common that the subtype distribution among patients of the various measurement sites is biased, and hence, the "sampling bias" mentioned above arises.

Further, even in a group of subjects referred to as "healthy cohort," a plurality of subtypes exists in general, and in this point also, the "healthy cohort" also has a "sampling bias."

Further, as regards MRI devices 100.1 to 100.$N_s$, it is not always the case that MRI devices having the same measurement characteristics are used at respective measurement sites.

The site-to-site differences among measurement sites may be generated depending on the conditions of the MRI devices and the measurement conditions of the MRI devices, such as the manufacturers of the MRI devices, the model numbers of the MRI devices, the static magnetic field strength in the MRI devices, the number of coils (number of channels) of (transmitting) receiving coils of the MRI devices. Site-to-site differences resulting from such measurement conditions are referred to as "measurement biases."

Even MRI devices of the same model number manufactured by the same manufacturer do not always realize perfectly identical measurement characteristics, due to the inherent uniqueness of each device.

Here, as the (transmitting) receiving coil, generally, a "multi-array coil" is used in order to improve the signal-to-noise ratio of measured signals. The "number of receiving coils" means the number of "element coils" forming the multi-array coil.

By improving the sensitivity of each element coil and by bundling the outputs, the receiving sensitivity is improved.

In the present embodiment, though not limiting, it becomes possible to independently evaluate the "sampling bias" and the "measurement bias" by the harmonization method as will be described later.

Referring back to FIG. 1, measurement-related data DA100.1 to DA100.$N_s$ obtained from respective measurement sites MS.1 to MS.$N_s$ are accumulated and stored in a storage device 210 in a data center 200

Here, "measurement-related data" includes "measurement parameters" of respective measurement sites, as well as "patient cohort data" and "healthy cohort data" measured at respective measurement sites.

Further, "patient cohort data" and "healthy cohort data" include, for each subject, "patient MRI measurement data" and "healthy person MRI measurement data," respectively.

In the following, we will describe the "measurement-related data" as such.

Figure 2B:
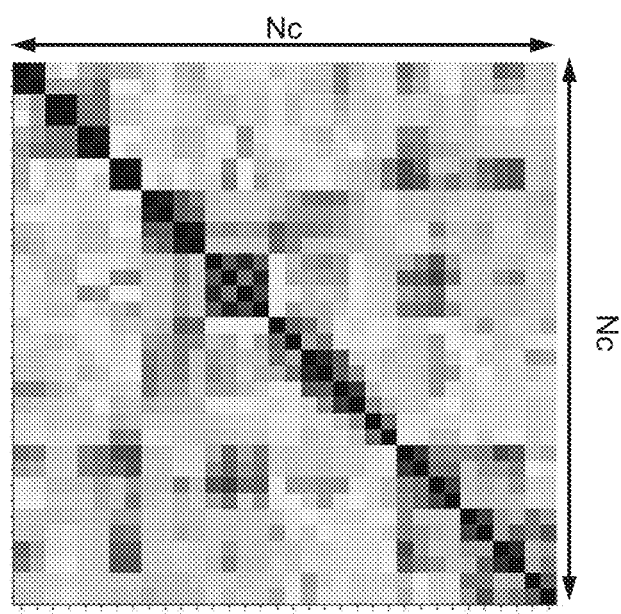
FIG. 2B is a schematic illustration showing a procedure for extracting a correlation matrix representing the correlation of functional connectivity in the resting state of ROIs of a subject's brain, representing a correlation matrix.

FIGS. 2A and 2B are schematic illustrations showing a procedure for extracting a correlation matrix representing the correlation of functional connectivity in a resting state of Regions of Interest of a subject's brain. FIG. 2A represents time-sequential data of rsfMRI, and FIG. 2B represents a correlation matrix thereof.

Here, referring to FIG. 1, the "patient MRI measurement data" and the "healthy person MRI measurement data" in the "patient cohort data" and the "healthy cohort data" include at least the following data.

i) Time-Sequential "Brain Function Image Data" for Calculating a Correlation Matrix Data and/or a Correlation Matrix Data Itself.

Specifically, when computing system 300 shown in FIG. 1 calculates the brain activity biomarker as will be described later based on data stored in storage device 210, the data mentioned above is used.

Here, the correlation matrix data may be calculated at each measurement site based on time-sequential "brain function image data," stored in storage device 210, and the computing system 300 may calculate the brain function biomarker based on the data of the correlation matrix stored in storage device 210.

Alternatively, time-sequential "brain function image data" may be stored in storage device 210, and computing system 300 may calculate the correlation matrix data stored in storage device 210 and may further calculate the brain activity biomarker.

Therefore, each of the "patient's MRI measurement data" and the "healthy person's MRI measurement data" at least includes either the time-sequential "brain function image data" for calculating the correlation matrix data, or the correlation matrix data itself.

ii) Subject's Structural Image Data and Diffusion Weighted Image Data

Though not specifically limited, the process for correcting EPI distortion may be done after the operation is done at each measurement site and the resulting data is stored in storage device 210.

Further, though not specifically limited, from the viewpoint of protecting personal information, before storing data in the storage device 210, an anonymization process may be performed at each measurement site. The anonymization process, however, may be performed by computing system 300 if the operator of computing system 300 is legally authorized to handle personal information.

Returning to FIGS. 2A and 2B, as shown in FIG. 2A, from fMRI data of n (n: a natural number) time points in the resting state measured on a real-time basis, an average "degree of activity" of each region of interest is calculated, and as shown in FIG. 2B, the correlation matrix of functional connectivity ("correlation value of activities") among the brain regions (among the regions of interest) are calculated. (Parcellation of Brain Regions)

Functional connectivity is calculated as the time-wise correlation of blood oxygen level dependent signal (BOLD) of the resting state functional MRI between two brain regions of each participant.

Here, as the regions of interest, we assume Nr regions as mentioned above and, hence, the number of independent non-diagonal components in the correlation matrix will be $Nr \times (Nr-1)/2$, considering the symmetry.

The regions of interest may be set by the following methods.

Method 1) "Regions of Interest are Defined Based on Anatomical Brain Areas."

Here, for the brain activity biomarker, 140 regions are picked up as regions of interest.

As for ROIs, in addition to 137 ROIs included in the Brain Sulci Atlas (BAL), the cerebellums (left and right) and the vermis of the Automated Anatomical Labeling Atlas are used. The functional connectivity (FC) among these 140 ROIs is used as features.

Here, the Brain Sulci Atlas (BAL) and the Automated Anatomical Labeling Atlas are disclosed in the following References 2 and 3. Disclosures of References 2 and 3 are incorporated herein by reference in their entirety.

Reference 2: Perrot et al., Med Image Anal, 15 (4), 2011

Reference 3: Tzourio-Mazoyer et al, Neuroimage, 15 (1), 2002

Such ROIs include, by way of example, the following:

Dorsomedial Prefrontal Cortex (DMPFC);
Ventromedial Prefrontal Cortex (VMPFC);
Anterior Cingulate Cortex (ACC);
Cerebellar Vermis;
Left Thalamus;
Right Inferior Parietal Lobe;
Right Caudate Nucleus;
Right Middle Occipital Lobe; and
Right Middle Cingulate Cortex.

It is noted, however, that the brain regions used may not be limited to those above.

For instance, the regions to be selected may be changed in accordance with the neurological/mental disorder to be studied.

Method 2) "Functional Connectivity is Defined Based on Brain Regions of a Functional Brain Map Covering the Entire Brain."

Here, the brain regions of such a functional brain map are disclosed in the references listed below and, though not limiting, configuration formed of 268 nodes (brain regions) may be adopted. Disclosures of References 4 to 7 below are incorporated herein by reference in their entirety.

Reference 4: Noble S, et al. Multisite reliability of MR-based functional connectivity. Neuroimage 146,959-970 (2017).

Reference 5: Finn E S, et al. Functional connectome fingerprinting: identifying individuals using patterns of brain connectivity. Nat Neurosci 18, 1664-1671 (2015).

Reference 6: Rosenberg M D, et al. A neuromarker of sustained attention from whole-brain functional connectivity. Nat Neurosci 19, 165-171 (2016).

Reference 7: Shen X, Tokoglu F, Papademetris X, Constable R T. Groupwise whole-brain parcellation from resting-state fMRI data for network node identification. Neuroimage 82, 403-415 (2013).

Method 3) Surface-Based Method

For parcellation of the brain regions, it is possible to analyze data by "surface-based method" based on a brain map prepared by converting the brain to sheets along cerebral sulcus, by using multimodal imaging of humane connectome project (HCP) style (myelin task functional).

For such parcellation, the toolbox disclosed at the site below may be used (ciftify toolbox version 2.0.2). https://edickie.github.io/ciftify/#/

This toolbox enables the analysis of used data (even when T2 enhanced images necessary for the HCP pipeline are lacking) in a surface-based pipeline similar to the HCP.

In the analysis according to Method 3, 379 surface-based areas (360 cortex areas+19 subcortical areas) disclosed in Reference 8 below are used as regions of interest (ROIs). The disclosure of Reference 8 is incorporated herein by reference in its entirety.

Reference 8: Glasser, M. F., Coalson, T. S., Robinson, E. C., Hacker, C. D., Harwell, J., Yacoub, E., et al. (2016). A multi-modal parcellation of human cerebral cortex. Nature 536(7615), 171-178. doi: 10.1038/nature18933.

Therefore, changes of BOLD signals over time are extracted from these 379 regions of interest (ROI).

Further, by the automatic anatomical labeling (AAL) as disclosed in Reference 9 below and by the use of Neurosynth (http://neurosynth.org/locations/), anatomical names of important ROIs and the names of intrinsic brain networks including the ROIs are specified. The disclosure of Reference 9 is incorporated herein by reference in its entirety.

Reference 9: Tzourio-Mazoyer, N., Landeau, B., Papathanassiou, D., Crivello, F., Etard, O., Delcroix, N., et al. (2002). Automated anatomical labeling of activations in SPM using a macroscopic anatomical parcellation of the MNI MRI single-subject brain. Neuroimage 15(1), 273-289. doi: 10.1006/nimg.2001.0978.

Method 4) Data-Driven Method of Determining Brain Regions

As disclosed in Reference 10 below, this is a method of newly identifying a network from in-phase voxels without previous knowledge (brain map), referred to as "Conical ICA" or "dictionary learning." The disclosure of Reference 10 is incorporated herein by reference in its entirety.

Reference 10: Kamalaker Dadi, Mehdi Rahim, Alexandre Abraham, Darya Chyzhyk, Michael Milham, Bertrand Thirion, Gael Varoquaux, "Benchmarking functional connectome-based predictive models for resting-state fMRI", Preprint submitted to NeuroImage, Oct. 31, 2018.

In the following, description will be made assuming that the method of defining functional connectivity based on the brain regions of the surface-based brain map basically in accordance with "Method 3" is used.

There are several candidates for measuring functional connectivity such as the tangent method and the partial correlation method as regards the calculation of correlation values.

In the following, however, we use Pearson's correlation coefficient, though it is not limiting.

For time-lapse of each of possible node sets of pre-processed BOLD signals, Pearson's correlation coefficient after Fisher z-transformation is calculated. The results are used for forming a 379×379 symmetrical connectivity matrix, each element of which represents the strength of connectivity between two nodes.

FIGS. 3A and 3B show examples of "measurement parameters" and "subject attribute data."

It is assumed that "subject attribute data" is stored associated with the "patient's MRI measurement data" and the "healthy person's MRI measurement data," respectively, in the "patient cohort data" and the "healthy cohort data" of FIG. 1.

As shown in FIG. 3A, the examples include a site ID for identifying the measurement site, a site name, a condition ID for identifying the measurement parameters, information related to the measuring device, and information related to the measurement conditions.

The "measurement parameters" include "information related to the measuring device" and "information related to measurement conditions."

The "information related to the measuring device" includes the name of the manufacturer, the model number and the number of (transmitting) receiving coils of the MRI device for measuring brain activities of subjects at each measurement site.

The "information related to the measuring device" is not limited to these, and it may include static magnetic field strength, uniformity of magnetic field after shimming and other indexes indicating performance of the measuring device.

The "information related to measurement conditions" includes the direction of phase encoding when an image is re-constructed (P→A or A→P), type of image (T1 weighted, T2 weighted, diffusion weighted etc.), imaging sequence (spin echo etc.), whether the subject's eyes are open/closed during imaging and so on.

The "information related to measurement conditions" is not limited to these, either.

Referring to FIG. 3B, the "subject attribute data" includes the subject's tentative ID as a pseudonym to prevent identification of the subject, condition ID indicating the measurement conditions when the subject was measured, and the attribute information of the subject.

The "subject attribute information" includes sex and age of the subject, a label indicating either healthy or sick, the disease name of the subject as diagnosed by a doctor, medication profile, diagnosis history and so on.

The "subject attribute information" may be anonymized as needed at, for example, the measurement site.

By way of example, as to the age and sex, the subject's attribute information may be processed to maintain "k-anonymity" that reduces the probability of identifying an individual to 1/k or smaller by transforming data such that at least k data of "quasi-identifier" (same attribute) exist. Here, "quasi-identifier" refers to an identifier such as "age," "sex," and "place of residence" that cannot identify an individual by itself but allows identification of an individual when combined.

Mediation profile and diagnosis history may be subjected to anonymization as needed, by randomizing or shifting (relativizing) the dates.

In the following, in the "patient's MRI measurement data" and the "healthy person's MRI measurement data," the functional connectivity calculated as the correlation of temporal activities between each of the brain areas of each subject will be generally referred to as "functional connectivity" (or "FC" for short) between each brain area. If it is necessary to distinguish one functional connectivity from another, a suffix will be added, as will be described later.

(Configuration of MRI Device)

Figure 4:
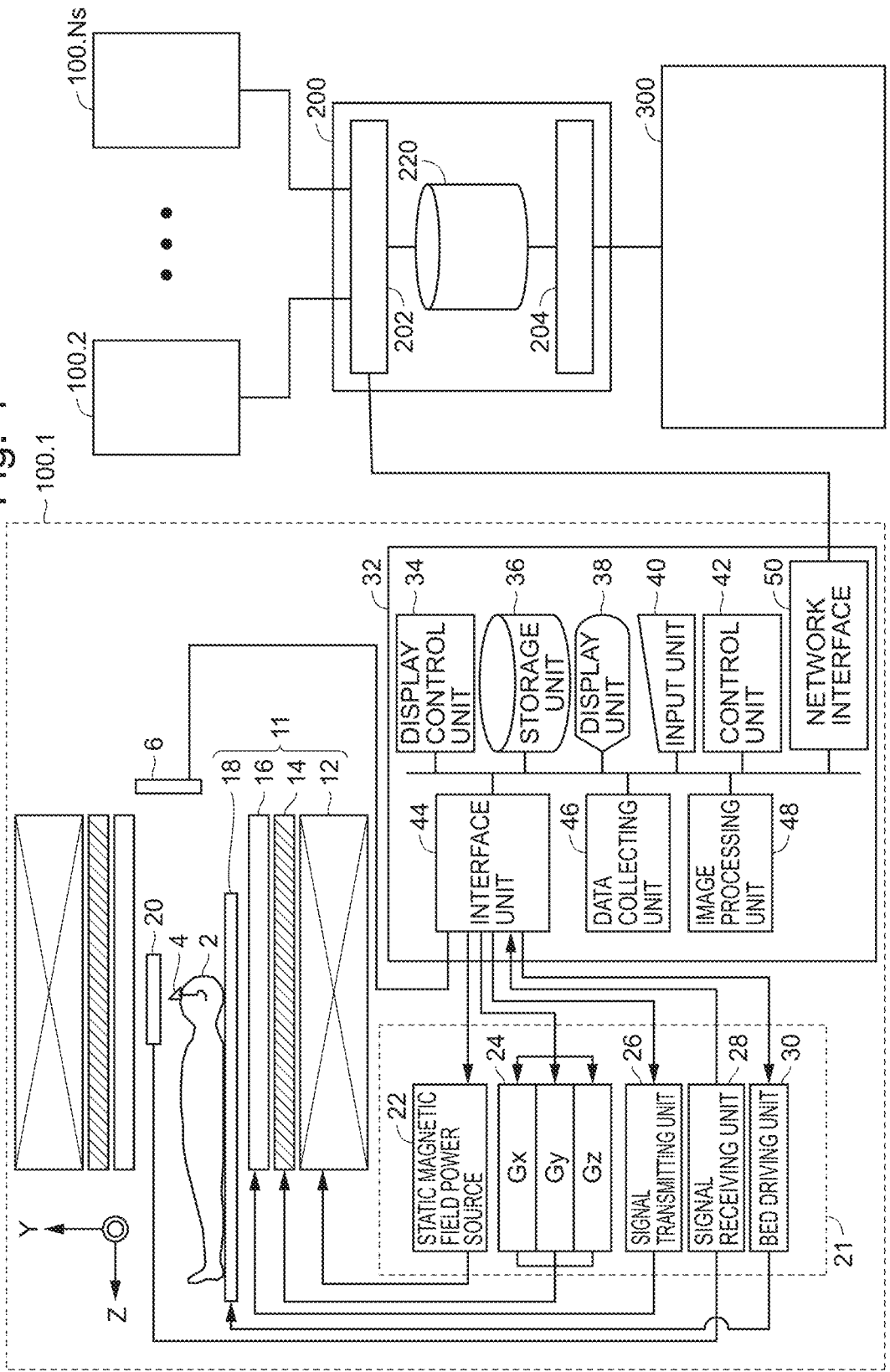
FIG. 4 is a schematic diagram showing an overall configuration of an MRI device $100.i$ ($1 \leq i \leq N_s$) installed at respective measurement sites.

FIG. 4 is a schematic diagram showing an overall configuration of an MRI device 100.$i$ ($1 \le i \le N_s$) installed at respective measurement sites.

In FIG. 4, MRI device 100.1 at the first measurement site is shown in detail as an example. Other MRI devices 100.2 to 100.$N_s$ also have similar basic configurations.

As shown in FIG. 4, MRI device 100.1 includes: a magnetic field applying mechanism 11 for applying a controlled magnetic field to, and irradiating with RF wave, a region of interest of a subject 2; a receiving coil 20 for receiving a response wave (NMR signal) from subject 2 and outputting an analog signal; a driving unit 21 for controlling the magnetic field applied to subject 2 and controlling the transmission/reception of RF wave; and a data processing unit 32 for configuring a control sequence of driving unit 21 and processing various data signals to generate an image.

Here, the central axis of a cylindrical bore in which subject 2 is placed is regarded as a Z-axis, and a horizontal direction orthogonal to the Z-axis and the vertical direction orthogonal to the Z-axis are defined as X-axis and Y-axis, respectively.

In MRI device 100.1 having such a configuration, because of the static magnetic field applied by magnetic field applying mechanism 11, nuclear spins of atomic nuclei forming subject 2 are oriented in the direction of magnetic field (Z-axis) and precess about the direction of magnetic field, with the Larmor frequency unique to the atomic nuclei.

When irradiated with an RF pulse of the same Larmor frequency, the atoms resonate, absorb energy and are excited, resulting in nuclear magnetic resonance (NMR). When the irradiation with RF pulse is stopped after the resonance, the atoms discharge energy and return to the original, steady state. This process is referred to as a relaxation process. In the relaxation process, the atoms output electromagnetic wave (NMR signal) having the same frequency as the Larmor frequency.

The output NMR signal is received by receiving coil 20 as a response wave from subject 2, and the regions of interest of subject 2 are imaged by data processing unit 32.

Magnetic field applying mechanism 11 includes a static magnetic field generating coil 12, a magnetic field gradient generating coil 14, an RF irradiating unit 16, and a bed 18 for placing subject 2 in the bore.

By way of example, subject 2 lies on his/her back on bed 18. Though not limiting, subject 2 may view an image displayed on a display 6 mounted perpendicular to the Z-axis, using prism glasses 4. Visual stimulus may be applied to subject 2 by an image on display 6 as needed. Alternatively, visual stimulus to subject 2 may be applied by projecting an image in front of subject 2 using a projector.

Such a visual stimulus corresponds to the presentation of feedback information in the above-described neurofeedback.

Driving unit 21 includes a static magnetic field power source 22, a magnetic field gradient power source 24, a signal transmitting unit 26, a signal receiving unit 28, and a bed driving unit 30 for moving bed 18 to any position along the Z-axis.

Data processing unit 32 includes: an input unit 40 for receiving various operations and information input from an operator (not shown); a display unit 38 for displaying various images and various pieces of information related to the regions of interest of subject 2; a display control unit 34 controlling display by display unit 34; a storage unit 36 for storing programs, control parameters, image data (structural images and the like) and other electronic data to cause execution of various processes; a control unit 42 for controlling operations of various functional units, including generating a control sequence for driving the driving unit 21; an interface unit 44 for performing transmission/reception of various signals to/from driving unit 21; a data collecting unit 46 for collecting data consisting of a group of NMR signals derived from the regions of interest; an image processing unit 48 for forming an image based on the data of NMR signals; and a network interface 50 for performing communication with a network.

Data processing unit 32 may be a dedicated computer, or it may be a general-purpose computer programmed to perform functions causing operations of various functional units, in which designated operations, data processing and generation of control sequence may be realized by a program or programs stored in storage unit 36. In the following, description will be given assuming that data processing unit 32 is implemented by a general-purpose computer.

Static magnetic field generating coil 12 causes a current supplied from a static magnetic field power source 22 to flow through a helical coil wound around the Z-axis to generate an induction magnetic field, and thereby generates a static magnetic field in the Z-direction in the bore. The regions of interest of subject 2 are placed in the region of highly uniform static magnetic field formed in the bore. More specifically, here, static magnetic field coil 12 is comprised of four air core coils, forms a uniform magnetic field inside by the combination of the coils, and attains orientation of the spins of prescribed atomic nuclei in the body of subject 2, or more specifically, the spins of hydrogen atomic nuclei.

Magnetic field gradient generating coil 14 is formed of X-, Y- and Z-coils (not shown), and provided on an inner peripheral surface of cylindrical static magnetic field generating coil 12.

In order to improve uniformity of magnetic field gradient, a shim coil (not shown) is used and "shimming" is performed.

These X-, Y- and Z-coils superpose magnetic field gradients on the uniform magnetic field in the bore with the X-axis, Y-axis and Z-axis directions switched in turn, whereby creating intensity gradient in the static magnetic field. When excited, the Z-coil tilts the magnetic field intensity to the Z-direction and thereby defines a resonance surface; the Y-coil applies a tilt for a short period of time immediately after application of the magnetic field in the Z-direction, and thereby adds phase modulation in proportion to the Y-coordinate, to the detected signal (phase encoding); and thereafter the X-coil applies a tilt when data is collected, and thereby adds frequency modulation in proportion to the X-coordinate, to the detected signal (frequency encoding).

The switching of superposed magnetic field gradients is realized as different pulse signals are output to the X-, Y- and Z-coils from the magnetic field gradient power source in accordance with a control sequence. Thus, the position of subject 2 expressed by the NMR can be specified, and positional information in three-dimensional coordinates necessary to form an image of subject 2 are provided.

Here, using the orthogonally crossing three sets of magnetic field gradients, allocating slice direction, phase encoding direction and frequency encoding direction to the magnetic fields respectively, as described above, and by combining these, images can be taken from various angles. By way of example, in addition to transverse slice in the same direction as taken by an X-ray CT apparatus, sagittal and coronal slices orthogonal thereto, as well as an oblique slice, of which direction perpendicular to its plane is not parallel to any of the axes of three orthogonally crossing magnetic field gradients, can be imaged.

RF irradiating unit 16 irradiates regions of interest of subject 2 with RF (Radio Frequency) pulses based on a high-frequency signal transmitted from a signal transmitting unit 26 in accordance with a control sequence.

Though RF irradiating unit 16 is built in magnetic field applying mechanism 11 in FIG. 1, it may be mounted on bed 18 or integrated with receiving coil 20 as a transmitting/receiving coil.

Receiving coil 20 detects a response wave (NMR signal) from subject 2, and in order to detect the NMR signal with high sensitivity, it is arranged close to subject 2.

Here, when an electromagnetic wave of NMR signal crosses a coil strand of receiving coil 20, a weak current is generated by electromagnetic induction. The weak current is amplified by signal receiving unit 28 and converted from an analog signal to a digital signal, and then transmitted to data processing unit 32.

As the (transmitting) receiving coil 20, a multi-array coil is used for improving the SN ratio, as described above.

The mechanism here is as follows. To a subject 2 in a state of static magnetic field with Z-axis magnetic field gradient added, a high-frequency electromagnetic field of resonance frequency is applied through RF irradiating unit 16. Prescribed atomic nuclei, for example, hydrogen atomic nuclei, at a portion where magnetic field intensity satisfies the condition of resonance are selectively excited and start resonating.

Prescribed atomic nuclei at a portion satisfying the condition of resonance (for example, a slice of prescribed thickness of subject 2) are excited, and (in a classic image drawing) spin axes concurrently start rotation. When the excitation pulse is stopped, electromagnetic waves irradiated by the spin axes in rotation induce a signal in receiving coil 20 and, for some time, this signal is continuously detected. By this signal, a tissue containing the prescribed atoms in the body of subject 2 is monitored. In order to know the position where the signal comes from, X- and Y-magnetic field gradients are added and the signal is detected.

Based on the data built in storage unit 36, image processing unit 48 measures detected signals while repeatedly applying excitation signals, reduces resonance frequency to X-coordinate by a first Fourier transform to obtain an image, restores Y-coordinate by a second Fourier transform, and thus, displays the corresponding image on display unit 38.

For example, by picking-up the BOLD signal on a real-time basis using the MRI system as described above and performing an analysis, which will be described later, on the time-sequentially picked-up images by control unit 42, it is possible to take images of the resting-state functional connectivity MRI (rs-fcMRI).

In FIG. 4, measurement data, measurement parameters and subject attribute data from MRI device 100.1 as well as from MRI devices 100.2 to 100.N$_s$ at other measurement sites are accumulated and stored in storage device 210 through a communication interface 202 in data center 200. Further, computing system 300 is configured to access data in storage device 210 through communication interface 204.

Figure 5:
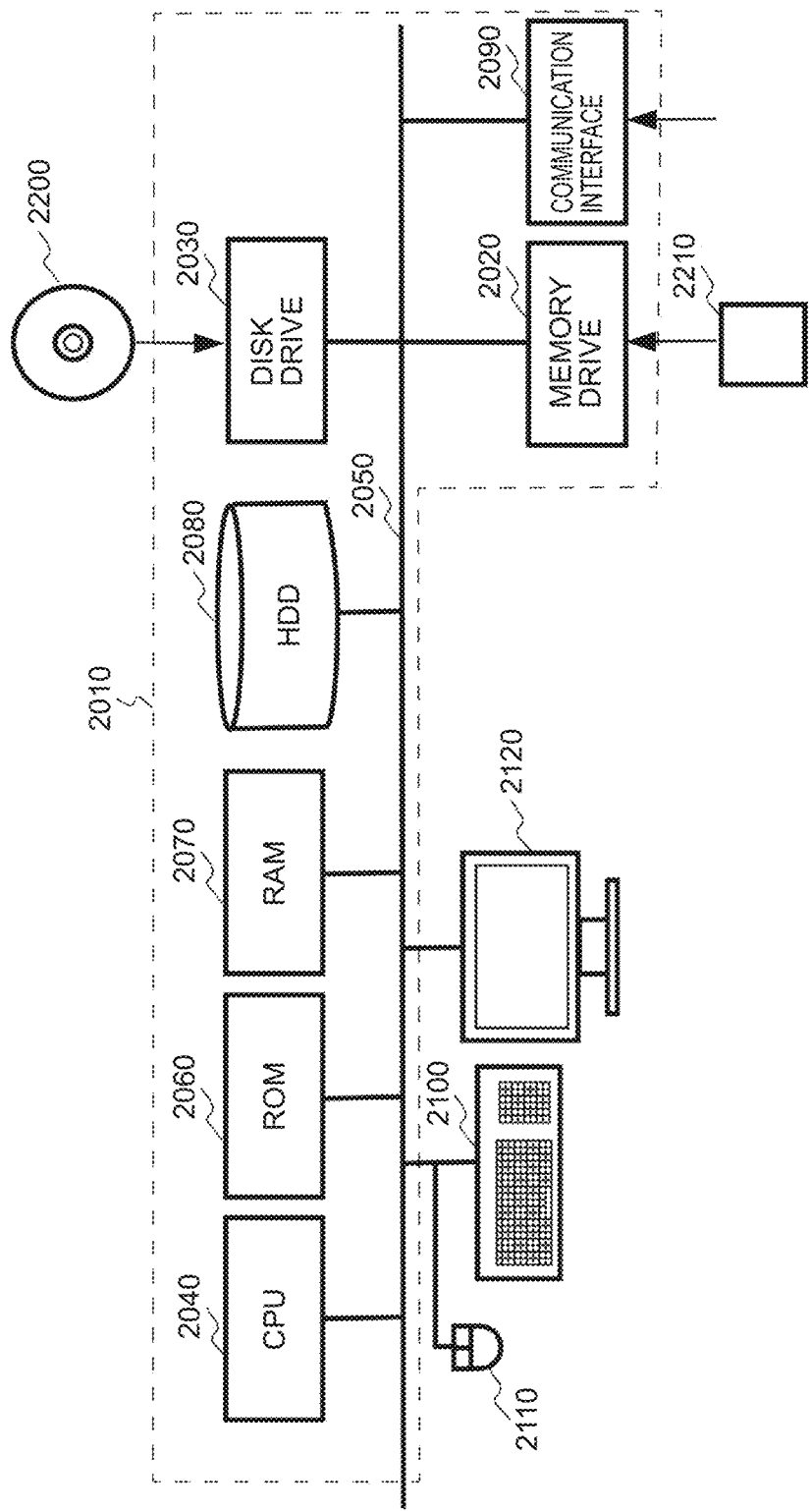
FIG. 5 is a hardware block diagram of a data processing unit 32.

FIG. 5 is a hardware block diagram of data processing unit 32.

Though the hardware of data processing unit 32 is not specifically limited as described above, a general-purpose computer may be used.

Referring to FIG. 5, a computer main body 2010 of data processing unit 32 includes, in addition to a memory drive 2020 and a disk drive 2030, a processor 2040, a bus 2050 connected to disk drive 2030 and memory drive 2020, an ROM 2060 for storing programs such as a boot-up program, an RAM 2070 for temporarily storing instructions of an application program and providing a temporary memory space, a non-volatile storage device 2080 for storing application programs, system programs and data, and a communication interface 2090. Communication interface 2090 corresponds to an interface unit 44 for transmitting/receiving signals to/from driving unit 21 and the like and a network interface 50 for communicating with another computer through a network, not shown. As non-volatile storage device 2080, a hard disk (HDD), a solid-state drive (SSD) or the like may be used. Non-volatile storage device 2080 corresponds to storage unit 36.

By operation processes performed by processor 2040 in accordance with a program, various functions of data processing unit 32 including, for example, functions of control unit 42, data collecting unit 46 and image processing unit 48 are realized.

A program or programs causing data processing unit 32 to perform the functions of the present embodiment as described above may be stored in a CD-ROM 2200 or a memory medium 2210 and inserted to disk drive 2030 or memory drive 2020 and may be further transferred to non-volatile storage device 2080. The program or programs will be loaded to RAM 2070 when to be performed.

Data processing unit 32 further includes a keyboard 2100 and a mouse 2110 as input devices, and a display 2120 as an output device. Keyboard 2100 and mouse 2110 correspond to input unit 40 and display 2120 corresponds to display unit 38.

The program or programs realizing the functions as data processing unit 32 as described above may not necessarily include an operating system (OS) for performing the functions of information processing apparatus such as computer main body 2010. The program or programs may only include those portions of instructions which can call appropriate functions (modules) in a controlled manner to attain a desired result. The manner how data processing unit 32 operates is well known and, therefore, detailed description will not be given here.

Further, the above-described program or programs may be performed by one computer or by a plurality of computers. In other words, both centralized processing and distributed processing are possible.

Hardware of computing system 300 has basically the same configuration as that shown in FIG. 5, though there may be some difference such as use of parallel processing units or use of GPGPU (General-Purpose computing on graphic processing units).

(Diseased/Healthy Discriminator Generating Process and Clustering Process Based on Brain Functional Connectivity)

Figure 6:
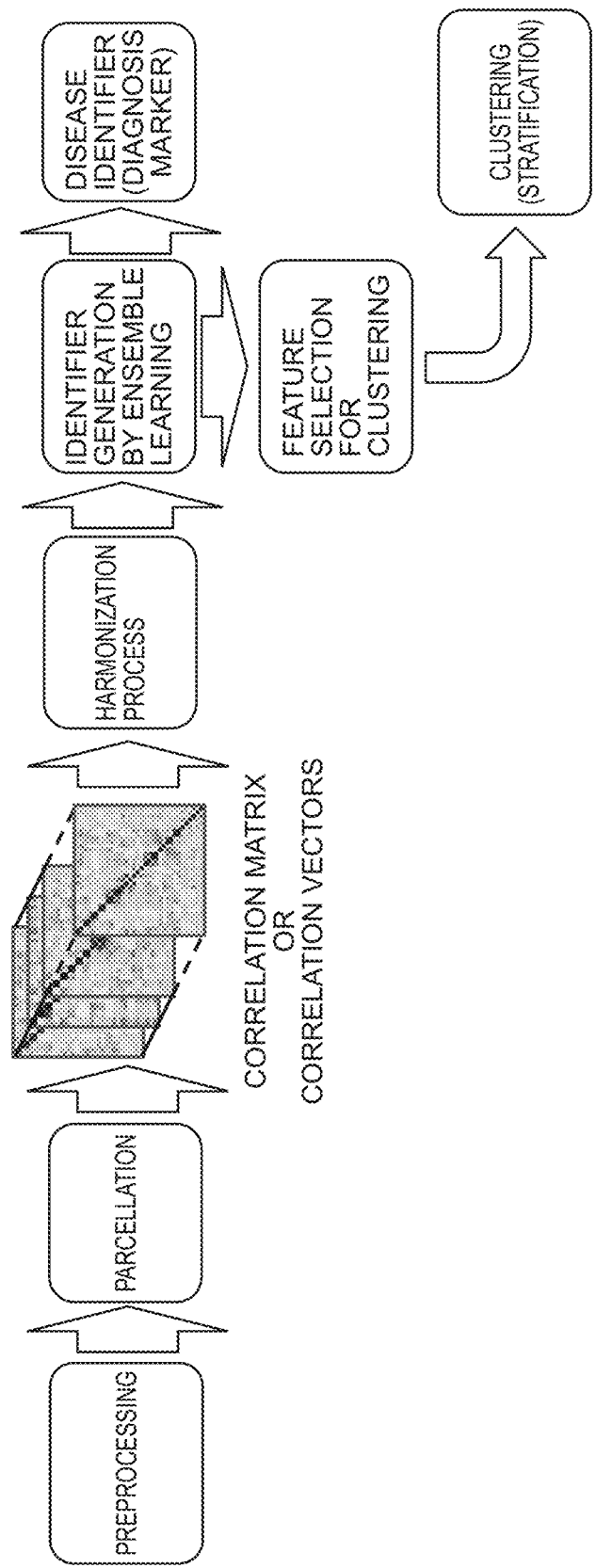
FIG. 6 is an illustration showing a process of generating a discriminator to serve as a diagnostic marker from correlation matrixes and a clustering process.

FIG. 6 is an illustration showing a process of generating a discriminator to serve as a diagnostic biomarker from correlation matrixes as described with reference to FIG. 2B and a clustering process.

Regarding machine learning, generation of a discriminator involves a so-called "supervised learning" process, and clustering involves "unsupervised learning."

The clustering process itself is realized by "unsupervised learning" and it does not use diagnostic information of medical doctors. Therefore, each of the resulting clusters represent a group of patients obtained in data-driven manner. If the patients are divided to subtypes, the results serve as a basis for "stratification of patients" having brain functional connectivity as a feature.

As shown in FIG. 6, first, by a plurality of MRI devices, fMRI image data in the resting state of healthy cohorts and patient cohorts are taken, and computing system 300 performs "pre-processing" as described below on the fMRI data thus obtained. Thereafter, from the measured data of functional connectivity MRI data in the resting state, computing system 300 performs parcellation of brain regions of each subject, and derives correlation matrix of activities between brain regions (regions of interest).

Then, for non-diagonal components of the correlation matrix, corresponding measurement bias is derived as described later. The computing system 300 subtracts the measurement bias from component values of the correlation matrix and, thus, realizes harmonization.

Further, between the harmonized component values of correlation matrix and the disease label of each subject (label indicating sick or healthy), computing system 300 performs generation of an identifier with feature selection while preventing overtraining as "identifier generating process through ensemble learning" as will be described later. Thus, a disease identifier (diagnosis marker) capable of predicting whether a subject is healthy or has a disease is generated.

On the other hand, during the ensemble learning, computing system 300 performs feature selection for clustering as will be described later from the features (brain functional connectivity) specified in the process of generating the identifier and then, performs multiple co-clustering by "unsupervised learning."

In the following, each of the processes shown in FIG. 6 will be described in greater detail.

[Outline of Preprocessing, Generation of Disease Identification and Clustering]

(Preprocessing and Calculation of Resting State Functional Connectivity FC Matrix)

The first 10 seconds of measured fMRI data are discarded to take the T1 equilibrium into consideration.

At the preprocessing step, the computing system 300 performs the calibration of slice timing, the re-alignment process for correcting body motion artifacts observed at one's head, co-registration of the brain functional image (EPI image) and the structural image, the distortion correction, segmentation of the T1 enhanced structural image, the normalization to the MNI (Montreal Neurological Institute) space, and spatial smoothing using the isotropic Gaussian kernel of 6 mm full-width at half maximum.

The above-described pipeline pre-processing is disclosed, for example, at the site below.

http://fmriprep.readthedocs.io/en/latest/workflows.html (Parcellation of Brain Regions)

For parcellation of the brain regions, though not limiting, the "surface-based method" in accordance with "Method 3" described above may be utilized.

(Physiological Noise Regression)

Physiological noise regression is performed by applying the CompCor disclosed in Reference 11 below. The disclosure of Reference 11 is incorporated herein by reference in its entirety.

Reference 11: Behzadi, Y., Restom, K., Liau, J., and Liu, T. T. (2007). A component based noise correction method (CompCor) for BOLD and perfusion based fMRI. Neuroimage 37(1), 90-101. doi: 10.1016/j.neuroimage.2007.04.042.

In order to remove some sources of spurious (undesirable signal sources), the linear regression with regression parameters such as six kinematic parameters, whole brain etc. is used.

(Temporal Filtering)

Computing system 300 applies a temporal bandpass filter to the time-sequential data using Butterworth filter having pass bands between 0.01 Hz and 0.08 Hz, so that the analysis is limited to low-frequency fluctuation characteristic to the BOLD behavior.

(Head Movement)

In each functional session, frame-wise displacement (FD) is calculated, and in order to reduce variation in spurious of the functional connectivity FC caused by head movement, any volume having FD>0.5 mm is removed.

FD represents head movement between two temporally continuous volumes as a scalar quantity (that is, the sum of absolute displacements in translation and rotation).

In a specific example described later, in the specific dataset as mentioned above, if the ratio of volume removed after scrubbing exceeds (average±3 standard deviation), the data of the corresponding participant is excluded from the analysis. As a result, for the whole dataset, thirty-five participants were excluded. Hence, of the training dataset, 683 participants (545 HCs and 138 MDD) were used, and of the independent validation dataset, the data of 444 participants (263 HCs, 181 patients of MDD) was used for the analysis below.

(Calculation of Functional Connectivity (FC) Matrix)

In a specific example in accordance with the present embodiment, after the regions are divided by the above-described parcellation, the functional connectivity FC is calculated as a temporal correlation of the BOLD signals over 379 regions of interest (ROIs) for each participant.

Though not limiting, for calculating functional connectivity, here again, the Pearson's correlation coefficient is used.

The Pearson's correlation coefficient subjected to Fisher z-transformation of pre-processed BOLD signals over time of each possible set of ROIs is calculated, and a symmetrical connectivity matrix of 379 rows×379 columns, of which components each represent the strength of connection between two ROIs, is formed.

Further, for reasons of analysis, the values of the functional connectivity of the lower triangular matrix of 71,631 (=(379×378)/2) of the connectivity matrix are used.

(Harmonization of Brain Activity Biomarkers)

When big data associated with mental diseases or psychiatric disorders is to be collected, it is nearly impossible, as is stated above, to collect massive brain image data (connectomes related to human disease) at one site. Therefore, it is necessary to acquire image data from a plurality of sites.

It is difficult to regulate types of MRI devices (scanners), protocols and patient segments. Therefore, in most cases, when analyzing collected data, brain image data picked up under different conditions are used.

Particularly, disease factors tend to be confounded with site factors and, therefore, when disease factors are to be extracted by applying machine learning to data obtained under different conditions, the site-to-site differences poses the biggest barrier.

One site (or a hospital) tends to sample only a few types of mental diseases (for example, mainly schizophrenia at site A, mainly autism at site B and mainly major depressive disorder at site C), leading to confounding.

In order to regulate data under different conditions appropriately, the harmonization of the site-to-site data is indispensable.

The site-to-site differences essentially include two types of biases. Specifically, a technical bias (or measurement bias) and a biological bias (or sampling bias).

The measurement bias involves differences in imaging parameters, electric field strength, and the characteristics of MRI scanners such as the MRI manufacturers and the scanner models. The sampling bias relates to differences of subject cohorts from one site to another.

Hence, "harmonization" to compensate for such site-to-site difference becomes necessary. Details of harmonization are described in Non-Patent Literature 8 (Ayumu Yamashita et al.) listed above, of which contents will be discussed later.

(Disease Identifiers Based on Ensemble Learning)

In the present specification, the "ensemble learning" refers to a process of preparing K-sets of training data by sampling with replacement from original training data, generating K identifiers independently for respective training data through machine learning, integrating these K identifiers and thereby generating a discriminator.

It is noted that the object here is to determine whether a subject is healthy or has a disease based on brain functional connectivity patterns of the subject. Therefore, each identifier will be an identifier that serves to solve the problem of identifying two classes.

When K-sets of training data are to be prepared by sampling with replacement from original training data, "under sampling" and "sub-sampling" are performed, as will be described later.

Here, "identifier realized through learning with feature selection" such as logistics regression analysis using LASSO (least absolute shrinkage and selection operator) by L1 regularization, or regularization learning such as Ridge regularization (L2 regularization) may be applicable.

Here, "regularization learning" refers to a method of learning that, while using all the features of original training data, assigns a penalty, in a learning algorithm, to increased model complexity during learning, and determines the training model having the minimum sum of training error and the penalty, thereby improving generalization performance. L1 regularization uses sum of absolute values of training model parameters (corresponding to the features) as the penalty, while L2 regularization uses sum of squares of training model parameters as the penalty. L0 regularization is also possible, in which the number of features themselves used for the model is used as the penalty.

Further, LASSO method (L1 regularization) allows for a so-called sparse estimation, and its derivatives include Elastic Net method, Group Lasso method, Fused Lasso method, Adaptive Lasso method and Graphical Lasso method.

On the other hand, as the "identifier trained with feature selection," it is possible to use a method such as "random forest method" which not only selects features but also specifies their respective importance in generating an identifier.

Hereafter, description will be made in the following mainly taking LASSO method as an example of "identifier generating process through ensemble learning". It is noted, however, that the method is not limited to those described above. By way of example, the parcellation method may be such an ensemble learning wherein Dictionary Learning method is used in configuring brain regions as the object of analysis in a data-dependent manner, tangent-space covariance is used as values of functional brain connectivity, ComBat method, which will be described later, is used in realizing facility-to-facility correction of brain functional connectivity FC in a dataset, and Ridge regularization is used to generate an identifier. Other combinations may be adopted as the parcellation method, the method of calculating brain functional connectivity, the harmonization method and the method of generating an identifier. For example, distance correlation may be used as the method of calculating brain functional connectivity. Here, "distance correlation" is a method of calculating similarity of activity patterns without averaging activity patterns in brain regions, unlike Pearson's correlation method. This method is disclosed in References 12 and 13. The disclosures of References 12 and 13 are incorporated herein by reference in its entirety.

Reference 12: G. J. Szekely, M. L. Rizzo, N. K. Bakirov, Measuring and testing independence by correlation of distances, Ann. Statist., 35 (6) (2007), pp. 2769-2794

Reference 13: https://en.wikipedia.org/wiki/Distance_correlation

As will be described later, in the present embodiment, the ensemble training specifies the "importance" of each feature for achieving the function of identification during the identifier training.

(Feature Selection for Clustering and Clustering)

In the process of generating K identifiers by the "ensemble learning" for the K-sets of training data, a process is performed for specifying, from a sum set of "first features" used in generating each identifier, the second set of features for performing clustering through "unsupervised learning."

Particularly, though not limiting, the "importance" is determined in the following manner.

i) If the method of learning for generating K identifiers in the ensemble learning is "learning with feature selection," in the sum set of "first features" selected for generating the identifiers, features are ranked in accordance with the frequency of use for generating K identifiers.

ii) If the method of learning for generating K identifiers in the ensemble learning is a method in which importance of features can be obtained during the generation of identifiers, such as in the case of "random forest method," the importance thus generated may be used.

iii) If the method of learning for generating K identifiers in the ensemble learning is "Ridge regularization (L2 regularization)" (that does not necessarily involve feature selection) using weighted sum of features as an argument, absolute values of weight coefficients of features in each identifier are summed up for K identifiers, and the median of the sum is used as the importance and the features are ranked and listed. The importance is not necessarily limited to the "median" and any other representative value, such as "integrated value obtained by integrating K identifiers" may be used.

It is possible to use a prescribed number of upper-ranked features in the list generated in accordance with the methods i) to iii) as the "second feature."

The condition for specifying the "second feature" is not limited to the prescribed number from the top of the ranking list. For example, a feature that has a prescribed frequency or higher in the ranking list (the fact that in generating K identifiers, the feature is selected at a certain rate or higher) may be used as a condition.

As described above, based on the selected feature(s), clustering (stratification of patients) is performed through "multiple co-clustering," which is an unsupervised learning.

(Process for Generating Identifier for Classifying Two Classes)

In the following, among the processes described with reference to FIG. 6, generation of an identifier through ensemble learning will be described in greater detail.

Specifically, the process for generating a classifier for classifying two classes, or more specifically, a process of forming a biomarker for MDD using training dataset as the training data for a disease identifier (two-class classifier for "healthy" and "sick") will be described.

Here, the process of generating a classifier will be described concerning major depressive disorders as an example among mental diseases or psychiatric disorders, i.e., concerning a group of patients diagnosed as having major depressive disorder by doctors in accordance with the conventional method of symptom-based diagnosis approach. Then, an example will be given in the following concerning the process performed by the disease identifier generator 3008 shown in FIG. 8 to generate a classifier that outputs assisting information for discriminating a patient cohort from a healthy cohort.

In the following, we will describe a procedure of building an MDD identifier for identifying a healthy control (HC) and a MDD patient based on the functional connectivity FC.

In the following, as the "identifier realized through learning with feature selection" for forming a disease identifier (MDD identifier), the method of training an identifier by L1 regularization (LASSO method) will be described as an example.

As will be described later, in order to specify a functional connectivity FC related to MDD diagnosis, features used for clustering are selected in accordance with the "importance" to the construction of disease identifier of each functional connectivity FC.

Figure 7:
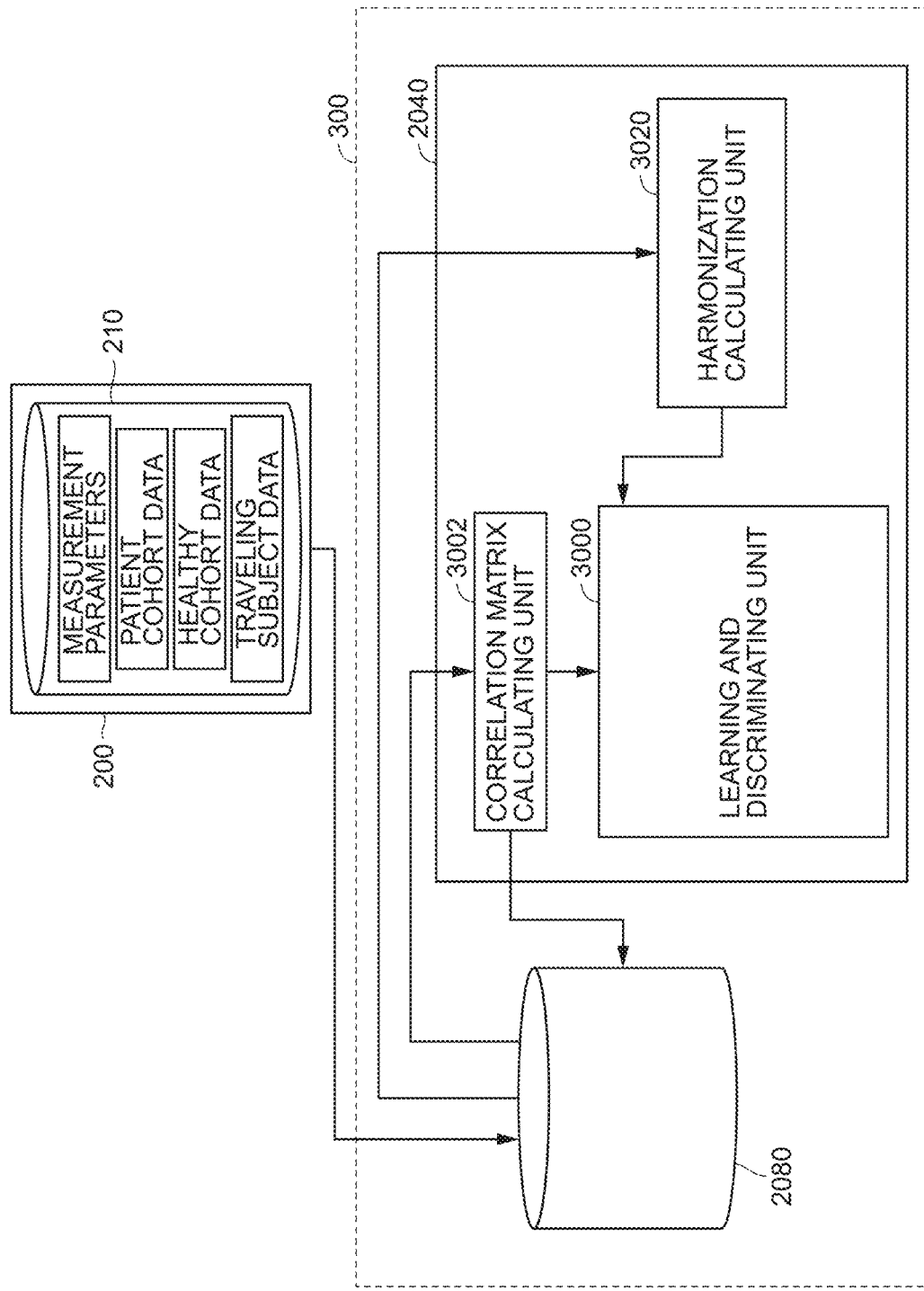
FIG. 7 is a functional block diagram showing the configuration of a computing system 300.
Figure 8:
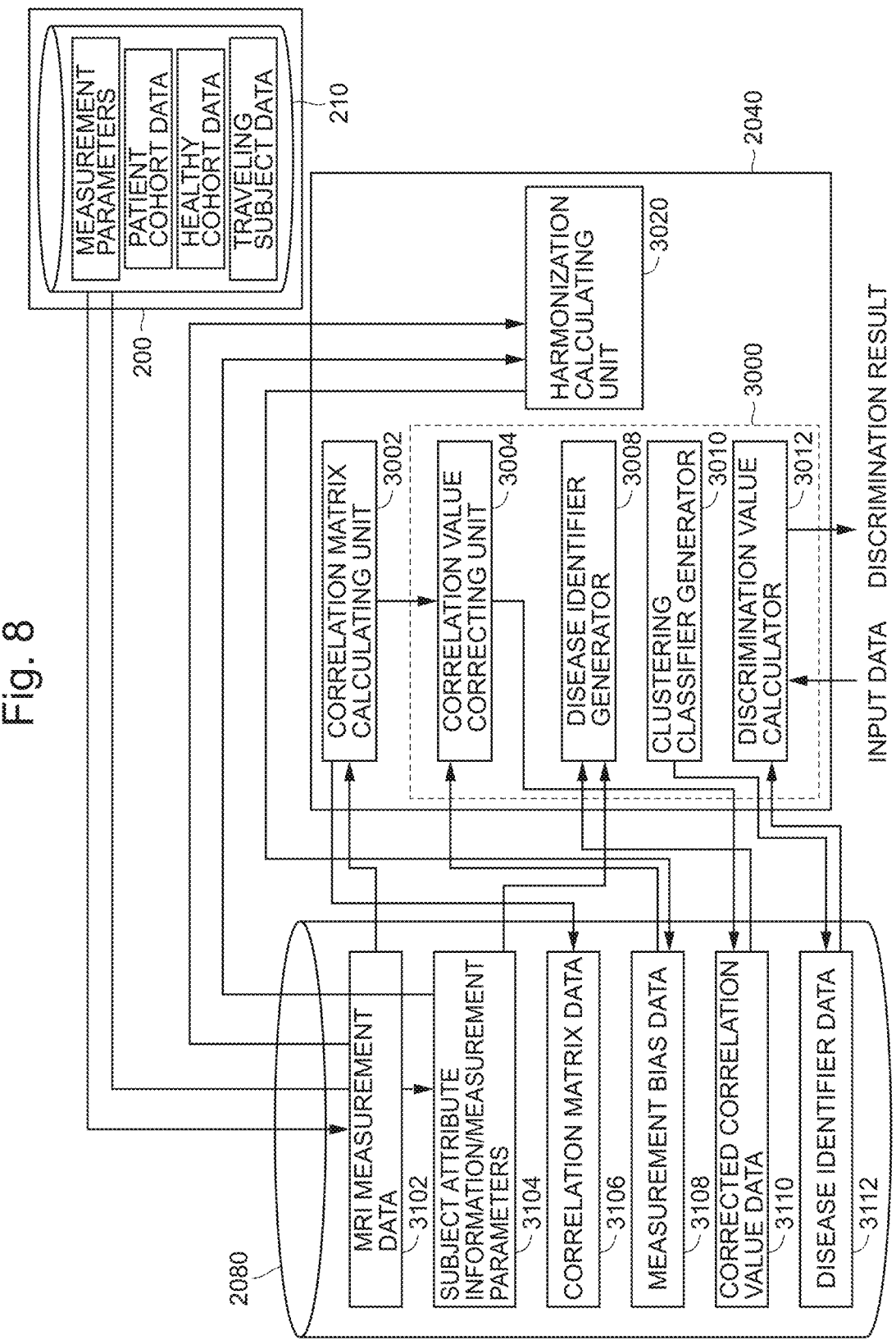
FIG. 8 is a functional block diagram showing the configuration of a computing system 300.

FIGS. 7 and 8 are functional block diagrams showing configurations of a computing system 300 performing a harmonization process, a disease identifier generating process, a clustering classifier generating process and a discriminating process based on the data stored in storage device 210 of data center 200.

Here, it is assumed that the "discriminating process" includes discrimination of disease (whether the subject has a disease or is healthy) and a classifying process of determining to which "cluster" (subtype) the subject of interest belongs.

Referring to FIG. 7, computing system 300 includes: a storage device 2080 for storing data from storage device 210 as well as data generated during the course of the calculation; and a processor 2040 performing operation on data in storage device 2080. Processor 2040 may be a CPU.

Processor 2040 includes: a correlation matrix calculating unit 3002 for calculating elements of the correlation matrix for the MRI measurement data 3102 of patient cohort and healthy cohort by performing a program and storing the results as correlation matrix data 3106 in storage device 2080; a harmonization calculating unit 3020 for performing the harmonization process; and a learning and discriminating unit 3000 for performing the disease identifier generating process, the clustering classifier generating process and the discriminating process using the generated disease identifier or clustering classifier, based on the result of harmonization process.

FIG. 8 is a functional block diagram showing the configuration of FIG. 7 in greater detail.

Figure 9:
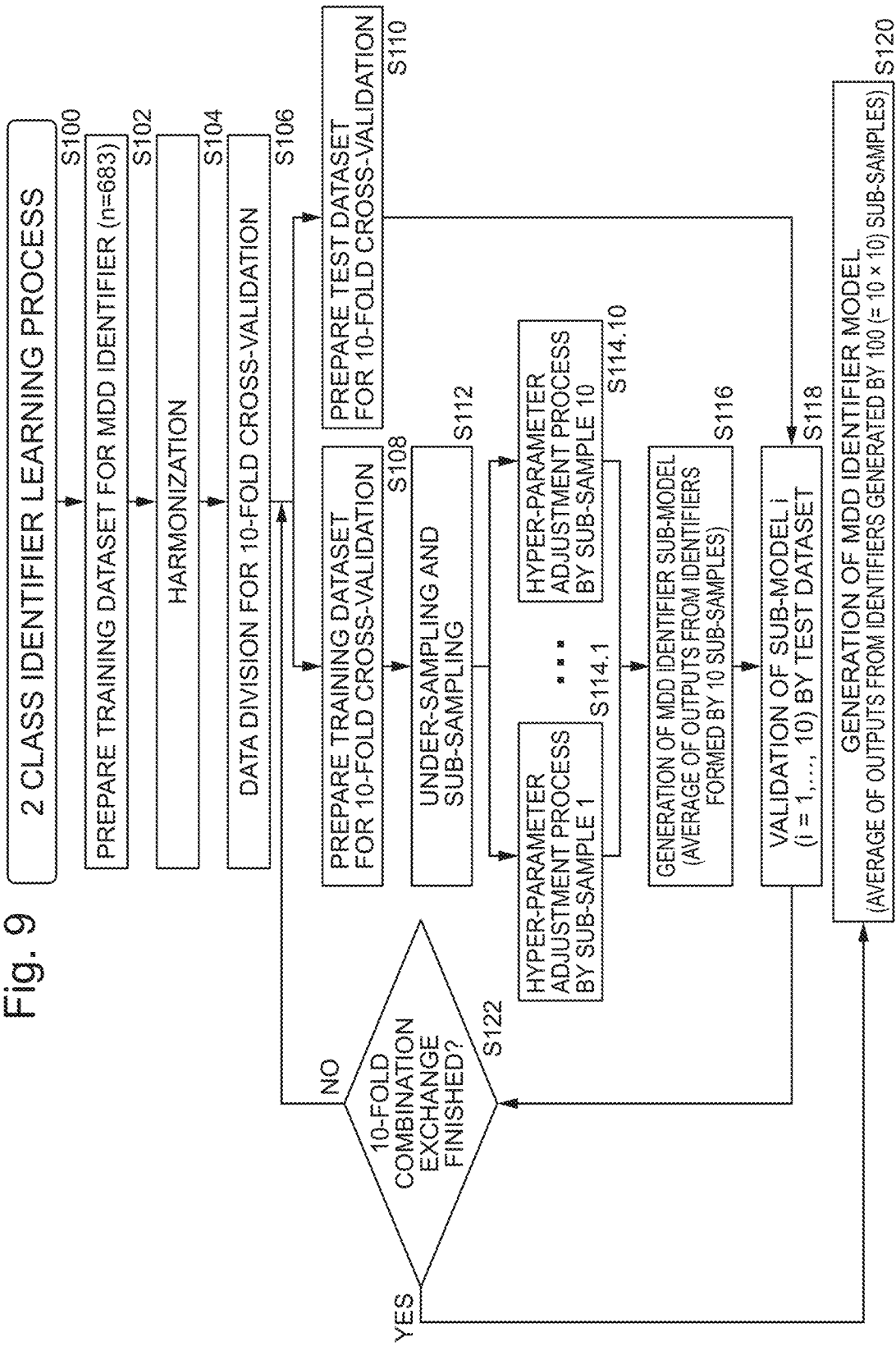
FIG. 9 is a flowchart representing a procedure of machine learning for generating a disease identifier using ensemble learning.

FIG. 9 is a flowchart illustrating the procedure of machine learning for generating the disease identifier through ensemble learning.

First, the harmonization process and the process up to the generation of identifier (disease identifier) through ensemble learning shown in FIG. 6 will be described with reference to FIGS. 8 and 9.

It is assumed that fMRI measurement data of subjects (healthy people and patients), attribute data of subjects and measurement parameters are collected from respective measurement sites and stored as "training dataset" in storage device 210 of data center 200.

Referring to FIGS. 8 and 9, a biomarker for the MDD discrimination is built using the above-described training dataset as the training data for the disease identifier (two-class classifier for "healthy" and "sick"). The marker identifies a group of healthy controls (a group of samples having a diagnosis label of healthy control (HC)) and a group of MDD patients (a group of samples having a diagnosis label of Major Depressive Disorder) based on 71,631 values of functional connectivity FC.

As will be described in the following, in the learning process for generating an identifier for MDD (hereinafter referred to as an MDD identifier), using the logistic regression analysis (one of sparse modeling methods) by the L1 regularization (LASSO: least absolute shrinkage and selection operator), an optimal subset of the functional connectivity FC is selected from 71,631 functional connectivity FC.

Generally, when L1 regularization is used, some parameters (in the following description, weight elements) can be reduced to zeros. In other words, feature selection is done, resulting in a sparse model.

It is noted, however, that the method of sparse modeling is not limited to the above, and other methods such as the variational Bayesian method or the sparse logistic regression (SLR) which applies the variational Bayesian method to the logistic regression, may be used.

Referring to FIG. 9, when the process of learning for the MDD identifier starts (S100), using prepared (i.e., stored in storage device 2080) training dataset (S102), correlation matrix calculating unit 3002 calculates elements of the connectivity matrix.

Thereafter, harmonization calculating unit 3020 calculates measurement biases and performs the harmonization process (S104).

As will be described later, the harmonization process using traveling subjects is preferred, though other methods may be used.

For example, it is possible to harmonize datasets by using ComBat method, which will be described later, between discovery dataset and independent validation dataset.

Thereafter, disease identifier generator 3008 generates the MDD identifier by applying a method which is a so-called "ensemble learning method," that is, a modification of a so-called Nested Cross Validation on the training data.

First, to perform the training process using the "K-fold cross validation" (K is a natural number) (external cross-validation), disease identifier generator 3008 sets K to 10, for example, and divides the training data into 10 subsets (S106).

Specifically, disease identifier generator 3008 uses one of the subsets of the K-fold (10-divided) data as a "test dataset" for validation, and assigns the remaining (K−1) (nine) data subsets as training dataset (S108, S110).

Then, disease identifier generator 3008 performs an "under-sampling process" and a "sub-sampling process" on the training dataset (S112).

Here, the "under-sampling process" means a process performed to even out the numbers of data in the training dataset corresponding to the specific, different (two or more) attributes that are the targets of the classification, when their numbers are different. Namely, it is a process of removing some data from a larger group of data having an attribute, so that the numbers of the data of different attributes will be equal.

Here, in the training dataset, the number of subjects of the MDD patient cohort is not equal to the number of subjects of healthy control cohort and, therefore, the process to equalize is performed.

Further, the "sub-sampling process" means a process of extracting a prescribed number of random samples from the training dataset.

Specifically, in the K-times iteration of cross validation through steps S108 to S118 and S122, in each cross validation, under-sampling is done for building the classifier since the numbers of the MDD patients and the healthy controls HCs are imbalanced in the training dataset. In addition, a prescribed number, for example, 130, of the MDD patients and the same number of healthy people are sampled at random from the training dataset as the sub-sampling process.

The number "130" is not limiting, and it is determined appropriately to enable the above-described under-sampling, in accordance with the amount of data in the training dataset (683 in the first dataset), the fold number K (here, K=10) and the degree of imbalance of the numbers of data respectively corresponding to specific attributes as the targets of classification.

Sub-sampling such as described above is performed, since under-sampling is disadvantageous because the removed data will not be used in training the classifier. Random sampling (or sub-sampling) is repeated M times (M=natural number, for example, M=10) to avoid the disadvantage.

As will be described later, under-sampling and sub-sampling as such are technically meaningful also for "feature selection" at the time of generating a "classifier" for "stratification." This point will be discussed later.

Thereafter, disease identifier generator 3008 performs a process for adjusting hyper parameters for each of the sub-samples one to 10 that have been sub-sampled (S114.1 to S114.10).

Here, by using the following logistic function on each sub-sample, a classifier sub-model is generated. The logistic function is used for defining the probability of a participant in the sub-samples belonging to the MDD class as follows:

$$P_{sub}(y_{sub} = 1 \mid c_{sub}; w) = \frac{1}{1 + \exp(-w^T c_{sub})}.$$  [Equation 1]

Here, $y_{sub}$ represents a class label of the participant (MDD, y=1; HC, y=0), $c_{sub}$ represents an FC vector for a given participant, and w represents a weight vector.

The weight vector is determined to minimize the following evaluation function (cost function) (LASSO calculation).

Assuming that $t_j = P_j(y_j = 1 \mid c_j; \omega)$,  [Equation 2]

$$J(\omega) = -\frac{1}{n_{sub}} \sum_{j=1}^{n_{sub}} [y_j \log t_j + (1 - y_j)\log(1 - t_j)] + \lambda \|\omega\|_1,$$

$$\|\omega\|_1 = \sum_{i=1}^{N} |\omega|_i.$$

In the LASSO calculation, the sum (L1 norm) of absolute values (1st order) of elements of the weight vector exists as the second term in the cost function.

Here, λ represents a hyper parameter and it controls the amount of shrinkage used for the evaluation.

In each sub-sample, though not limiting, disease identifier generator 3008 uses a prescribed number of data as hyper parameter adjusting data and uses the remaining data (for example, data of n=250 or 248 participants) to determine the weight vector w. Though not specifically limiting, here, assuming that the hyper parameter λ is in the range of 0<λ≤1.0, disease identifier generator 3008 divides this range into equal P intervals (P: natural number), for example, 25 intervals, and using each of the resulting λ values, determines the weight vector w by the LASSO calculation mentioned above.

Here, as the "Nested Cross Validation" described above, hyper parameter adjustment is done as the "internal cross validation." In the internal cross validation, the "test dataset" of the external cross validation is not used.

Then, disease identifier generator 3008 compares the discrimination performance (for example, accuracy) for the hyper parameter adjusting data using a logistic function corresponding to each generated λ value, and selects the logistic function that corresponds to the parameter λ that attains the highest discrimination performance (hyper parameter adjustment process).

Thereafter, disease identifier generator 3008 configures a "classifier sub-model" to output an average of output values of the logistic function corresponding to the sub-samples generated in the current loop of cross validation (S116). Because the identification performance is determined based on an average of identifier output values calculated for each sub-sample, this can be regarded as one type of "ensemble learning."

Using the test dataset prepared at step S110 as an input, disease identifier generator 3008 performs the validation of the classifier sub-model generated in the current loop of cross validation (S118).

As the method of generating a classifier sub-model by generating sub-samples by under-sampling and sub-sampling, and performing feature selection in each sub-sample, sparse modeling methods may be used other than the methods of using the LASSO method together with the hyper parameter adjustment described above.

If it is determined that the K-th (here, 10th) cross validation loop has not yet been finished (N at S122), disease identifier generator 3008 selects a sub-dataset of the K-divided data which is different from those used in past loops as the test dataset, and assigns the remaining sub-datasets as the training dataset (S108, S110), and repeats the process.

On the other hand, if it is determined that the K-th (here, 10th) cross validation loop is finished (Y at S122), disease identifier generator 3008 generates an identifier model for the MDD (MDD identifier) (S120) that outputs an average of outputs of K×M (here, 10×10=100) logistic functions (identifiers) for the input data.

After all, the MDD identifier can be regarded as an "identifier" obtained as a result of "ensemble learning" in that it provides an average of outputs from K×M identifiers as its identifying output.

When the output of the MDD identifier (probability of diagnosis) exceeds 0.5, it can be regarded as an index pointing to an MDD patient.

In the present embodiment also, as indexes for evaluating the performance of the MDD identifier generated in the above-described manner, Matthews correlation coefficients (MCC), AUC (area under the curve) of ROC (Receiver Operating Characteristic curve), accuracy, sensitivity and specificity are used.

The method of generating an identifier of an object disease (for example, MDD) by using a selected feature (here, components of the correlation matrix after the harmonization of the measurement biases) selected at each sub-sample is not limited to the process of averaging outputs of a plurality of identifier sub-models as described above. Such a classifier may be generated by majority voting or by using other modeling methods, particularly other sparse modeling methods, on the selected features.

(Examples and Performance of Data Used for MDD Identifier)

As already described above, in order to build reliable classifiers and regression models using the machine learning algorithms, it is necessary to use data of a large sample size collected from many imaging sites.

Therefore, in the following, we discuss such models using a resting state fMRI dataset for learning of about 700 participants, including the MDD patients, collected from four different imaging sites.

FIG. 10 shows the demographic characteristics of the training dataset (Dataset 1).

Dataset 1 is the data in the above-described SRPBS dataset.

FIG. 11 shows the demographic characteristics of the independent validation dataset (Dataset 2).

Dataset 2 is also, basically, the data in the SRPBS above.

Specifically, in the following analysis, the following two resting state functional MRI (re-fMRI) datasets are used.

(1) As shown in FIG. 10, the first dataset includes data of 713 participants (564 healthy controls HCs from four sites, 149 MDD patients from three sites).

(2) As shown in FIG. 11, the second dataset includes data of 449 participants (264 healthy controls HCs from four sites, 185 MDD patients from four sites).

Further, "depressive symptoms" are evaluated by using the Beck Depression Inventory (BDI) II obtained from most of the participants of each dataset.

Dataset 1 is a "training dataset" and used for building MDD identifiers and clustering classifiers.

Each of the measurements of participants was carried out in a single 10-minute session of resting state functional MRI (re-fMRI).

Here again, the resting state functional MRI (re-fMRI) data was obtained under the standardized imaging protocols (http://www.cns.atr.jp/rs-fmri-protocol-2/).

It is actually difficult, however, to ensure that every image diagnosis was done at every site using the same parameters, and two-phase modulation directions (P→A and A→P), MRI devices of two manufacturers (Siemens and GE), three different coil numbers (12, 24, 32) and scanners of three model numbers were used for measurements.

During the scanning of the resting state functional MRI (rs-fMRI), typically, an instruction such as shown below is given to each participant.

"Please try to relax. Please don't sleep. Keep looking at a cross mark in the center and do not think about any specific things."

The "demographic characteristics" in the dataset are the characteristics used in the so-called "demographics," and include the age, sex and attributes such as the diagnosis listed in the table.

In FIGS. 10 and 11, the number of participants in the parentheses indicates the number of participants having the BDI score data.

The demographic distributions match between the MDD and the HC sample groups in every training dataset ($p>0.05$).

Dataset 2 is the "independent validation dataset," which is used for testing the MDD classifiers and the clustering classifiers.

The sites used for the imaging of the second dataset are not included in Dataset 1.

The demographic distribution of age matches between the MDD and the HC sample groups ($p>0.05$) in the independent validation dataset, while the demographic distribution of sex does not match between the MDD and the HC sample groups in the independent validation dataset ($p<0.05$).

(Site Effect Control)

Further, in the following, description will be made assuming that in order to control site effect on the functional connectivity, the traveling subject harmonization method as will be described later is used for the training dataset.

It is noted, however, that the harmonization method is not limited to this, and other methods, such as the above-described ComBat method, may be used.

The ComBat method is disclosed, for example, in Reference 14 below. The disclosure of Reference 14 is incorporated herein by reference in its entirety.

Reference 14: Johnson W E, Li C, Rabinovic A. "Adjusting batch effects in microarray expression data using empirical Bayes methods." Biostatistics 8, 118-127 (2007).

The traveling subject harmonization method makes it possible to remove the pure site-to-site differences (measurement biases).

Note that no dataset of the traveling subject existed for the site or sites included in the independent validation dataset and, therefore, in order to control site effects in the independent validation dataset, harmonization was done using the ComBat method.

FIG. 12 shows the prediction performance (output probability distribution) of MDD on the training dataset for all imaging sites.

In the outputs from an identifier model for the training dataset, probability distributions of two diagnoses corresponding to the groups of the MDD patients and the healthy people are clearly separated to right (MDD) and left (HC) at the threshold value of 0.5.

The identifier model separates the MDD patients from the HC cohort with the accuracy of 66%.

The corresponding AUC is 0.77, showing a high identifying ability.

The MCC is about 0.33.

FIG. 13 shows the prediction performance (identifier output probability distribution) of MDD on the training dataset for each imaging site.

It can be seen from FIG. 13 that not only for the entire dataset but for respective datasets of the three imaging sites (site 1, site 2, site 4), almost equally high classification precision could be attained.

It is noted that in the dataset of site 3 (SWA), only a healthy control cohort exists. Its probability distribution, however, corresponds to that of the healthy controls of other sites.

(Identifier Generalization Performance)

FIG. 14 shows the classifier output probability distribution of the MDD on the independent validation dataset.

Specifically, the generalization performance of the identifier models is tested using an independent validation dataset.

Regarding MDD, in the process shown in FIG. 12, 100 (10-fold×10 sub-samplings) logistic function identifiers are generated by machine learning. An independent validation dataset is input to each of the generated 100 identifiers (identifier models as a set of classifiers).

For each participant, an average of outputs from 100 classifiers (probability of diagnosis) is calculated. If the averaged probability of diagnosis is >0.5, it is determined that the diagnosis label assigned to the corresponding participant is major depressive disorder.

In the independent validation dataset, the generated classifier models separate the MDD sample group from the HC sample group with the precision of about 70%.

The corresponding AUC is 0.75, indicating a performance attaining high discriminative power (permutation test $p<0.01$).

For the independent validation dataset, by the threshold value of 0.5, the probability distribution of outputs from the identifier models are clearly separated into two diagnoses corresponding to the groups of the MDD patients and the healthy people, that is, to the right (MDD) and to the left (HC).

Sensitivity is 68% and specificity is 71%, which leads to a high MCC value of 0.38 (permutation test p<0.01).

FIG. 15 shows the classifier output probability distribution of the MDD with respect to the independent validation dataset for each imaging site.

It can be seen that a high classification precision can be attained not only for the whole dataset of the four imaging sites but also for the individual dataset.

[Subject Data Clustering Process]

In the following, of the processes described with reference to FIG. 6, feature selection for clustering and clustering based on the selected features will be discussed in greater detail.

Specifically, the process referred to as "feature selection" and "clustering" in FIG. 6 will be described as processes performed by disease identifier generator 3008 and a clustering classifier generator 3010 shown in FIG. 8.

Figure 16:
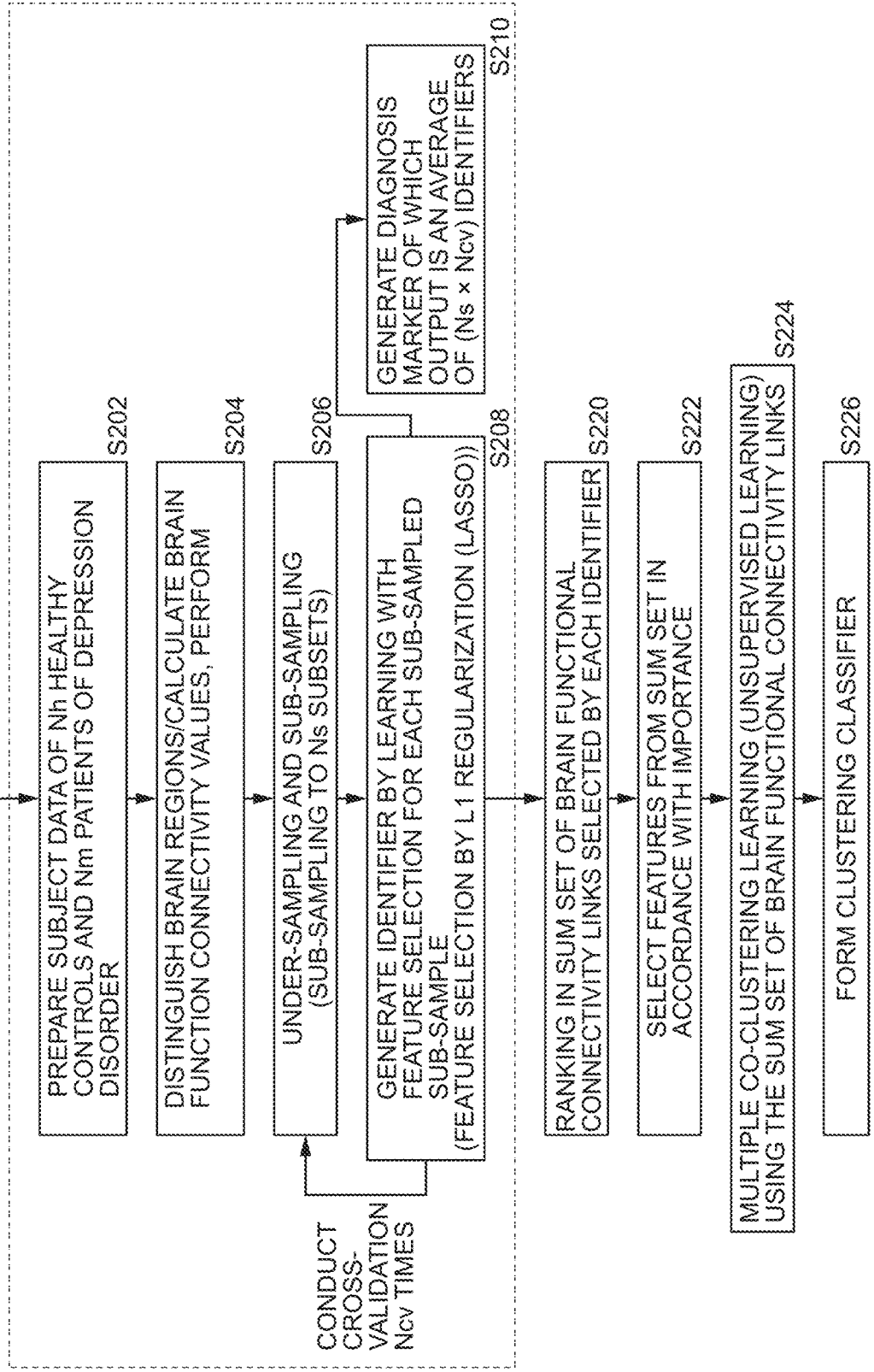
FIG. 16 is a flowchart representing a process of clustering by unsupervised learning by selecting features.

FIG. 16 is a flowchart representing a process of clustering by unsupervised learning by selecting features.

In the following, a process of clustering through unsupervised learning will be described in which features (brain functional connectivity links) used for generating sub-models of each identifier in the process of learning "two-class identifier" described with reference to FIG. 9 are ranked and a prescribed number of high-ranking features are used.

As already described above, brain functional connectivity comes to have as high as 70000 dimensions or higher depending on the method of brain parcellation, and hence, it is difficult to perform clustering through unsupervised learning in a common manner. In the present invention, to address this clustering problem, in the "generation of identifier through supervised learning," features are ranked in accordance with their importance, and "clustering through unsupervised learning" using the features selected in accordance with the ranking is combined to enable such clustering process.

In the following, for convenience of description, the clustering process is described as a process different from the process for generating a disease identifier. It is noted, however, that steps S200 to S210 of FIG. 16 are the same as steps S100 to S120 of FIG. 9, and the process for generating a disease identifier and the clustering process can be performed as a series of processes.

Referring to FIG. 16, when the learning process for clustering starts, disease identifier generator 3008 prepares subject data of Nh healthy people and Nm patients of depression disorder (S202). With the functional brain activity data of the subjects, disease identifier generator 3008 performs distinction of brain regions (parcellation), calculates brain functional connectivity values and performs harmonization (S204).

Thereafter, disease identifier generator 3008 performs data division for $N_{cv}$-fold cross validation ($N_{cv}$: natural number and $N_{cv} \geq 2$) and for each divided data, prepares a training dataset and a test dataset. For each training dataset, under-sampling and sub-sampling are performed to generate $N_s$ test data subsets (S206).

Further, disease identifier generator 3008 generates an identifier through learning with feature selection, for each of the sub-samples thus sub-sampled (S208). Here, as in the case of FIG. 9, it is assumed that feature selection is done by L1 regularization (LASSO).

The process of steps S206 to S208 as described above is repeated on the $N_{cv}$-divided training data set while successively changing combinations of training dataset (($N_{cv}$−1) of the divided dataset) and the test dataset (one of the divided data sets), until cross-validation is done $N_{cv}$ times.

An integrated identifier having the average of ($N_s \times N_{cv}$) identifiers as an output generated in this manner is provided as a disease identifier (diagnosis marker) (S210).

The process so far is the same as that of steps S100 to S120 of FIG. 9, as mentioned above.

On the other hand, at steps S206 to S208 that are repeated $N_{cv}$ times, regarding the sum set of features (brain functional connectivity links) selected for generating identifiers through learning with feature selection, though not limiting, clustering classifier generator 3010 performs ranking of the features in the sum set in accordance with the number of times each feature is selected (S220).

Here, the "number of times each feature is selected" will be referred to as the importance of the feature in this ranking.

In other words, by LASSO method, in the example shown in FIG. 9, one hundred (=10×10) identifiers are generated, while the number of selections of any brain functional connectivity of having non-zero weight in each identifier is counted +1. The connectivity having a larger count is ranked as one having higher importance.

Thereafter, in order to realize clustering of a patient cohort of depression disorder through unsupervised learning, clustering classifier generator 3010 selects a prescribed number of features in accordance with the importance, from the sum set (S222).

Further, clustering classifier generator 3010 performs clustering, using multiple co-clustering as will be described later as the method of unsupervised learning (S224).

Through the steps as described above, clustering classifier generator 3010 generates a clustering classifier for the patient cohort of depression disorder (S226).

Specifically, by the process above, clustering classifier generator 3010 specifies, from monitored data of each cluster, a probability distribution model that generates such monitored data, and information of each model is stored in storage device 2080. Then, a discrimination value calculator 3012 as the clustering classifier calculates, for any input data other than the training data, posterior probability of each cluster to which the input data belongs based on each probability distribution model, and outputs the result of classification that the input data belongs to that cluster which has the highest posterior probability (MAP: Maximum A posteriori Probability estimation method).

In the foregoing, the clustering process has been described as being based on the process of generating identifiers performed by disease identifier generator 3008 on the data of Nh subjects of healthy cohort and Nm subjects of patient cohort of depression disorder. The clustering method in accordance with the present invention, however, is not limited to such an example. It is applicable to a patient cohort of diseases other than "depression disorder." For example, the method can be used for clustering patient cohort of other mental disorders such as "patient cohort of schizophrenia," "patient cohort of autism," or "patient cohort of obsessive-compulsive disorder."

More generally speaking, let us consider any attribute label classified empirically by humans (for example, one's personality, one's specialty and so on). If it is found that a certain attribute has a prescribed relation with a pattern of correlation between brain regions of time-change in brain activities, it is possible to use the method for "clustering of subject cohort belonging to the certain attribute" (classification to subtypes), for the subjects classified in accordance with the attribute label.

(Under-Sampling and Sub-Sampling Processes)

In the process described above, "under-sampling and sub-sampling processes" are performed and, therefore, technical meaning of these processes will be briefly described.

First, the effect of "under-sampling process" is that it enables satisfactory setting of decision boundary of the identifiers.

Consider, for example, a task of classifying two classes. In the training data, if the data belonging to each of the two classes vary less in numbers, evaluation precision of identifier performance (such as accuracy) becomes higher in the process flow.

At steps S114.1 to S114.10 of FIG. 9, the process of determining "the logistic function that corresponds to λ attaining the highest discrimination performance" is performed for setting hyper parameters. Therefore, it is essential to correctly evaluate the "discrimination performance."

Assume an extreme example of identifier training using training data including one hundred data items belonging to Class 1 and one data item belonging to Class 2. In that case, even when the identifier should determine that every data belongs to Class 1, accuracy would not be much influenced. In this regard, it is meaningful to perform random sampling to make uniform the number of data belonging to the two classes.

As to sub-sampling, execution of several times with under-sampling is prerequisite from the following reasons.

First, under-sampling and sub-sampling performed only once leads to data bias, even when performed as random sampling.

Second, as will be described in the following, generation of an "identifier" repeated at steps S108 to S122 of FIG. 9 is realized by "ensemble learning" as described above.

Here, in generating each identifier, importance of features for identification is determined.

The importance is determined in accordance with the degree of contribution of each feature to the identification. For example, in the "learning with feature selection," what matters is the fact that the feature is selected matters, and in the "learning without feature selection," what matters is the weight of the feature on the calculated identification.

In the following, the meaning of "under-sampling" and "sub-sampling" will be described in determining the importance as such, taking "learning with feature selection" as an example. Even in "learning without feature selection" such as L2 regularization, we can assume that the event that "weight of the feature increases" basically comes from the same technical reason as the event of being "selected as a feature."

Here, the "learning with feature selection" may be a so-called "sparse modeling" such as the LASSO method described above.

In sparse modeling, features are selected sparsely. Specifically, specific features will have non-zero weights while other features have zero weight, and thus, features are selected. One reason why such sparse feature selection can be realized is as follows. When a "group of features contributing in a similar manner" to a "discrimination (identification) process" exists, there is a "penalty term corresponding to the number of features" to allow the learning process to proceed such that one feature of the group is selected and other features of the group come to have the weights of zero. This tendency is particularly dominant in the LASSO method.

Specifically, when feature A and feature B relate to the "discrimination process" in the similar manner, or when features A and B have high correlation, discrimination process with high discrimination performance is possible even when feature A only is selected as the feature.

In clustering, however, there may be a case in which both features A and B have to be considered. If a feature is selected simply in accordance with the degree of contribution to a discrimination process in the course of generating one identifier by the above-described "sparse" selection, the resulting "feature selection" could possibly be insufficient for the clustering.

Figure 17:
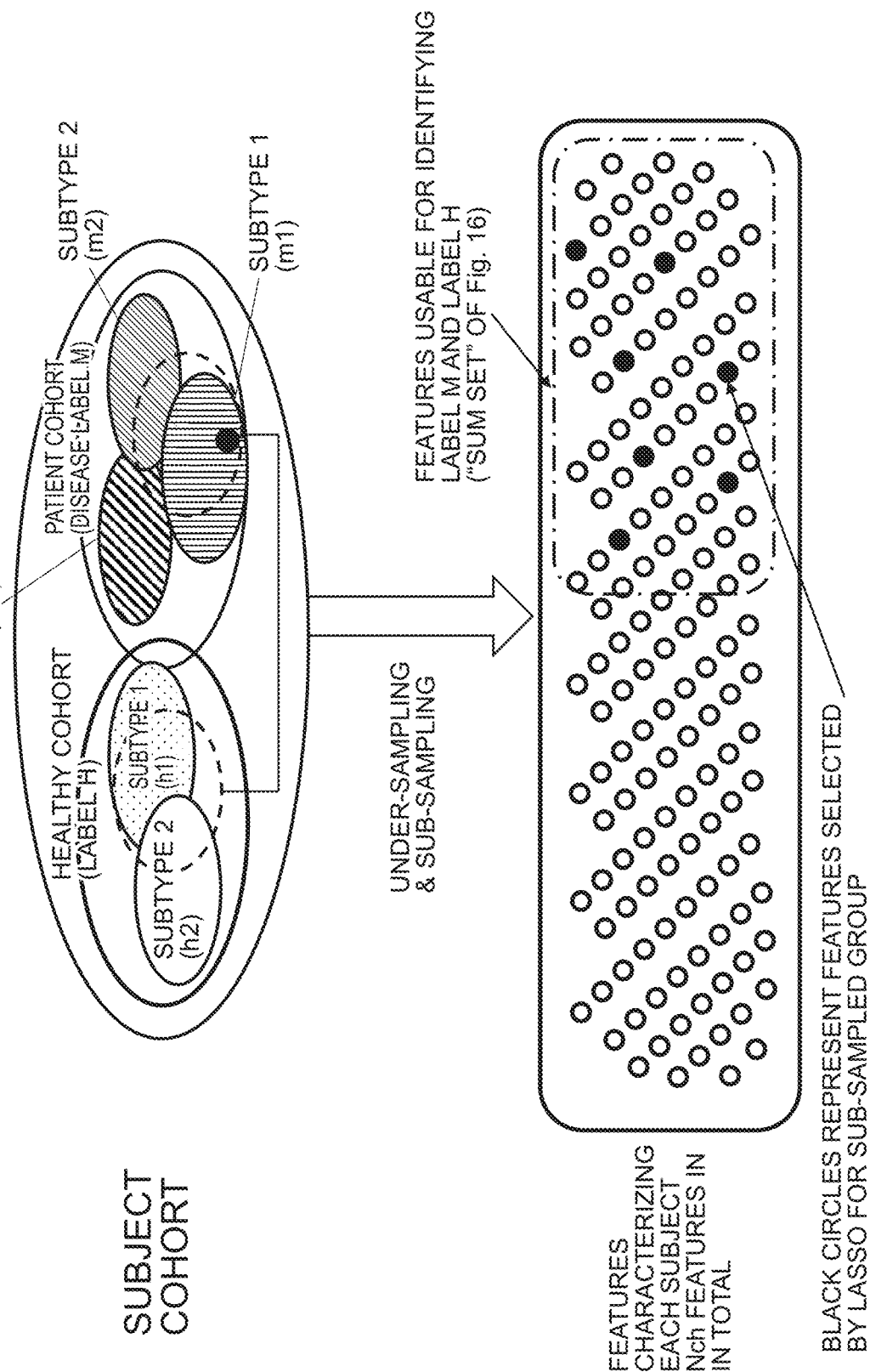
FIG. 17 shows a concept of performing feature selection when a plurality of (for example, Nch) features exist, by "learning with feature selection."

FIG. 17 shows a concept of performing feature selection when a plurality (for example, $N_{ch}$) of features exist, by "learning with feature selection."

Referring to FIG. 17, it is assumed that the subject cohort includes a healthy cohort and a patient cohort.

Subjects of the healthy cohort are labeled H, and the healthy cohort includes subtypes h1 and h2.

Subjects of the patient cohort are labeled M, and the patient cohort includes subtypes m1, m2 and m3.

Here, it is unknown from observables how many subtypes are included in the healthy cohort and the patient cohort, and the identification labels of subtypes are latent labels that are not explicitly given to the subjects.

The object of "clustering" is to perform data-driven clustering to the subtypes from the observables.

For the healthy cohort and the patient cohort as such, "under-sampling" and "sub-sampling" are performed on the subjects at random. Thus, from the "subject cohort" shown FIG. 17, subjects in the circles surrounded by dotted lines are selected respectively from the healthy cohort and the patient cohort.

It is assumed that features (brain functional connectivity correlation values) usable for identifying label M and label H are those in the area surrounded by a chain-dotted line in FIG. 17 ("sum-set of brain functional connectivity links" at step S220 of FIG. 16), among the brain functional connectivity links as the features ($N_{ch}$ features in total) characterizing each subject.

It is further assumed that as a result of learning of an identifier for identifying label M and label H through learning with feature selection (here, learning by the LASSO method), features represented by black dots in the area surrounded by the chain-dotted line in FIG. 17 are selected.

Figure 18:
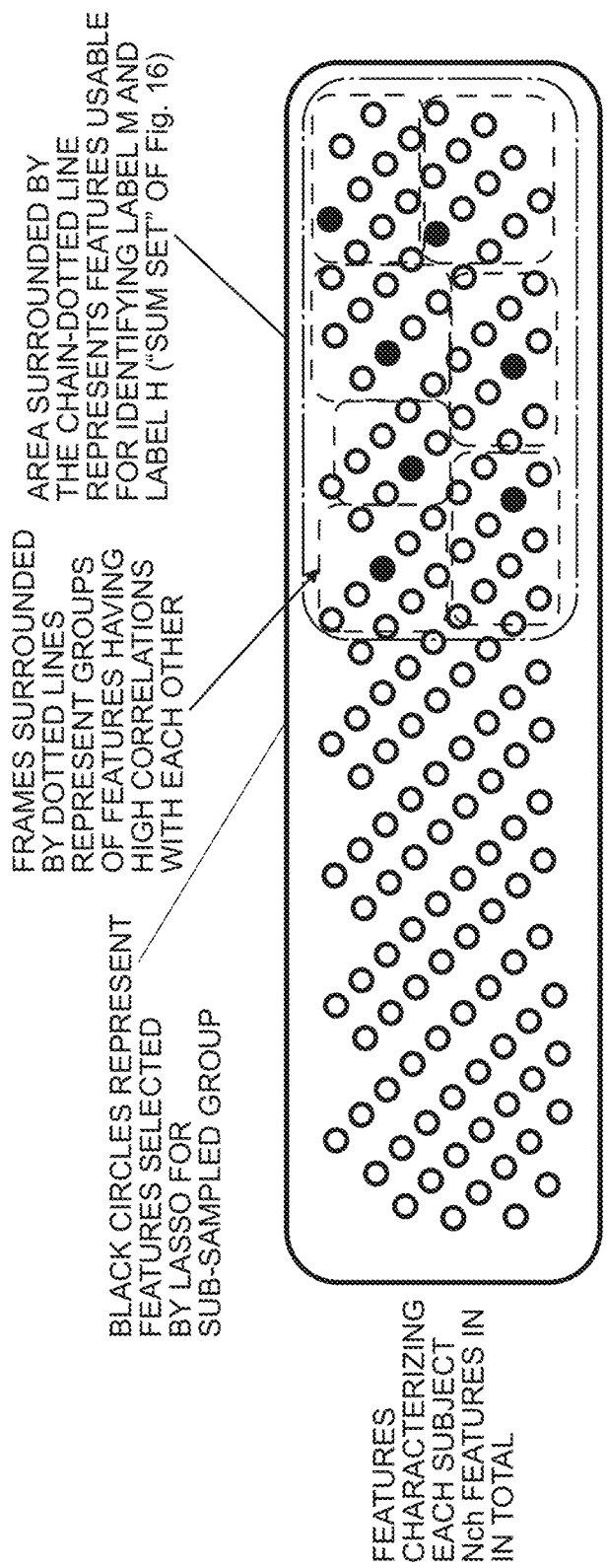
FIG. 18 is an illustration showing finally selected features when one identifier is generated by learning with feature selection.

FIG. 18 is an illustration showing the features finally selected after under-sampling and sub-sampling, when one identifier is generated by learning with feature selection.

It is assumed that as shown in FIG. 18, the features usable to identify label M and label H in the area surrounded by the chain-dotted line are further divided to groups of features having high correlations with each other, as represented by frames surrounded by dotted lines.

In the LASSO method, one feature is selected from each group of the dotted frames, and thus, the features are made sparse.

Figure 19:
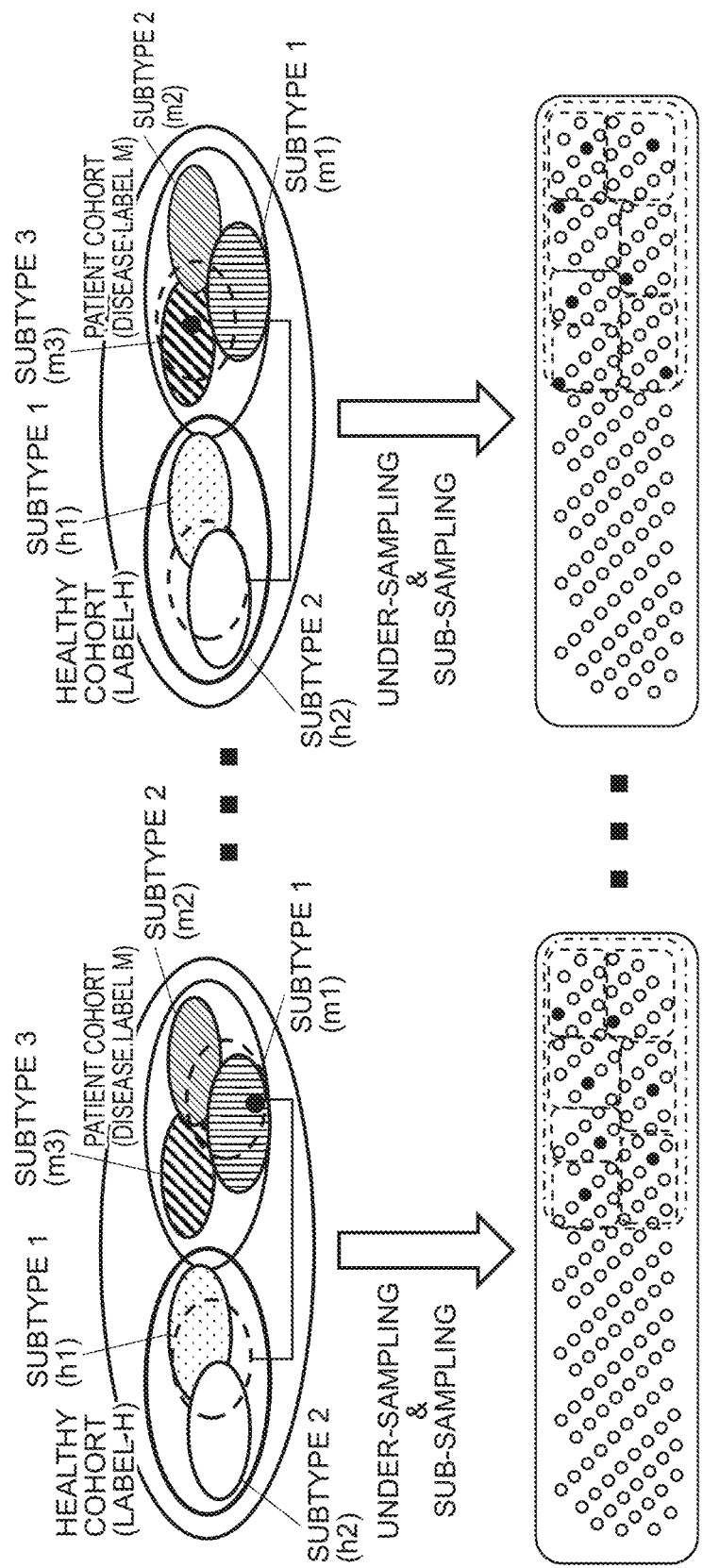
FIG. 19 is an illustration showing how features are selected when an identifier is generated by performing under-sampling and sub-sampling processes a number of times.

FIG. 19 is an illustration showing how features are selected when an identifier is generated by performing under-sampling and sub-sampling processes a number of times.

Referring to FIG. 19, assuming that sub-sampling is performed $N_s$ times, at each time, different subjects would be sub-sampled from the healthy cohort and the patient cohort.

As a result of learning of an identifier for identifying label M and label H through learning with feature selection on each sub-sample, different features would be selected by different identifiers as represented by black dots, from each group having high correlation, in the area surrounded by the chain-dotted line representing the sum-set mentioned above.

As a result, by executing the under-sampling and sub-sampling processes a number of times, a sum-set of features usable for identifying label M and label H is selected.

In the present embodiment, the features selected for each sub-sample by the learning with feature selection of identifiers in accordance with the LASSO method are ranked in the order of frequency of selection.

Using a prescribed number of features starting from the highest of the rank, for example, the highest one hundred features, clustering through unsupervised learning by "multiple co-clustering" as will be described later is performed at step S224 of FIG. 16.

In the foregoing, as the "learning with feature selection of identifiers," the LASSO method has been described as an example, and feature selection for clustering is performed in accordance with the rank in accordance with the frequency of selection.

As already described, however, in the clustering process in accordance with the present embodiment, "learning of identifiers with feature selection" is not limited to such a method, and a method such as random forest method may be used, and feature selection for clustering may be done in accordance with prescribed importance.

For example, in the random forest method described above, importance of features is calculated based on Gini impurity or permutation importance for the learning of identifiers and, therefore, features may be ranked in accordance with this importance, and using a prescribed number of features from the highest of the rank, clustering through unsupervised learning may be done by "multiple co-clustering" at step S224 of FIG. 16.

Here, "permutation importance" refers to "difference between an error of a model formed by randomized features and an error of the original model" and used to calculate "which feature contributes best to the model accuracy or does not contribute to the accuracy." Permutation importance is disclosed, for example, in Reference 15 below. The description of Reference 15 is incorporated herein by reference in its entirety.

Reference 15: Breiman, Leo. "Random forests." Machine learning 45.1 (2001): 5-32. https://link.springer.com/article/10.1023/A:1010933404324

Further, as "identifier generating process through ensemble learning," it is possible to use Ridge regularization or the like, and features may be ranked in accordance with the importance that corresponds to the median of the sum of absolute values of weight coefficients as described above. The feature selection for clustering may be performed using a prescribed number of features from the highest one of the ranks prepared in this manner.

[Multiple Co-Clustering]

In the following, the concept of "multiple co-clustering" at step S224 of FIG. 16 will be described to define the term "multiple co-clustering."

As a premise, it is understood that "clustering" refers to a method of data classification through unsupervised learning performed by a computer and, more specifically, to a method of automatically classifying given data without any external criterion. In contrast, "class separation" generally refers to a method of classification through "supervised learning." Further, a "cluster" is defined to be a subset of data having the properties of internal cohesion and external isolation. Here, external isolation refers to the property that objects belonging to different clusters are dissimilar, and internal cohesion refers to the property that objects in the same cluster are similar to each other. Further, as the measure of "similarity," distance between components in the set is defined. Generally, a distance is defined to satisfy the so-called "axioms of distance" and as the distance, Euclidian distance, Mahalanobis' distance, city block distance, or Minkowski distance is sometimes used.

Further, generally, known examples of the method of clustering through unsupervised learning include "partitional optimization clustering," which is a method of searching for partitioning that optimizes objective function defining goodness of a cluster, such as the "k-means clustering" which is one of the non-hierarchical methods, as well as "aggregative hierarchical clustering" and "divisive hierarchical clustering," which are hierarchical clustering methods.

These conventional clustering methods, however, are characterized in that all features are used to cluster objects (divide into groups) and the clustering result will be always the same.

Therefore, if there are a plurality of different manners of clustering depending on the features, these methods would not provide satisfactory results. Generally, the larger the number of features, the higher the possibility of existence of such a plurality of cluster structures.

The methods of clustering are not limited to the above. There is also an algorithm that, assuming that a plurality of objects to be clustered generate in accordance with a certain probability distribution, performs clustering to estimate the "probability distribution." As this type of clustering method, for example, "clustering with Gaussian mixture distribution" is known to realize more flexible clustering.

In the following, first, in order to describe an example in which there are a plurality of different manners of clustering depending on the features, we assume that in an object cohort including a plurality of objects to be clustered, each object is characterized by a plurality of features.

Figure 20:
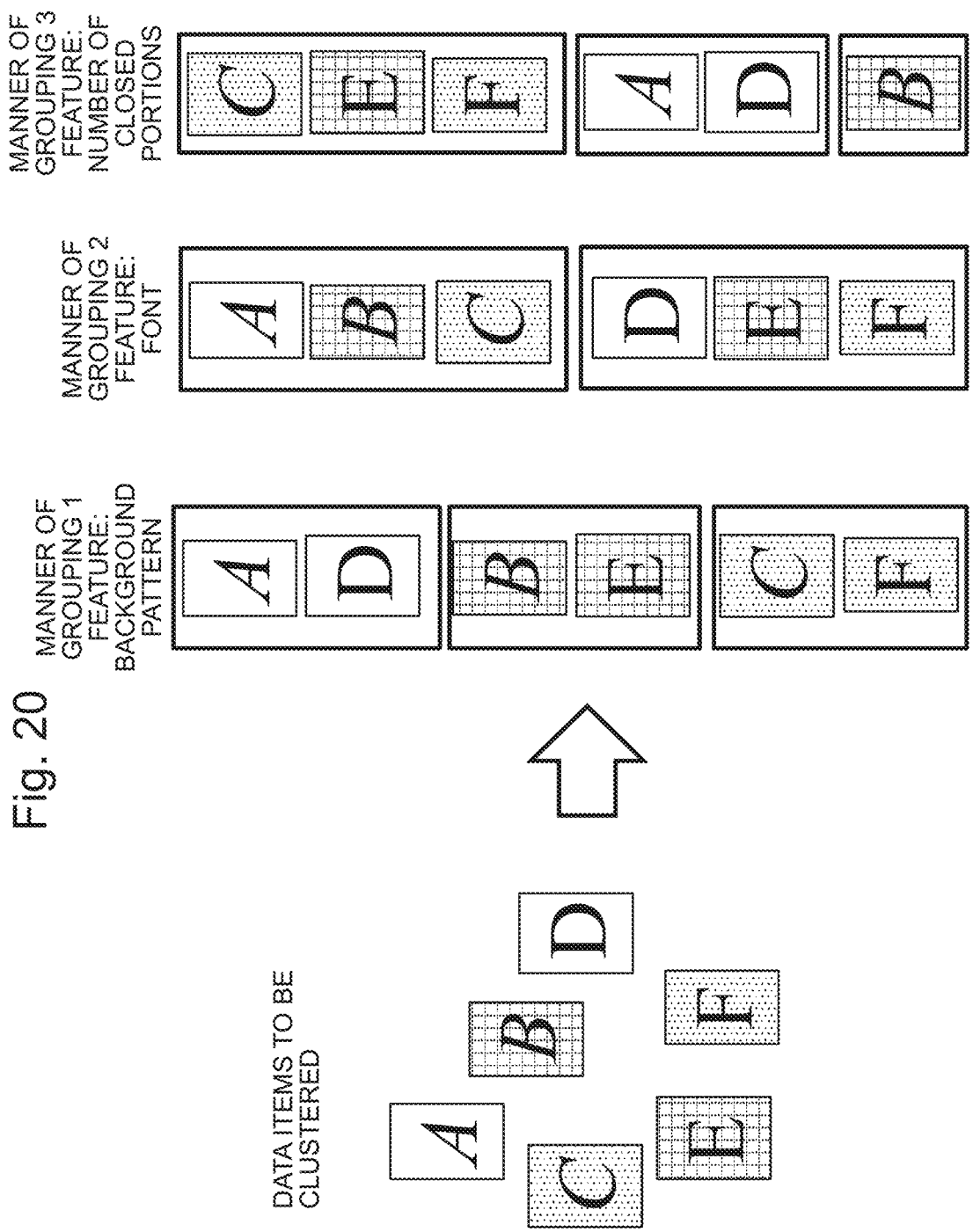
FIG. 20 is an illustration showing a plurality of different manners of clustering depending on features.

FIG. 20 is an illustration showing a plurality of different manners of clustering depending on features.

Referring to FIG. 20, data items to be clustered (hereinafter simply referred to as "objects") are six letters "A," "B," "C," "D," "E" and "F."

These letters have different background patterns and different fonts (styles).

Possible features characterizing these letters are "background pattern," "style" and "number of closed portions in the letter (number of areas fully surrounded by lines)."

Therefore, one same set of letters can be divided to different clusters depending on which feature is used for clustering.

In the example of FIG. 20, when "background pattern" is used, the letters can be clustered to three clusters, that is, {A, D}, {B, E} and {C, F}; when "style" is used, two clusters of {A, B, C} and {D, E, F}; and when "number of closed portions" is used, three clusters of {C, E, F}, {A, D} and {B} as having zero, one and two closed portions.

While FIG. 20 shows an example in which one cluster is characterized by one feature, generally, one cluster is characterized by a plurality of features.

Figure 21A:
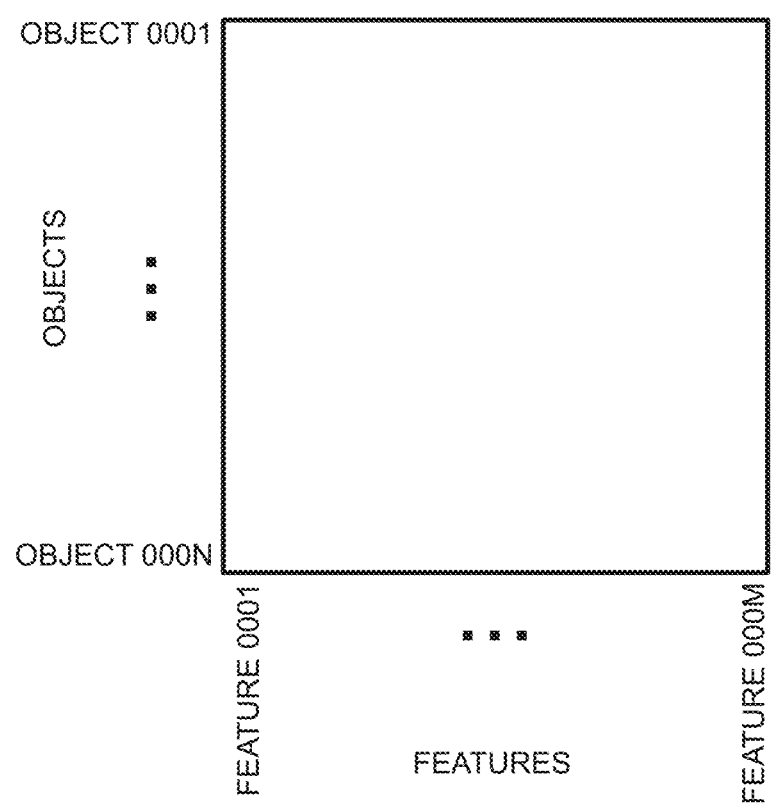
FIG. 21A is an illustration showing a concept of clustering when a plurality of objects is characterized by a plurality of features.

FIGS. 21A and 21B show a concept of clustering when a plurality of objects is characterized by a plurality of features.

First, let us consider a "data matrix" in which objects to be clustered are arranged along the row direction while features characterizing these objects are arranged along the column direction, as shown in FIG. 21A.

A method of clustering objects (partitioning the objects to a plurality of object clusters) and simultaneously clustering features to be related to each object cluster as shown in FIG. 21B is referred to as "co-clustering," which method is disclosed, for example, in Reference 16 below. The description of Reference 16 is incorporated herein by reference in its entirety.

Reference 16: Madeira S C, Oliveira A L. Biclustering algorithms for biological data analysis: a survey. IEEE/ACM Transactions on Computational Biology and Bioinformatics (TCBB). 2004; 1(1):24±45. https://doi.org/10.1109/TCBB.2004.2

In "co-clustering," by interchanging rows or columns of data matrix, that is, by re-arranging the objects and the features in accordance with the degree of similarity, the objects are divided into cluster blocks designated by (i, j) (i=1, 2: j=1, 2, 3), as shown in FIG. 21B.

Here, a generative model (probability model) for the objects included in each cluster is assumed and parameters of each probability model are determined such that observed data will have higher likelihood.

Once the probability model is inferred in this manner for each cluster, it becomes possible to discriminate (classify), for specific observed data (test data), to which cluster the data belongs.

Figure 22A:
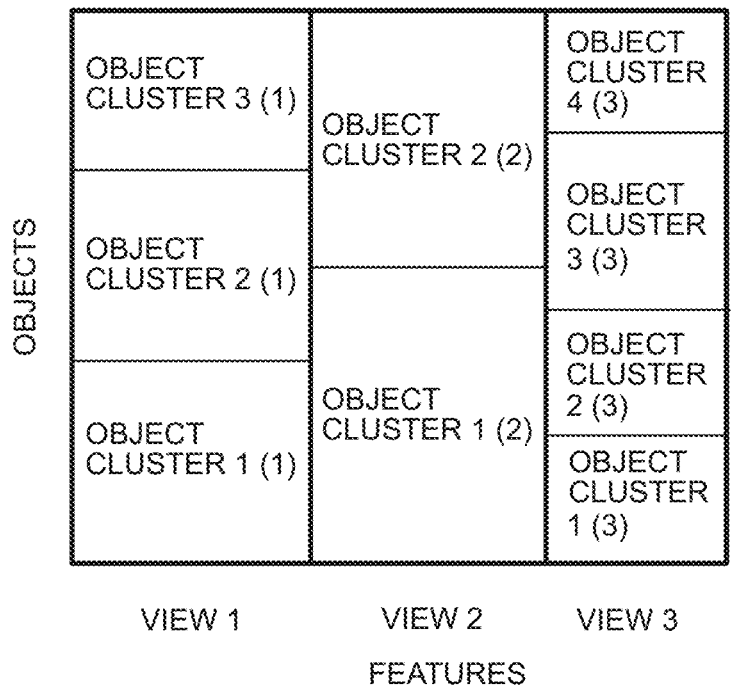
FIG. 22A is an illustration showing a concept of multiple clustering.
Figure 22B:
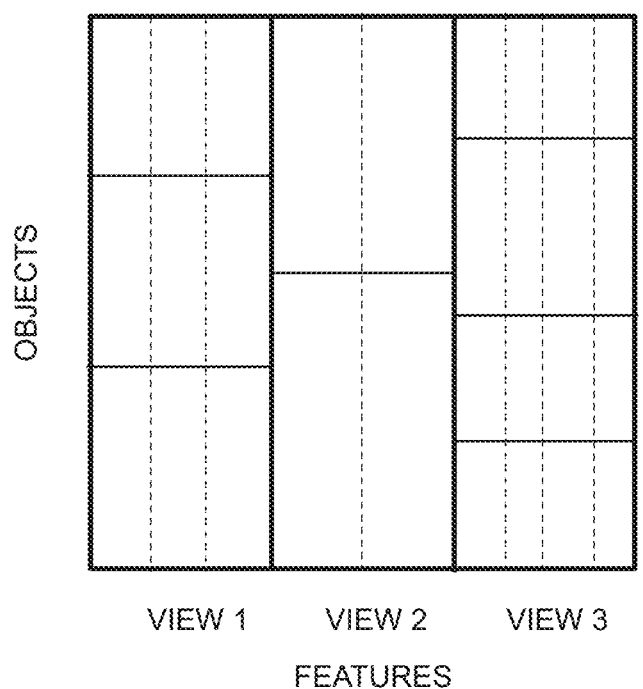
FIG. 22B is an illustration showing a concept of multiple co-clustering.

FIGS. 22A and 22B are illustrations showing concepts of multiple clustering and multiple co-clustering.

In "co-clustering" shown in FIG. 21B, the rows and columns of "data matrix" are interchanged to generate clusters having block structures. Therefore, when the features are divided to a plurality of feature clusters, the objects are clustered as commonly aligned along the plurality of feature clusters.

Considering that the features are partitioned to a plurality of feature clusters and the objects are partitioned to object clusters in each feature cluster, it is expected that a probability model of higher likelihood is attained if the arrangement of objects in each object cluster (how the objects included in an object cluster is arranged) is made different in different feature clusters.

In this case, as the manner of partitioning objects (object clustering) differs feature cluster by feature cluster, each feature cluster is specifically referred to as a "view (viewpoint)."

Clustering different objects for different views of features in the manner as described above is referred to as "multiple clustering," as shown in FIG. 22A.

Further, clustering with feature columns and object rows interchanged in each view may realize inference of a probability model having higher likelihood for the observed data, and this manner of clustering is referred to as "multiple co-clustering" as shown in FIG. 22B.

Here, we use the term "multiple co-clustering" even when there is only one view or there is only one type of feature cluster in at least one view, and we use "co-clustering" and "multiple clustering" as terms referring to subordinate concepts of "multiple co-clustering."

In the present embodiment, the simple term "clustering" refers to a generation of a set of clusters in one view. When partitioning of features to views is performed simultaneously with clustering of objects as shown in FIG. 22A, it is referred to as "multiple clustering" and distinguished when partitioning to views is performed simultaneously with co-clustering as shown in FIG. 22B, which is referred to as "multiple co-clustering."

FIG. 23 is an illustration showing a concept in which probability models of different types of probability distributions are assumed in one view in "multiple co-clustering."

In FIG. 23, white blocks and hatched blocks have different probability models of different types of probability distributions.

For example, white blocks may have a probability distribution of continuous random variable and the hatched portions may have a probability distribution of discrete random variable.

As will be described in the following, in the method of "learning of multiple co-clustering" in accordance with the present embodiment, it is possible to perform clustering on a distribution family including different distributions.

Figure 24:
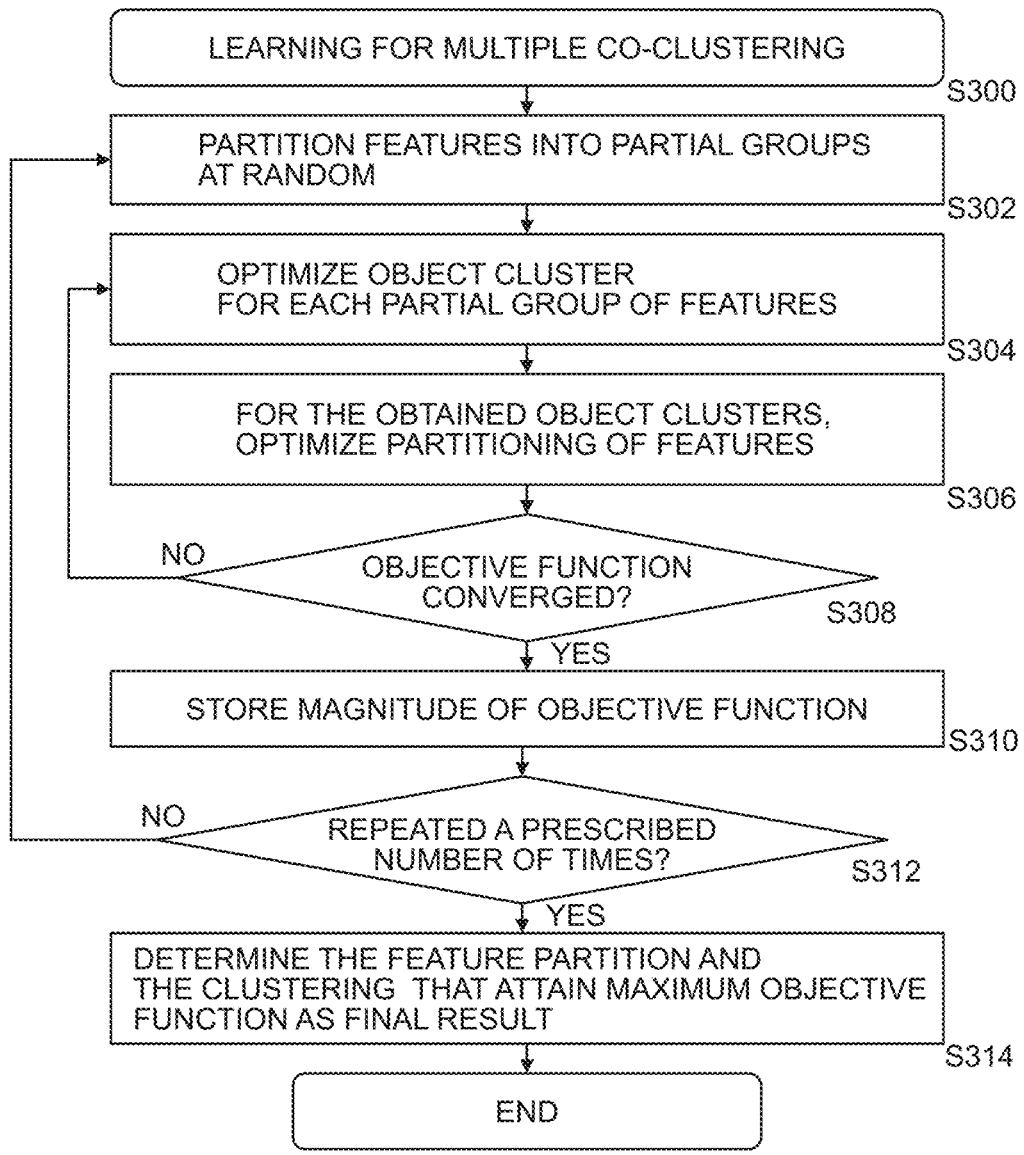
FIG. 24 is a flowchart outlining a method of learning of multiple co-clustering.

FIG. 24 is a flowchart outlining a method of learning of multiple co-clustering.

When the process of learning of multiple co-clustering starts (S300), clustering classifier generator 3010 divides features of a data matrix to partial groups at random, and thereby generates feature views and feature clusters in the views (S302; corresponding to generation of Y (initialization of Y) described later).

Thereafter, corresponding to the feature views and the feature clusters generated at step S302, clustering classifier generator 3010 generates partition of object clusters and optimizes the same (step S304: corresponding to generation of Z described later).

Further, for the obtained object cluster, clustering classifier generator 3010 optimizes partitioning of features (S306: corresponding to the Y generation process as described later, in which Y is optimized using the generated Z).

Thereafter, clustering classifier generator 3010 determines whether or not the objective function satisfies a prescribed condition and converges (S308). This objective function corresponds to a function $L(q(\phi))$, which will be described later. The function $L(q(\phi))$ monotonically increases as Y and Z, which will be described later, are updated, and if it is determined that the rate of this increase has come to be sufficiently small, it is determined to be converged. If it does not converge (NO at step S308), clustering classifier generator 3010 returns the process to step S304 and if it converges (YES at step 308), the process proceeds to the next step.

Then, clustering classifier generator 3010 stores the magnitude of objective function in a storage device 2080 (S310).

Then, clustering classifier generator 3010 determines whether or not the process of steps S302 to S310 has been repeated a prescribed number of times. If repetition has not reached the prescribed number (NO at step S312), clustering classifier generator 3010 returns the process to step S302, and if the number is reached (YES at S312), the process proceeds to the next step.

The manner of feature partitioning and the manner of clustering that attain the maximum objective function are determined as the final result (S314), and clustering classifier generator 3010 ends learning of multiple co-clustering, and thus generates a clustering classifier.

FIG. 48 illustrates a configuration of clustering classifier.

In the example of FIG. 48, features are partitioned to three views. View 1 is partitioned in accordance with a feature group 1 and objects are clustered to clusters 1 to 3; View 2 is partitioned in accordance with a feature group 2 and objects are clustered to clusters 1 to 4; and View 3 is partitioned in accordance with a feature group 3 and objects are clustered to clusters 1 and 2.

Hence, clustering classifier generator 3010 stores information of features corresponding to respective views as disease identifier data 3112 in storage device 2080, and information for specifying probability density function of each view (for example, when the probability density function has normal distribution, central coordinate μ and variance $\sigma^2$ of the distribution).

Referring to FIG. 48, assume that "new data item (data of a new subject)" not included in the training data and having feature groups 1 to 3 is input to the clustering classifier. Then, discrimination value calculator 3012 calculates, for the feature group 1 belonging to View 1, a posterior probability that the data belongs to each cluster, based on the probability density function in View 1. In the example of FIG. 48, the posterior probability of belonging to cluster 2 of View 1 is the highest and, therefore, classification result that the new data belongs to cluster 2 of View 1 is output. Likewise, classification results that the new data belongs to cluster 3 of View 2 and to cluster 1 of View 3 are output from the clustering classifier.

(Details of Multiple Co-Clustering)

In the following, the method of learning of multiple co-clustering described with reference to FIG. 24 will be discussed in greater detail.

Details of multiple co-clustering are disclosed in Reference 17 below and, therefore, outline thereof will be described in the following. The description of Reference 17 is incorporated herein by reference in its entirety.

Reference 17: Tomoki Tokuda, Junichiro Yoshimoto, Yu Shimizu, Go Okada, Masahiro Takamura, Yasumasa Okamoto, Shigeto Yamawaki, Kenji Doya, "Multiple co-clustering based on nonparametric mixture models with heterogeneous marginal distributions", PLOS ONE|https://doi.org/10.1371/journal.pone.0186566 Oct. 19, 2017

Figure 25:
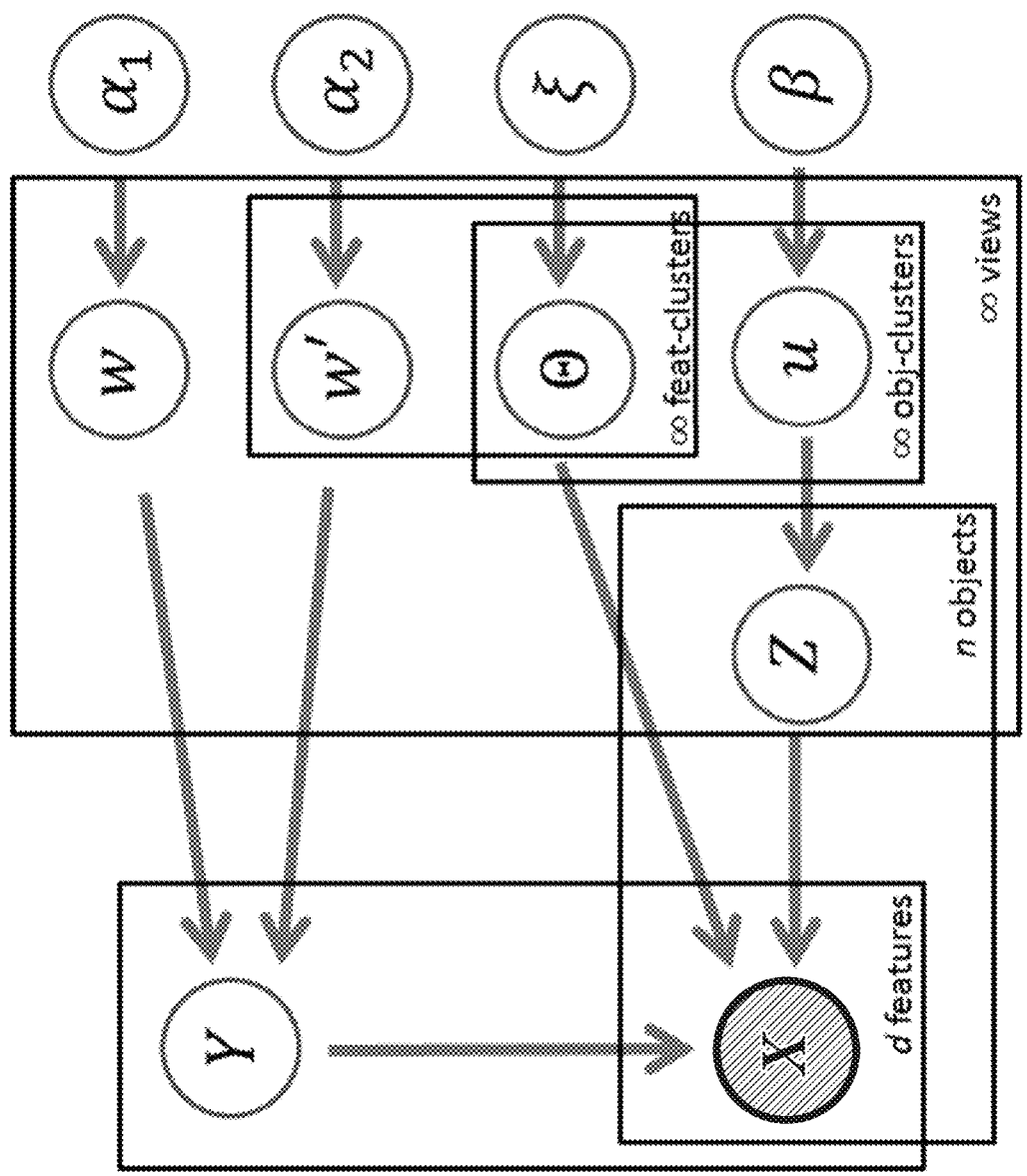
FIG. 25 shows a graph expression of Bayesian inference in the method of learning of multiple co-clustering.

FIG. 25 shows a graph expression of Bayesian inference in the method of learning multiple co-clustering shown in FIG. 24.

The multiple co-clustering model is summarized in the graphical model of FIG. 25, which graphical model clarifies causality links between related parameters and data matrix.

(Multiple Co-Clustering Model)

It is assumed that features (brain functional connectivity values) and subjects (here, subjects of the patient cohort) are represented as a data matrix such as shown in FIG. 21A.

Data matrix X is assumed to be formed of a distribution family consisting of known M distributions.

Probability distributions belonging to the distribution family may include Gaussian distribution, Poisson distribution and category distribution/multinominal distribution.

Clustering classifier generator 3010 decomposes $X^{(m)}$ as follows with data size $n \times d^{(m)}$:

$$X = \{X^{(1)}, \ldots, X^{(m)}, \ldots, X^{(M)}\}.$$

Here, m is an indicator for a distribution family (m=1, ..., M). Further, the number of views (viewpoints) is denoted by V (common to all distribution families), the number of feature clusters for View v and distribution family m is denoted by $G_v^{(m)}$, and the number of object clusters for view v is represented by $K_v$ (common to all distribution families).

Further, for the simplicity of expression, existence of empty cluster is allowed and, the number of features and the number of clusters are represented as $G^{(m)} = \max_v G_v^{(m)}$ and $K = \max_v K_v$.

With this notation, for independent identical distribution (i.i.d.) $d^{(m)}$-dimensional random vectors $X_1^{(m)}, \ldots, X_n^{(m)}$ for distribution family m, we consider a $d^{(m)} \times V \times G^{(m)}$ feature partition tensor (third order) Yon), in which if feature j of distribution family m belongs to the feature cluster g in view v, $Y_{j,v,g}^{(m)} = 1$ (0 otherwise).

Combining this for different distribution families, we let $Y = \{Y^{(m)}\}_m$.

Similarly, we consider a $n \times V \times K$ object partition (third order) tensor Z in which $Z_{i,v,k} = 1$ if object i belongs to object cluster k in view v.

Feature j belongs to one of the views ($\Sigma_{v,g} Y_{j,v,g}^{(m)} = 1$) while object i belongs to each view (i.e., $\Sigma_k Z_{i,v,k}^{(m)} = 1$). Further, Z is common to all distribution families, which implies that the estimated probability model estimates subject cluster solutions using information on all distribution families.

First, referring to FIG. 25, for a prior generative model of Y, we consider a hierarchical structure of views and feature clusters: views are first generated, followed by generation of feature clusters. Thus, features are partitioned in terms of pairs of view and feature cluster memberships, which implies that the allocation of feature is jointly determined by its view and feature cluster.

On the other hand, as shown in FIG. 25, objects are partitioned into object clusters in each view and hence, we consider just a single structure of object clusters for Z. We assume that these generative models are all based on "SBP" (Stick Breaking Process), as follows.

(Generation Model of Feature Cluster Y)

Assuming that $Y_{j.}^{(m)}$ denotes view/feature cluster membership vector for feature j of distribution family m, which is generated by a hierarchical stick-breaking process:

$$w_v \sim \text{Beta}(\cdot | 1, \alpha_1), v = 1, 2, \ldots \quad \text{[Equation 3]}$$

$$\pi_v = w_v \prod_{t=1}^{g-1}(1 - w_t),$$

$$w_{g,v}'^{(m)} \sim \text{Beta}(\cdot | 1, \alpha_2), g = 1, 2, \ldots, m = 1, \ldots, M$$

$$\pi_{g,v}'^{(m)} = w_{g,v}'^{(m)} \prod_{t=1}^{g-1}(1 - w_{t,v}'^{(m)}),$$

$$\tau_{g,v}^{(m)} = \pi_v \pi_{g,v}'^{(m)}$$

$$Y_{j,\ldots}^{(m)} \sim \text{Mul}(\cdot | \tau^{(m)}),$$

where, $\tau^{(m)}$ denotes $1 \times GV$ vector $(Y_{j,1,1}^{(m)}, \ldots, Y_{j,V,G}^{(m)})^T$.

Mul(•|π) is a multinominal distribution of 1 sample size with probability parameter 7E.

Beta(•|a, b) is a beta distribution with prior sample size (a, b).

$Y_{j.}^{(m)}$ is a $1 \times GV$ vector $(Y_{j,1,1}^{(m)}, \ldots, Y_{j,V,G}^{(m)})^T$.

Here, in accordance with a prescribed condition, we truncate the number of views with sufficient large V and the number of feature clusters with G.

Reference 18: Blei D M, Jordan M I, et al. Variational inference for Dirichlet process mixtures. Bayesian analysis. 2006; 1(1):121-143, https://doi.org/10.1214/06-BA104

When $Y_{j,v,g}^{(m)} = 1$, feature j belongs to feature cluster g at view v. By default, concentration parameters α1 and α2, which are hyper parameters, are set to 1.

(Generation Model of Object Cluster Z)

A subject cluster membership vector of object i in view v, denoted as $Z_{i,v}$, is generated by;

$$u_{k,v} \sim \text{Beta}(-|1, \beta), v = 1, 2, \ldots, k = 1, 2, \ldots \quad \text{[Equation 4]}$$

$$\eta_{k,v} = u_{k,v} \prod_{t=1}^{k-1}(1 - u_{t,v}),$$

$$Z_{i,v} \sim \text{Mul}(-|\eta_v),$$

where $Z_{i,v}$ is a 1×K (K has a sufficiently large value) vector given by $Z_{i,v} = (Z_{i,v,1}, \ldots, Z_{i,v,k})^T$. Concentration parameter $\beta$ is set to 1.

(Likelihood and Prior Distribution)

We assume that each instance $X_{i,j}^{(m)}$ independently follows a certain distribution, conditional on Y and Z. We denote $\theta_{v,g,k}^{(m)}$ as parameters of distribution family m in the cluster block of view v, feature cluster g and object cluster k.

Further, denoting $\Theta = \{\theta_{v,g,k}^{(m)}\}_{v,g,k,m}$, the log-likelihood of X is given by:

$$\log p(X \mid Y, Z, \Theta) = \sum_{m,v,g,k,j,i} \mathbb{I}(Y_{j,v,g}^{(m)} = 1) \quad \text{[Equation 5]}$$

$$\mathbb{I}(Z_{i,v,k} = 1) \log p(X_{i,j}^{(m)} \mid \theta_{v,g,k}^{(m)}).$$

Here, I(x) is an indicator function, which returns 1 when x is true and returns 0 otherwise. The likelihood is not directly associated with $w = \{w_v\}_v$, $w' = \{w'^{(m)}_{g,v}\}_{g,v}$ and $u = \{u_{k,v}\}_{k,v}$.

Joint prior distribution of unknown variables $\varphi = \{Y, Z, w, w', u, \Theta\}$ (namely, class membership variables and model parameters) is given by $$p(w)p(w')p(Y|w,w')p(u)p(A|u)p(\Theta). \quad \text{[Equation 6]}$$

(Variational Inference)

Variational Bayesian EM algorithm is used for MAP (maximum a posteriori) estimation of Y and Z.

Variational Bayesian EM algorithm is disclosed in Reference 19 below. The description of Reference 19 is incorporated herein by reference in its entirety.

Reference 19: Guan Y, Dy J G, Niu D, Ghahramani Z. Variational inference for nonparametric multiple clustering. In MultiClust Workshop, KDD-2010; 2010.

The logarithm of marginal likelihood p(X) is approximated using Jensen's inequality as shown below.

[Equation 7]

$$\log p(X) \geq \int q(\phi) \log \frac{p(X), \phi)}{a(\phi)} d\phi = \mathcal{L}(q(\phi)). \quad (1)$$

Jensen's inequality is disclosed in Reference 20 below. The description of Reference 20 is incorporated herein by reference in its entirety.

Reference 20: Jensen V. Sur les fonctions convexes et les inegalites entre les valeurs moyennes. Acta Mathematica. 1906; 30(1):175-193. https://doi.org/10.1007/BF02418571

Here, q($\varphi$) is an arbitrary distribution of parameter $\varphi$. It can be proved that the difference between the left and right sides is given by the Kullback-Leibler divergence between q($\varphi$) and p($\varphi$), that is, KL(q($\varphi$), p($\varphi$|X)). Hence, one approach of choosing q($\varphi$) is to minimize KL(q($\varphi$), p($\varphi$|X)); however, its evaluation is generally difficult.

Here, q($\varphi$) is selected so that is factorized over different parameters (mean-field approximation).

$$q(\phi) = q_w(w) q_{w'}(w') q_Y(Y) q_u(u) q_Z(Z) q_\Theta(\Theta), \quad \text{[Equation 8]}$$

where each q(•) is further factorized over subsets of parameters $w_v$, $w'^{(m)}_{g,v}$, $Y_j^{(m)}$, $u_{k,v}$, $Z_{i,v}$ and $\theta_{v,g,k}^{(m)}$.

In general, the distribution $q_i(\varphi_i)$ that minimizes ($\Pi_{l=1}^L q_l(\varphi_1), p(\varphi|x)$) is given by $$q_i(\phi_i) \propto \exp\{\mathbb{E}_{-q_i(\phi_i)} \log p(X, \phi)\}, \quad \text{[Equation 9]}$$

where $\mathbb{E}_{-q_i(\phi_i)}$ denotes averaging with respect to $\Pi_{l=1} q_l(\phi_l)$.

This characteristic is disclosed in Reference 21 below. The description of Reference 21 is incorporated herein by reference in its entirety.

Reference 21: Murphy K. Machine Learning: A Probabilistic Perspective. Cambridge, Massachusetts: MIT Press; 2012.

By applying this property to the currently discussed model, it can be shown that

[Equation 10]

$$q_w(w) = \prod_{v=1}^{V} \text{Beta}(w_v \mid \gamma_{v,1}, \gamma_{v,2})$$

$$q_{w'}(w') = \prod_{m=1}^{M} \prod_{v=1}^{V} \prod_{g=1}^{G} \text{Beta}(w_{g,v}^{(m)} \mid \gamma_{g,v,1}^{(m)}, w_{g,v,2}^{(m)})$$

$$q_Y(Y) = \prod_{m=1}^{M} \prod_{j=1}^{d^{(m)}} \text{Mul}(Y_{j\ldots}^{(m)} \mid \tau_j^{(m)})$$

$$q_u(u) = \prod_{v=1}^{V} \prod_{k=1}^{K} \text{Beta}(u_{g,v} \mid \gamma_{k,v,1}, \gamma_{k,v,2})$$

$$q_Z(Z) = \prod_{v=1}^{V} \prod_{i=1}^{n} \text{Mul}(Z_{i,v} \mid \eta_{i,v})$$

$$\log q_\Theta(\Theta) =$$

$$\sum_{m,v,g,k,j,i} \tau_{j,v,g}^{(m)} \eta_{i,v,k} \log P(X_{i,j}^{(m)} \mid \theta_{v,g,k}^{(m)}) + \sum_{m,v,g,k} \log p(\theta_{v,g,k}^{(m)}) + \text{constant}.$$

Here, we consider a function given by the expression below.

$$q_\Theta(\Theta). \quad \text{[Equation 11]}$$

Hyper parameters except for the above are given by the following equations.

[Equation 12]

$$\gamma_{v,1} = 1 + \sum_{m=1}^{M} \sum_{g=1}^{G} \sum_{j=1}^{d^{(m)}} \tau_{i,g,v}^{(m)}$$

$$\gamma_{v,2} = \alpha_1 + \sum_{m=1}^{M} \sum_{t=v+1}^{V} \sum_{g=1}^{G} \sum_{j=1}^{d^{(m)}} \tau_{i,g,t}^{(m)}$$

$$\gamma_{g,v,1}^{(m)} = 1 + \sum_{j=1}^{d^{(m)}} \tau_{j,g,v}^{(m)}$$

$$\gamma_{g,v,2}^{(m)} = \alpha_2 + \sum_{t=g+1}^{G} \sum_{j=1}^{d^{(m)}} \tau_{j,t,v}^{(m)}$$

-continued $$\gamma_{k,v,1} = 1 + \sum_{i=1}^{n} \eta_{i,v,k}$$

$$\gamma_{k,v,2} = 1 + \sum_{t=k+1}^{K} \sum_{i=1}^{n} \eta_{i,v,t}.$$

[Equation 13]

$$\log \tau = \sum_{k=1}^{K} \sum_{i=1}^{n} \eta_{i,v,k} \mathbb{E}_{q(\theta)}\left[\log p\left(X_{i,j}^{(m)} \mid \theta_{v,g,k}^{(m)}\right)\right] + \psi(\gamma_{v,1}) - \psi(\gamma_{v,1} + \gamma_{v,2}) + \quad (2)$$

$$\sum_{t=1}^{v-1} \{\psi(\gamma_{t,2}) - \psi(\gamma_{t,1} + \gamma_{t,2})\} + \psi\left(\gamma_{g,v,1}^{(m)}\right) - \psi\left(\gamma_{g,v,1}^{(m)} + \gamma_{g,v,2}^{(m)}\right) + \text{constant}$$

$$\log \eta_{i,v,k} = \sum_{m=1}^{M} \sum_{g=1}^{G} \sum_{j=1}^{d^{(m)}} \tau_{j,g,v}^{(m)} \mathbb{E}_{q(\theta)}\left[\log p\left(X_{i,j}^{(m)} \mid \theta_{v,g,k}^{(m)}\right)\right] + \psi(\gamma_{k,v,1}) -$$

$$\psi(\gamma_{k,v,1} + \gamma_{k,v,2}) + \sum_{t=1}^{K-1} \{\psi(\gamma_{t,v,2}) - \psi(\gamma_{k,v,1} + \gamma_{k,v,2}) + \text{constant,}$$

where $\mathbb{E}_{q(\theta)}$ denotes averaging with respect to the corresponding $q(\theta)$ of $\theta_{v,g,k}^{(m)}$.

φ(•) denotes the digamma function defined as the first derivative of logarithm of gamma function. Note that $\tau_{j,g,v}^{(m)}$ is normalized over pairs (g, v) for each pair (j, m). On the other hand, $\eta_{i,v,k}$ is normalized over k for each pair of (i, v).

Observation models and prior distribution of parameters Θ are specified in the following.

(Observation Model)

For observation models, we consider Gaussian, Poisson distribution and categorical/multinominal distributions. For each cluster block, we fit a univariate distribution of these families with the assumption that features within the cluster block are independent. We assume conjugate prior distributions for the parameters of the distribution families.

(Optimization Algorithm)

With the updating equations of the hyper parameters, the variational Bayes EM proceeds as follows.

First, $\{\tau^{(m)}\}_m$ and $\{\eta_v\}_v$ are randomly initialized, and then hyper parameters are updated until the lower bound L(q(φ)) of Equation (1) converges. This yields a locally optimal distribution q(φ) in terms of L(q(φ)). This procedure is repeated a number of times and the best solution with the largest lower bound as the approximated posterior distribution q*(φ) is selected.

MAP estimates of Y and Z are then evaluated as arg max$_Y$q*$_Y$(Y) and arg max$_Z$ q*$_Z$(Z), respectively.

The lower bound L(q(φ)) is given by

[Equation 14]

$$\mathcal{L}_{(q(\phi))} = \int q(\phi) \log p(X|\phi) d\phi - \mathbb{KL}_{(q(\phi),p(\phi))}. \quad (3)$$

Both terms on the right side can be derived in closed forms. It can be shown that this monotonically increases as q(φ) is optimized. Specifically, as already described, the function L(q(φ)) has a property of monotonous increase as Y and Z are updated, and if the rate of increase is determined to be sufficiently small (for example, though not limiting, when a condition that the increment attains to a prescribed value or smaller is satisfied), it is determined to be converged.

First, a distribution family for each feature is identified, generating a data matrix for the corresponding distribution family. Then, for a set of these data matrices, MAP estimates of Y and Z are generated, and using the estimates of Y and Z, object/feature cluster structures in each view are analyzed.

(Model Expression)

The multiple co-clustering model is sufficiently flexible to represent different clustering models because the number of views and the number of feature/object clusters are derived in a data-driven approach. For instance, when the number of views is one, the model coincides with a co-clustering model. When the number of feature clusters is one for all views, it matches the multiple-clustering model. Furthermore, when the number of views is one and the number of feature clusters is the same as the number of features, it matches conventional mixture models with independent features. Moreover, the model can detect non-informative features that do not discriminate between object clusters. In such a case, the model yields a view in which the number of object clusters is one. The advantage of this model is to automatically detect such underlying data structures.

The "multiple co-clustering method" as described above makes it possible to:

1) identify the manner of partitioning a plurality of clusters behind the data (not only the manner of partitioning objects but also the manner of partitioning features) and the corresponding groups of features in a data-driven manner;

2) identify a cluster that could not be found by any other method; and 3) attach meaning to the manner of partitioning clusters feature by feature, making it easier to interpret each cluster.

[Evaluation of Dataset Clustering Results]

In the following, we verify generalization performance of clustering by first dividing the multi-facilities, large scale fMRI data collected from a large number of subjects published as SRPBS mentioned above into two, and then applying the above-described multiple co-clustering to each of the divided data.

FIGS. 26A and 26B show the two-divided Dataset 1 and Dataset 2.

Dataset 1 shown in FIG. 26A consists of data of 545 healthy subjects and 138 patients of depression disorder obtained at Facilities 1 to 4, and Dataset 2 consists of data of 263 healthy subjects and 181 patients of depression disorder obtained at Facilities 5 to 8. Basically, these correspond to the datasets shown in FIGS. 10 and 11.

FIG. 27 is an illustration showing a concept of clustering performed on each dataset.

As shown in FIG. 27, Dataset 1 is clustered by multiple co-clustering in accordance with the flow shown in FIG. 24 independently.

Here, what is of interest is the degree of similarity between each of the clusters obtained by data-driven clustering independently performed on Datasets 1 and 2 (how similar the clusters are to each other).

If clustering of Datasets 1 and 2 results in classification (forming groups) to clusters having the same or similar characteristics (groups of subjects), it means that such a data-driven clustering is performed with high generalization performance, independent of facilities or measuring devices. Here, what matters is how to quantitatively evaluate the attained degree of the "classification to clusters having the same or similar characteristics".

Figure 28:
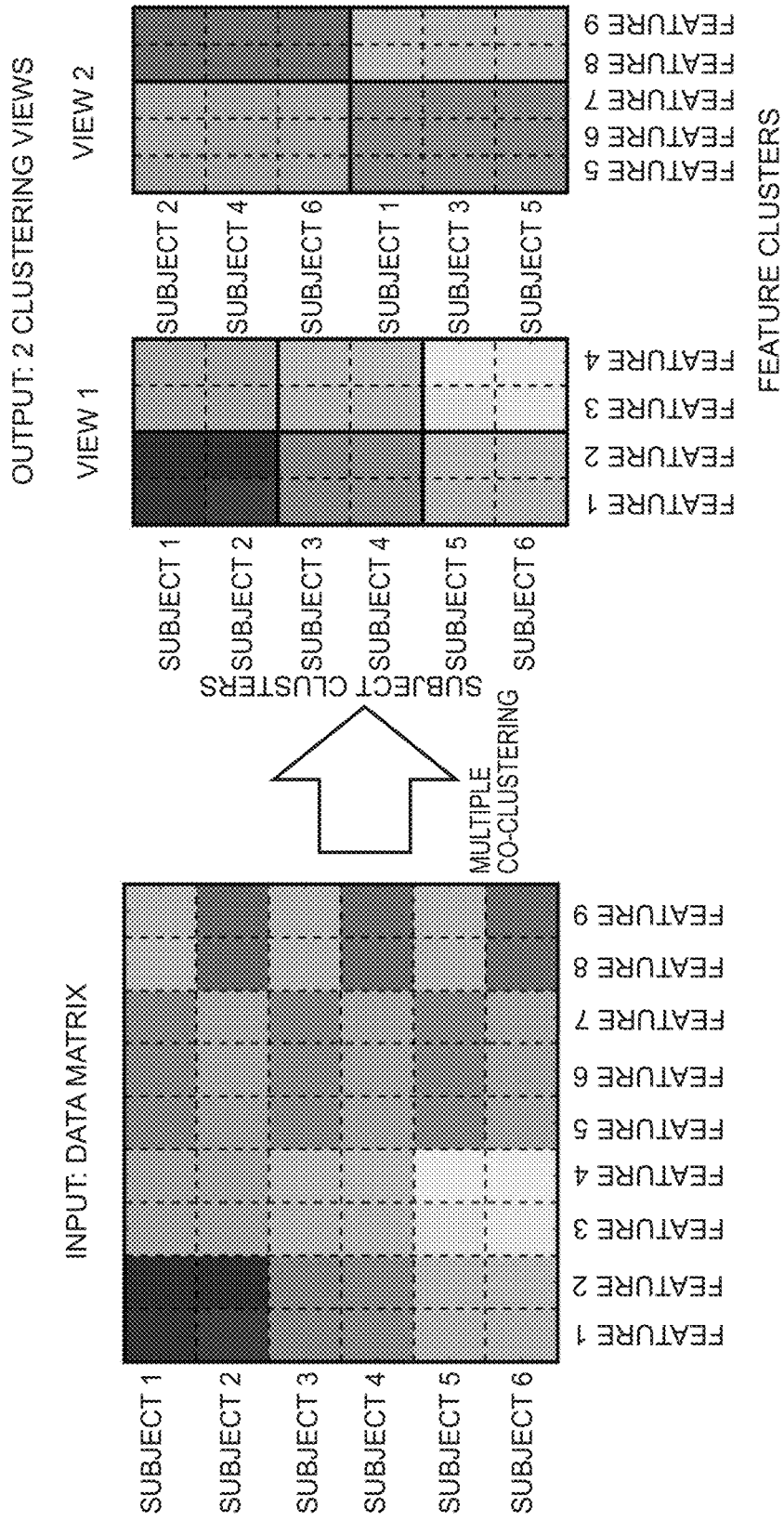
FIG. 28 is an illustration showing an example of multiple co-clustering of subject data.

FIG. 28 is an illustration showing an example of multiple co-clustering of subject data.

Referring to FIG. 28(a), assume that an input data matrix has subjects arranged along the row direction and features along the column direction.

By way of example, multiple co-clustering on the input data matrix results in features divided into two views, and in each view, the subjects are clustered, as shown in FIG. 28(b).

Figure 29:
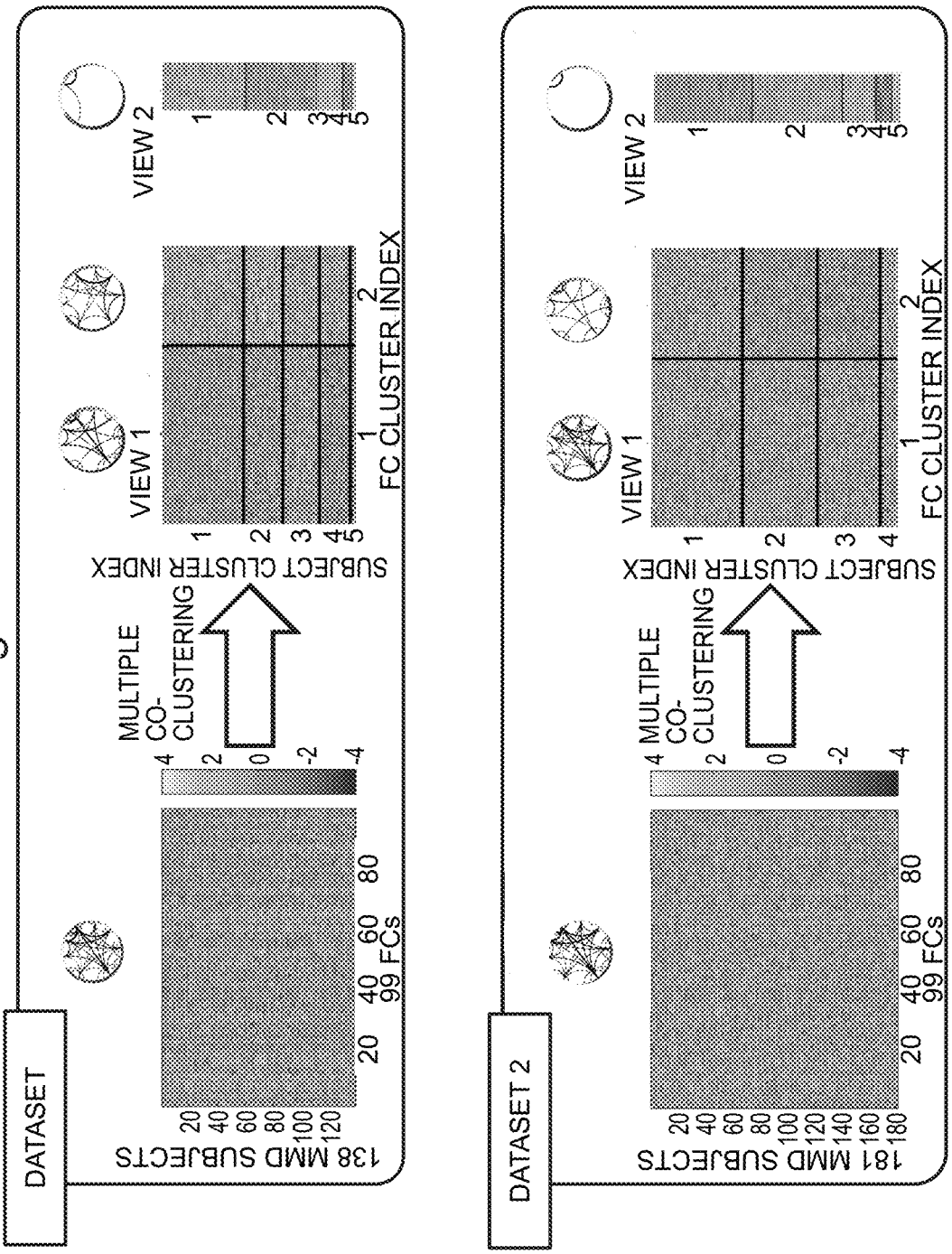
FIG. 29 shows results of multiple co-clustering actually performed on Datasets 1 and 2.

FIG. 29 shows results of multiple co-clustering actually performed on Datasets 1 and 2.

In FIG. 29, as features for clustering, 99 features are selected both for Datasets 1 and 2.

Then, multiple co-clustering is performed on 138 patients of depression disorder in Dataset 1 and on 181 patients of depression disorder in Dataset 2.

In Dataset 1, the features are partitioned into two views, that is, View 1 and View 2. View 1 is further co-clustered into two feature clusters, the subjects are clustered into five subject clusters, and in View 2 also, the subjects are partitioned into five clusters.

In Dataset 2 also, the features are partitioned into two views, that is, View 1 and View 2. View 1 is further co-clustered into two feature clusters, the subjects are partitioned into four subject clusters, and in View 2, the subjects are partitioned into five clusters.

Figures 30, 32B:
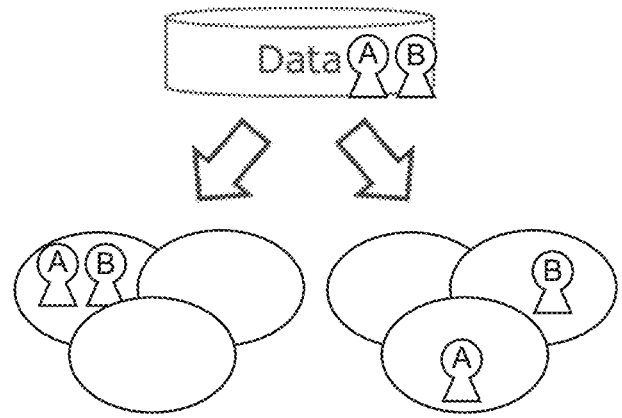
FIG. 30 shows, in the form of a table, counts of brain functional connectivity links (FCs) allocated to respective views of Datasets 1 and 2.
FIG. 32B illustrates a concept of ARI.

FIG. 30 shows, in the form of a table, counts of brain functional connectivity links (FCs) allocated to respective views of Datasets 1 and 2.

In Dataset 1, as features, 92 FCs are allocated to View 1 and 7 FCs to View 2.

In Dataset 2, as features, 93 FCs are allocated to View 1 and 6 FCs to View 2.

Further, in this table, the numbers of allocated brain functional connectivity links that match in Datasets 1 and 2 are plotted on the diagonal of the table. It can be seen that the brain functional connectivity links allocated to View 1 and View 2 are substantially the same in Datasets 1 and 2.

(Method of Verifying Generalization Performance (Similarity Between Datasets) of Clustering (Stratification))

In the following, we will quantitatively evaluate the similarity between the clusters (the degree of agreement), which are obtained by data-driven clustering individually performed on Datasets 1 and 2.

FIG. 31 illustrates methods of evaluating similarity of clustering (generalization performance of stratification).

First, referring to FIG. 31(A), assume that Datasets 1 and 2 are partitioned into clusters independently by multiple co-clustering as described above. In this case, since the subjects are independent from each other in the clusters of respective datasets, it is difficult to compare similarity of clustering.

Here, the result of classification of subjects in Dataset 1 using a classifier 1 formed by Dataset 1 is denoted as Clustering 1. On the other hand, the result of classification of subjects in Dataset 2 using a classifier 2 formed by Dataset 2 is denoted as Clustering 2.

Meanwhile, referring to FIG. 31(B), the result of classification of subjects in Dataset 2 using a classifier 1 formed by Dataset 1 is denoted as Clustering 1'. On the other hand, the result of classification of subjects in Dataset 1 using a classifier 2 formed by Dataset 2 is denoted as Clustering 2'.

Here, between Clustering 1 and 1' and Clustering 2 and 2', subjects of classification are common and, therefore, it is possible to evaluate similarities between them.

(Evaluation Standard of Measuring Degree of Similarity (Recall of Clustering))

Here, clustering process is data-driven and the values of cluster indexes (order of index values) of FIG. 29 are of no significance. Therefore, the problem is how to evaluate the degree of similarity when one same dataset is subjected to different clustering processes.

For example, assume that there are two results of clustering $\pi$ and $\rho$ on the same dataset X. As a metric for evaluating the similarity (external validity index) between the two results of clustering, Rand index is known.

When we consider all data pairs $\{x_1, x_2\} \in X (M=N(N-1)/2)$ in a dataset, there are the following types of pairs, and the number of pairs of respective types will be defined as follows.

[Equation 15]

$a_{11}$: The number of pairs belonging to the same cluster in both $\pi$ and $\rho$ $a_{01}$: The number of pairs belonging to different clusters in $\pi$ and belonging to the same cluster in $\rho$ $a_{10}$: The number of pairs belonging to different clusters in $\rho$ and belonging to the same cluster in $\pi$ $a_{00}$: The number of pairs belonging to the different clusters in both $\pi$ and $\rho$ Here, as the accuracy rate of determining whether or not the clusters classified by two different clustering processes agree, Rand index is defined as follows.

$$\frac{a_{11} + a_{00}}{M}. \quad \text{[Equation 16]}$$

It is known, however, that "even when random clustering is done, the Rand index may sometimes have high value" if, for example, the numbers of components in clusters in a dataset are biased. Therefore, more strictly, the following Adjusted Rand Index (ARI) is used.

Figure 32A:
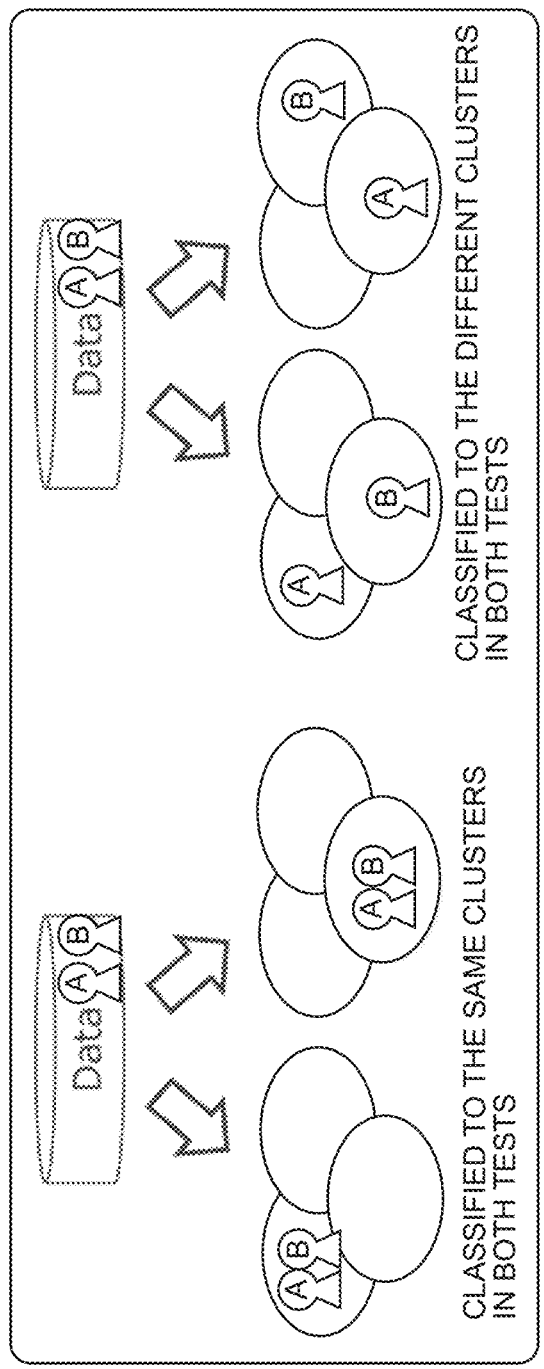
FIG. 32A illustrates a concept of ARI.

FIGS. 32A and 32B illustrate concepts of ARI.

ARI is disclosed, for example, in Reference 22 below. The description of Reference 22 is incorporated herein by reference in its entirety.

Reference 22: Jorge M. Santos and Mark Embrechts, "On the Use of the Adjusted Rand Index as a Metric for Evaluating Supervised Classification", ICANN 2009, Part II, LNCS 5769, pp. 175-184, 2009.

As described above, when the results of two clustering tests are to be applied to the same dataset, the dataset may be classified into the same clusters in both tests, or the dataset may be classified into different clusters in both tests as shown in FIG. 32A. Meanwhile, the dataset may be classified into one same cluster once but to different clusters the next time, as shown in FIG. 32B.

ARI is calculated by first calculating an expected value that a data pair is classified to the same cluster twice or classified to different clusters twice when subjected to two clustering processes, assuming that the two clustering processes are independent from each other, and then subtracting the expected value from the numerator and the denominator of the Rand Index. Therefore, ARI is adjusted to have the value 0 when the clustering processes are not correlated.

$$ARI = \frac{A - E}{\max(A) - E}. \quad \text{[Equation 17]}$$

Here, A represents the number of subject pairs that are [(classified to the same cluster twice over)+(classified to different clusters twice over)] through two different clustering processes, max (A) represents the total number of pairs, and E represents the number of subject pairs having the same results of allocation even though the two clustering processes are independent from each other.

Figure 33B:
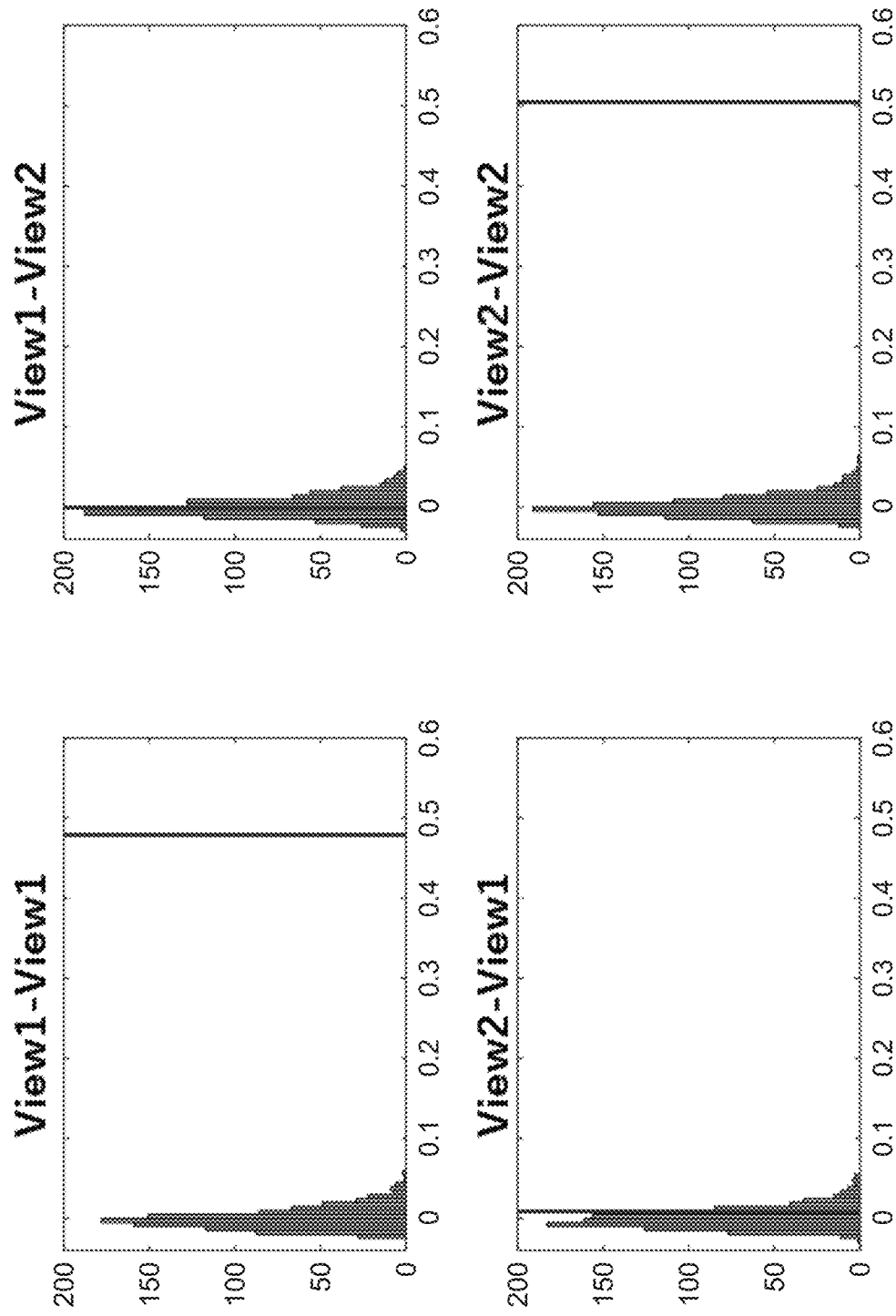
FIG. 33B shows results of similarity evaluation between Clustering 1 and Clustering 1' and Clustering 2 and Clustering 2', showing results of Permutation Test corresponding to FIG. 33A.

FIGS. 33A and 33B show results of similarity evaluation between Clustering 1 and 1' and Clustering 2 and 2', respectively.

FIG. 33A shows, in the form of a table, ARIs for respective views of Datasets 1 and 2.

Regarding Datasets 1 and 2, ARI=0.47 for View 1 and ARI=0.51 for View 2, indicating that there are significant similarities.

FIG. 33B shows results of Permutation Test corresponding to FIG. 33A. As regards Views 1 and 2, as compared with the case in which components are exchanged (represented by the histograms), ARI values (represented by solid lines) are higher with statistical significance in View 1 and View 2.

Permutation Test represents the results of ARI value calculations while cluster attribute labels of subjects are exchanged at random, and the figures show the distributions thereof as histograms when such exchange was conducted a number of times. If similarity between clustering processes is statistically significant, the ARI value between the clustering processes as the object of comparison will have a value higher than when the components are exchanged at random with significance.

From the foregoing, it is determined that clustering processes (stratifications) between the datasets have similarities with significance, or that generalized clustering is realized.

As already described, multiple co-clustering of Dataset 1 and multiple co-clustering of Dataset 2 are both realized in data-driven manner and, therefore, both can serve as a basis for "stratification of patients" using brain functional connectivity links as features.

FIG. 34 shows, in the form of a table, distribution of subjects allocated to respective clusters of View 1 in Clustering 1 and Clustering 1'.

By appropriately rearranging subject cluster indexes, it is possible to distribute most of the subjects near the diagonal of the table, and thus, it can visually be recognized that the two clustering processes are similar to each other.

(Harmonization Process)

In the following, the contents of a process referred to as harmonization in FIG. 6 will be described.

[Harmonization in Accordance with Traveling Subject Method]

The following describes a method used for generating a "disease identifier" and a "clustering process" for stratification, for evaluating a measurement bias and harmonizing measurement data independent of a sampling bias.

FIG. 35 is an illustration showing a method of evaluating the site-to-site differences of subjects (hereinafter referred to as "traveling subjects"), who travel to be subjected to measurements at sites by rs-fcMRI in accordance with the present embodiment.

As will be described later, in the present embodiment, a harmonization method that can remove only the measurement bias by using the traveling subject dataset will be described.

Referring to FIG. 35, in order to evaluate the measurement bias across measurement sites MS.1 to MS.$N_s$, a dataset of travelling subjects TS1 (number of subjects: $N_{ts}$) is obtained.

Assume that the resting state brain activities of $N_{ts}$ healthy participants are imaged at each of the $N_s$ sites, and the $N_s$ sites include all sites where patients' data are imaged.

The obtained dataset of the traveling subjects is stored as the traveling subject data in storage device 210 of data center 200.

Then, as will be described later, the process for the "harmonization of the brain activity biomarkers" is performed by computing system 300.

The traveling subject dataset includes only the healthy cohort. Further, it is assumed that the participants are the same in every site. Therefore, the site-to-site differences in traveling subjects consist only of the "measurement bias."

In the method of harmonization of the present embodiment described in the following, a process of correcting the measurement data at each measurement site by removing the influence of the "measurement bias" as the method of the "harmonization of brain activity biomarkers" is performed.

Specifically, in the following, the "measurement bias" and the "sampling bias" are evaluated using GLMM (Generalized Linear Mixed Model), which is one of the methods of "statistical modeling."

Here, typically, GLM (Generalized Linear Model) incorporates the "explanatory variable" explaining the probability distribution of the "response variable." GLM mainly has three elements, that is, the "probability distribution," the "link function" and the "linear predictor." By designating how to combine these three elements, it is possible to represent various different types of data.

Further, GLMM (Generalized Linear Mixed Model) is a statistical model that allows the incorporation of "individual differences that cannot or is not measured by humans" that cannot be explained by GLM. For example, when objects consist of a number of subsets (for example, subsets taken from different measurement sites), GLMM allows incorporation of the differences in sites in the model. In other words, it is a (mixture) model having a plurality of probability distributions as elements.

By way of example, Reference 23 below discloses GLMM. The disclosure of Reference 23 is hereby incorporated by reference in its entirety.

Reference 23: Takuya KUBO, "Data kaiseki no tameno toukei modeling nyu'mon" (Introduction to statistical modeling for data analysis), Iwanami shoten, 1st edition 2012, 14th edition, 2017.

In the statistical model in accordance with the present embodiment described below, typically, what is referred to as "effect" will be described using the terms "bias" and "factor"; "bias" will be used in the terms "measurement bias" and "sampling bias"; and "factor" will be used in other factors (subject factor or disease factor).

Different from a simple flow of GLMM, in the following, factors are analyzed without discriminating a "fixed effect" from a "random effect." The reason for this is that, generally, when GLMM is used, only the variance is estimated for the random effect and the magnitude of effect of each factor will be unknown. Therefore, in order to evaluate the magnitude of each factor's effect, estimation is done with variables transformed as shown below, so that each factor will have a fixed effect average of zero.

i) The measurement bias of each site is defined as a deviation from the average correlated values for the various functional connectivity across all sites.

ii) Sampling biases of healthy people and patients of mental diseases are assumed to be different from each other. Therefore, the sampling bias of each site will be calculated individually for the healthy cohort and patients' cohorts of various diseases.

iii) Disease factor is defined as a deviation from the value of healthy cohort.

Specifically, in the following, Generalized Linear Mixed Model is applied in the following manner to the dataset including patients and to traveling subjects' dataset.

Assume that there are $N_{ts}$ traveling subjects, and of $N_s$ measurement sites, $N_{sh}$ represents the number of sites where the measurement of healthy people was done, and $N_{ds}$ represents the number of sites where the measurement of patients of a certain disease (here, represented by a suffix "dis") was done.

Participant factor (p), measurement bias (m), sampling biases ($S_{hc}$, $S_{dis}$) and mental disease factor (d) are evaluated by fitting a regression model to the correlation values of the functional connectivity of all participants, from the measurement result dataset of patients and the traveling subjects' dataset.

In the following, a vector is denoted by a small letter (for example, m), and it is assumed that every vector is a column vector.

A vector element is denoted by a suffix such as $m_k$.

A regression model of a functional connectivity vector (assumed to be a column vector) consisting of n correlation values among brain areas is represented as follows.

Connectivity = [Equation 18]

$$x_m^T m + x_{Shc}^T s_{hc} + x_{Sdis}^T s_{dis} + x_d^T d + x_p^T p + const + e,$$

$$\sum_j p_j = 0, \sum_k m_k = 0, \sum_k s_{hck} = 0, \sum_k s_{disk} = 0, d_1(HC) = 0.$$

In order to represent characteristics of each participant, a binary code system of 1-of-k is used, and every target vector (for example, $x_m$) for a measurement bias m belonging to a site k has elements all equal to zero except for the element k that is equal to one.

If a participant does not belong to any class (healthy people, patient, traveling subject), the target vector will be a vector of which elements are all equal to zero.

Upper suffix T represents transpose of matrix or vector and $x^T$ represents a row vector.

Here, m represents the measurement bias (column vector of $N_s \times 1$), $s_{hc}$ represents the sample vector of healthy cohort (column vector of $N_{sh} \times 1$), $s_{dis}$ represents the sampling bias of a patient (column vector of $N_{sd} \times 1$), d represents the disease factor (column vector of 2×1, having healthy and disease as elements), p represents the participant factor (column vector of $N_{ts} \times 1$), const represents an average of functional connectivity of all participants (including healthy people, patients and traveling subjects) at all measurement sites, and e~N (0, $\gamma^{-1}$) represents noise.

Here, for simplicity of description, only one type of disease is assumed. An example involving a plurality of diseases will be described later.

As to the correlation value of each functional connectivity, the design matrix of the regression model does not have sufficient rank and, therefore, respective parameters are evaluated using the least square regression by L2 normalization. Other than the least square regression by L2 normalization, a different method of evaluation such as Bayesian estimation may be used.

After the above-described regression calculation, b-th connectivity of a subject a can be given as:

$$\text{Connectivity}_{a,b} = x_m^{a^T} m^b + x_{Shc}^{a^T} s_{hc}^b + x_{Sdis}^{a^T} s_{dis}^b + x_d^{a^T} d^b + x_p^{a^T} p^b + const + e.$$
[Equation 19]

Figure 36:
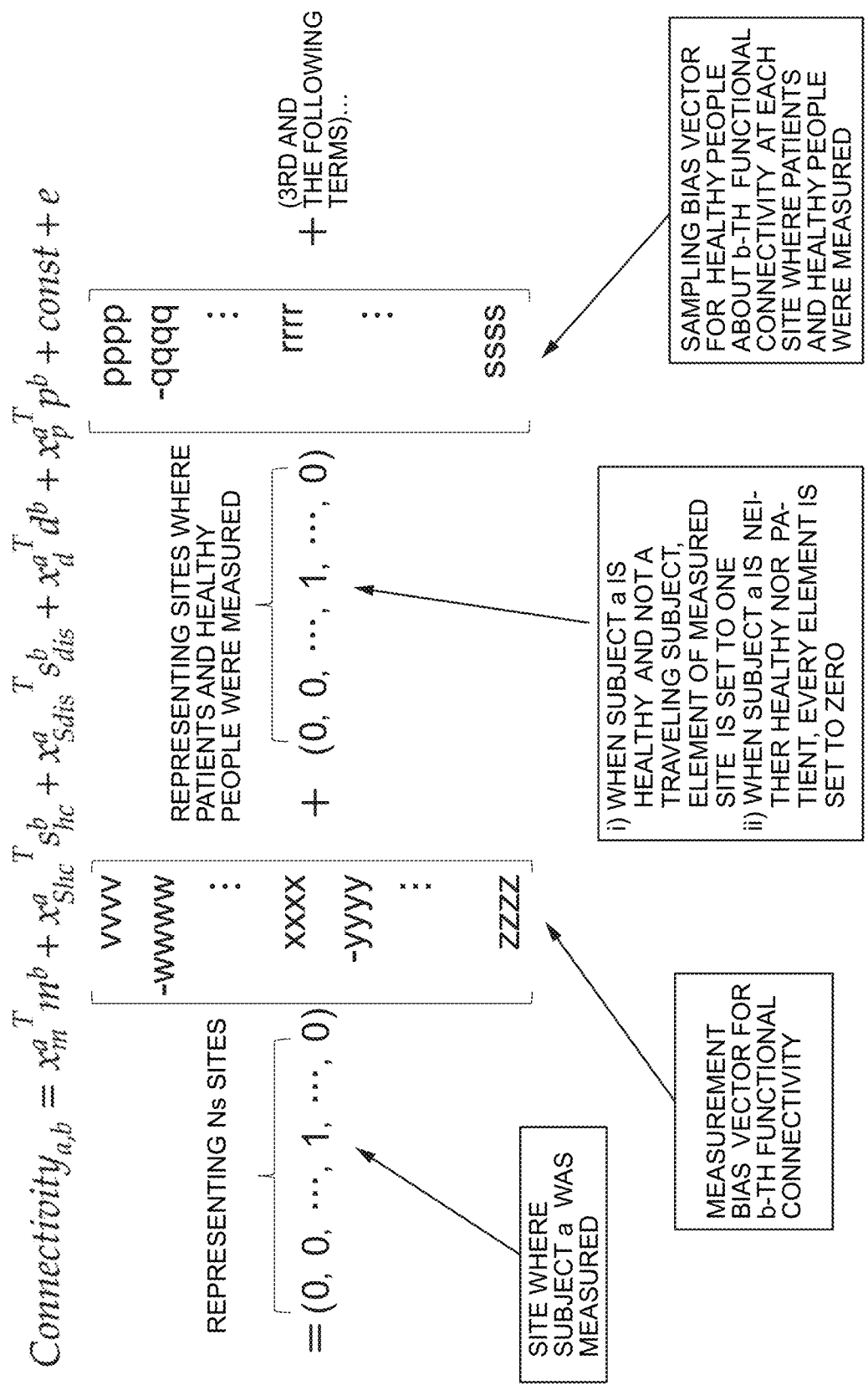

FIG. 36 is an illustration showing how to express b-th functional connectivity of a subject a.

FIG. 36 shows the meanings of target vectors of the first term and the second term as well as the measurement bias vector and the sampling bias vector of a healthy subject.

The same applies to the third and the following terms.

(Process Flow of Harmonization)

Figure 37:
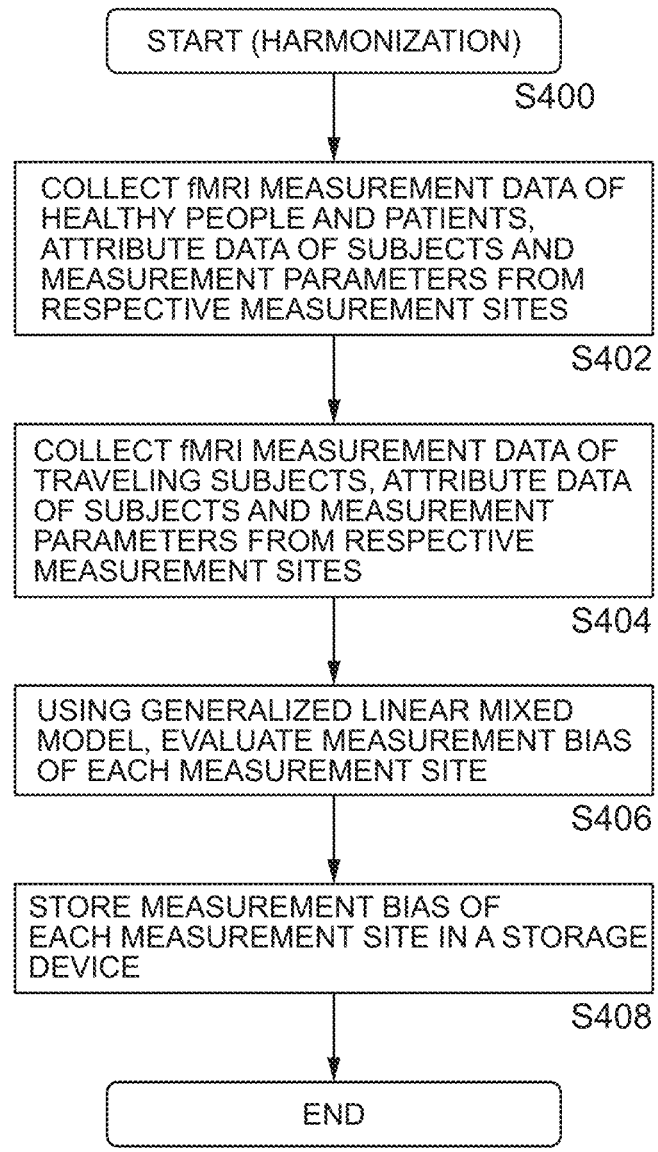
FIG. 37 is a flowchart showing a process of calculating a measurement bias for harmonization.

FIG. 37 is a flowchart showing a process of calculating a measurement bias for harmonization.

First, fMRI measurement data of subjects (healthy people and patients), attribute data of subjects and measurement parameters are collected from respective measurement sites to storage device 210 of data center 200 (FIG. 37 S402).

Thereafter, brain activities of traveling subject TS1 are measured while the subject travels from measurement site to measurement site, though not limiting, in a prescribed period (for example, in a one-year period) and the fMRI measurement data of the traveling subject, attribute data of the subject and measurement parameters are collected from respective measurement sites to storage device 210 of data center 200 (FIG. 37 S404).

Using GLMM (Generalized Linear Mixed Model) as described above, the harmonization calculating unit 3020 evaluates the measurement bias of each measurement site with respect to the functional connectivity (FIG. 37 S406).

The harmonization calculating unit 3020 stores the measurement bias of each measurement site calculated in this manner in storage device 2080, as measurement bias data 3108 (FIG. 37 S408).

(Harmonization in Discriminator Generating Process)

Harmonization of brain functional connectivity values in the process of generating a disease identifier for disease or healthy label for the subjects by discriminating unit 3000 will be briefly described.

Such a disease identifier provides assisting information (support information) for diagnosing a subject.

A correlation value correcting unit 3004 reads measurement bias data 3108 of each measurement site stored in storage device 2080, and for the off-diagonal components of the correlation matrix of each subject as the object of training for machine learning to generate a disease identifier, performs the harmonization process in accordance with the equation below.

$$C_{sub} = \text{Connectivity} - x_m^T \hat{m}.$$
[Equation 20]

Here, functional connectivity "Connectivity" represents the functional connectivity before harmonization, and $C_{sub}$ represents the functional connectivity after harmonization. Further, m (hat) (a character x with "^" above will be referred to as "x (hat)") represents the measurement bias at a measurement site evaluated by the least square regression by L2 normalization as described above. Thus, the measurement bias corresponding to the measurement site at which functional connectivity has been measured will be subtracted from the functional connectivity "Connectivity", and hence, subjected to the harmonization process.

Data after the correction is stored as corrected correlation value data 3110 in storage device 2080.

As is described in the Reference 24 below, it is reasonable to assume that the disease factor relates not to the connectivity of the whole brain but to a specific subset of connectivity. Disclosure of Reference 24 below is incorporated herein by reference in its entirety.

Reference 24: Yahata N, et al. A small number of abnormal brain connections predicts adult autism spectrum disorder. Nat Commun 7, 11254 (2016).

Therefore, thereafter, disease identifier generator 3008 performs learning with feature selection as described above on the disease label of the subject including the diseased/healthy label of the subject and the corrected functional connectivity, and thus generates a disease identifier.

The method of performing feature selection and modeling while suppressing over-fitting is not limited to the regularized logistic regression by LASSO, and other methods such as the sparse logistic regression disclosed in Reference 25 below or other sparse Bayesian method may be used. Disclosure of Reference 25 below is incorporated herein by reference in its entirety.

Reference 25: Okito Yamashita, Masaaki Sato, Taku Yoshioka, Frank Tong, and Yukiyasu Kamitani. "Sparse Estimation automatically selects voxels relevant for the decoding of fMRT activity patterns." NeuroImage, Vol. 42, No. 4, pp. 1414-1429, 2008.

As described above, a disease identifier (functioning as a discriminator for diagnosis based on the brain activity biomarker) is generated, and disease identifier generator 3008 stores information for specifying the discriminator as disease identifier data 3112 in storage device 2080.

Though not limiting, the above-described process may be done once in every prescribed period (for example, once a year).

Assume that measurement of functional connectivity is performed for a new subject at any of the measurement sites. It is possible to presume that the measurement bias of this measurement site is constant for a prescribed time period. Therefore, discrimination value calculator 3012 subtracts, from values of the correlation matrix components of input data of the subject, the "measurement bias" corresponding to the measurement site at which the input data is measured, which bias has been already calculated by the above-described procedure, and thus, performs the harmonization process. Then, the "disease identifier" that has been already generated by the above-described procedure, outputs a discrimination label for the subject as the discrimination result.

The discrimination result may be a value indicating either one of "diseased" and "healthy," or it may be a value indicating probability of at least one of "diseased" and "healthy."

Regarding the discrimination process performed by the discrimination value calculator 3012, the "input data" may be the MRI measurement data themselves representing the brain function activities of the subject, or the data of correlation values as off-diagonal components of the correlation matrix after the values of the correlation matrix are calculated from the MRI measurement data representing the brain function activities of the subject at each measurement site.

(Harmonization Calculating Process when a New Measurement Site is Added)

Figure 38:
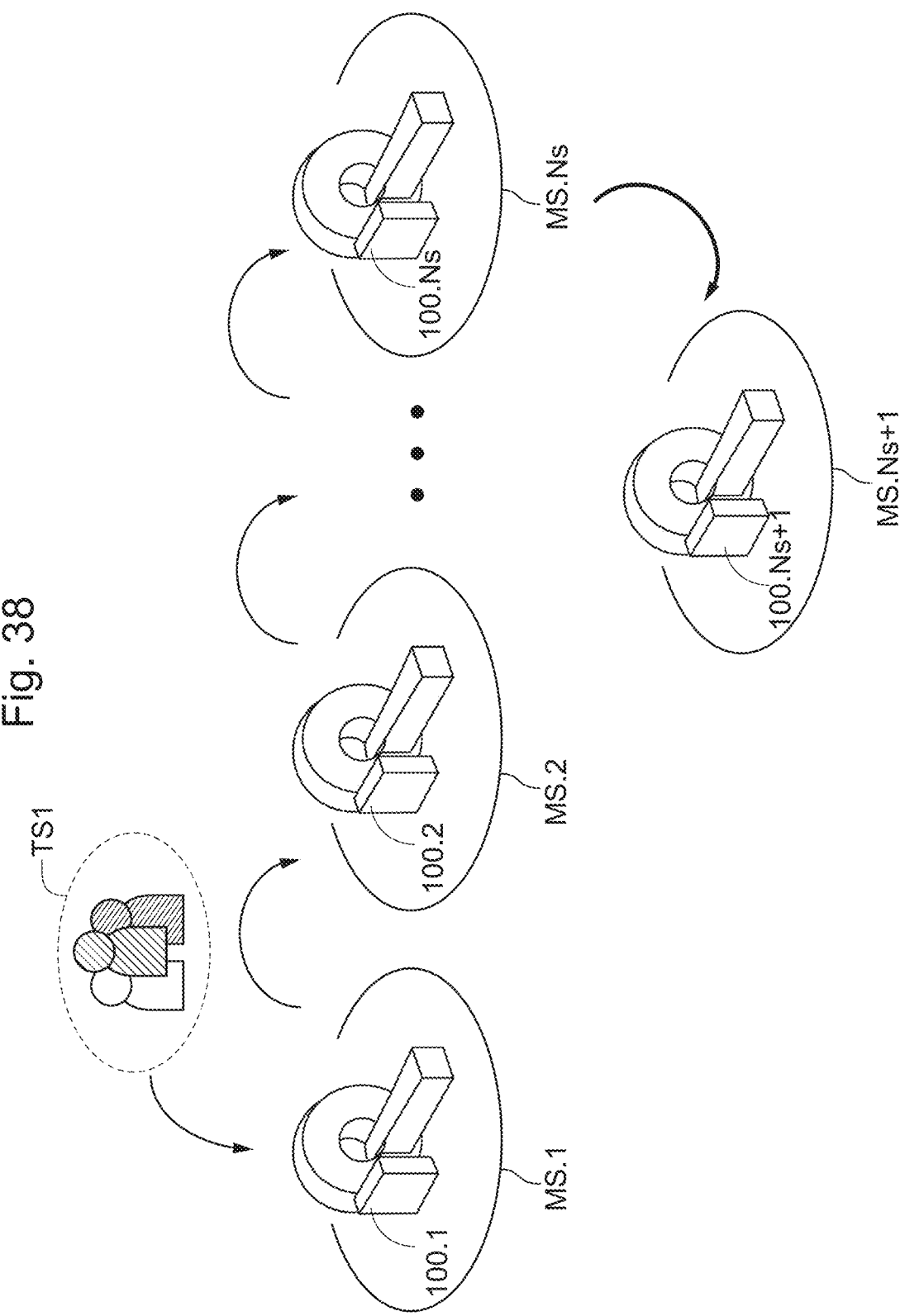
FIG. 38 illustrates a process of calculating a measurement bias for harmonization process when a new measurement site is added.

FIG. 38 is a schematic diagram illustrating a process for calculating a measurement bias for the harmonization process when a new measurement site is added after the measurement bias for a harmonization process was performed by the procedure described with reference to FIG. 37.

Referring to FIG. 38, assume that a $(N_s+1)$-th measurement site $MS.N_s+1$ is newly added. In this case, it is possible to cause the traveling subject or subjects TS1 to newly circulate all of the $(N_s+1)$ measurement sites, to perform the same harmonization calculating process described above, and to newly calculate the measurement biases.

By the system that performs the process as described above, it is possible to adjust and correct the measurement bias at each facility as regards the brain activity measurement data obtained at a plurality of different facilities. Thus, it becomes possible to adjust the brain functional connectivity correlation values based on the measurement data obtained at a plurality of facilities.

Further, by the system performing the process according to the present embodiment, it is possible to realize a brain activity classifier harmonizing method, a brain activity classifier harmonizing system, a brain activity analyzing system and a brain activity analyzing method, that can harmonize the measurement data of the brain activities measured at a plurality of facilities and thus can provide data for objectively determining healthy or diseased state.

Further, by the system performing the process according to the present embodiment, it is possible to realize a biomarker device based on the brain functional imaging and a program for the biomarker device on neurological/mental diseases, in connection with the measurement data of the brain activities measured at a plurality of facilities.

[Modification of the First Embodiment]

In the foregoing description, the harmonization calculating process has been described on the premise that the following subject data are obtained.
i) patients' data
ii) healthy people's data
iii) traveling subjects' data If the object is only to evaluate the "measurement bias," however, the "measurement bias" may be evaluated by the GLMM (Generalized Linear Mixed Model), based on the measurement data of the traveling subjects.

Specifically, assume that there are $N_{ts}$ traveling subjects.

The participant factor (p) and the measurement bias (m) are evaluated by applying the regression model to the functional connectivity correlation values of all the participants from the traveling subject dataset.

Here again, a vector is represented by a small letter (for example m), and it is assumed that every vector is a column vector.

A vector element is denoted by a suffix such as $m_k$.

A regression model of a functional connectivity vector (assumed to be a column vector) consisting of n correlation values among the brain areas is represented as follows.

$$\text{Connectivity} = x_m^T m + x_p^T p + const + e, \sum_j^{N_{ts}} p_j = 0, \sum_k^{N_s} m_k = 0. \quad \text{[Equation 21]}$$

In order to represent the characteristics of each participant, a binary code system of 1-of-k is used, and every target vector (for example, $x_m$) for a measurement bias m belonging to a site k has elements all equal to zero except for the element k that is equal to one.

Upper suffix T represents transpose of a matrix or a vector and $x^T$ represents a column vector.

It is possible to calculate the "measurement bias" by the approach above and to perform the harmonization process.

The difference between the method of the first embodiment and the method of the modification of the first embodiment is that when the traveling subjects only are used as in the method of the modification, it becomes unnecessary to take into account the sampling bias. On the other hand, the method of the first embodiment is advantageous in that a larger amount of data used for estimation can be used, as patients' data and healthy people's data are both available.

Therefore, there is a trade-off between the improvement in the estimation precision of the measurement bias attained by not considering the sampling bias and the improvement in the estimation precision of the measurement bias attained by a larger amount of data.

Therefore, though not limiting, it is possible to experimentally optimize the amount of data of participants (patients and healthy people) used at each measurement site in practical operation. In that case, though not limiting, it is possible to allot beforehand the number of participants to be extracted from each measurement site, and at each measurement site, data of the allotted number of participants may be extracted at random.

[Data and Analysis of Actual Results of Brain Activity Measurements]

The following description gives the results of the above-described harmonization process actually applied to data of publicly available multi-disease database.

Figure 39A:
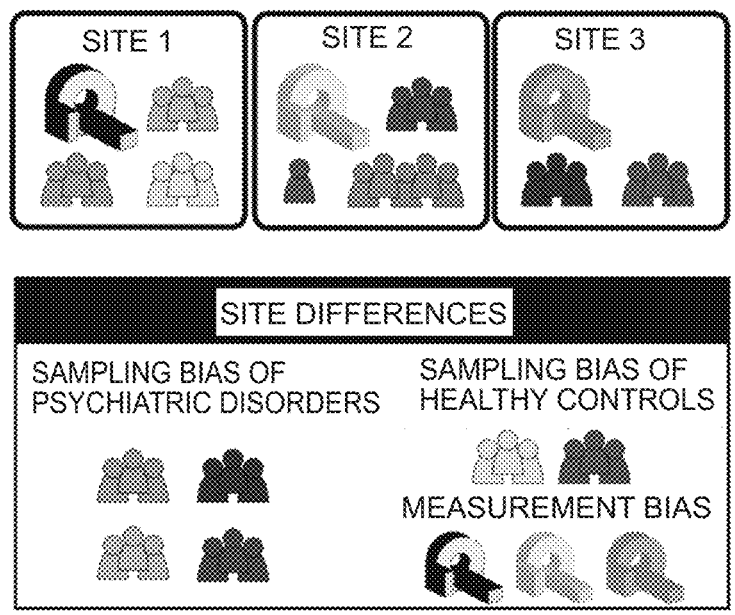
FIG. 39A shows a dataset of multi-disease database used in the harmonization process.
Figure 39B:
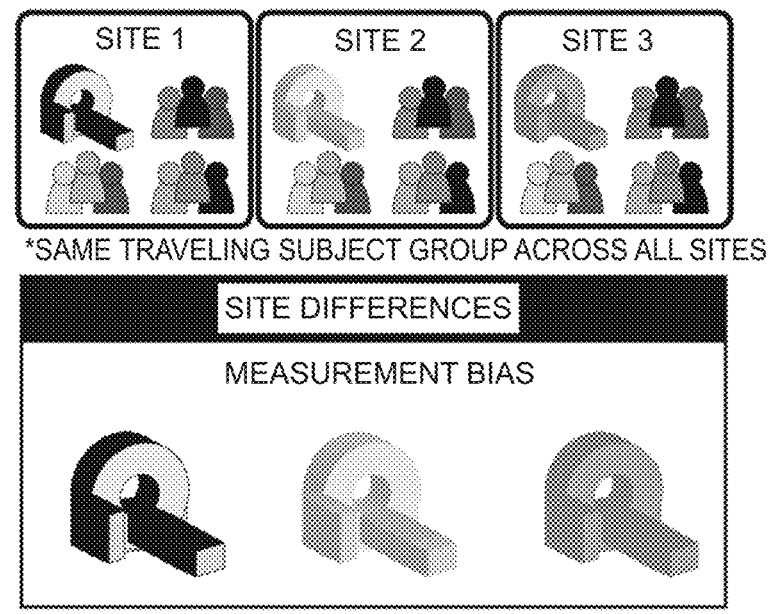
FIG. 39B shows a traveling subject dataset used in the harmonization process.

FIGS. 39A and 39B are illustrations showing data of multi-disease database and the traveling subject dataset used for the harmonization process.

As shown in FIG. 39A, we use datasets of patients' cohort and healthy cohort in data publicly available as multi-disease database (https://bicr-resource.atr.jp/decnefpro/) at Strategic Research Program for Brain Science (SRPBS).

The data measured at a plurality of measurement sites (Site 1, Site 2 and Site 3 are representatively shown in FIG. 39A) as multi-disease dataset includes, as the site-to-site differences, a sampling bias of patients of mental diseases, a sampling bias of healthy people, and the measurement bias.

On the other hand, as is shown in FIG. 39B, the data measured at a plurality of measurement sites (Site 1, Site 2 and Site 3 are representatively shown in FIG. 39B) as traveling subject dataset includes, as the site-to-site differences, only the measurement bias.

By simultaneous analysis of the datasets, it is possible to divide the site-to-site differences to the measurement bias and the sampling biases, and effect sizes of these on the resting state functional connectivity are quantitatively compared with those of the mental disease.

As to the measurement bias, the effect sizes of different imaging parameters, the manufacturers of MRI devices, and the number of reception coils in the MRI scanners were quantitatively compared.

In order to overcome such limitations related to the site-to-site differences, the harmonization method that can remove only the measurement bias is performed, using the traveling subject dataset.

Regression models of subject information (attribute) (for example, age) and mental disease biomarkers were built based on the resting state functional connectivity MRI data obtained at a plurality of sites and harmonized by the newly proposed method and by an existing method.

We studied variation in performance of these prediction models based on the methods of harmonization.

(Datasets Used)

The following three datasets of resting state functional MRI were used;
(1) multi-disease dataset of SRPBS;
(2) dataset of 19 traveling subjects; and
(3) independent validation dataset.

(Multi-Disease Dataset of SRPBS)

Figure 40:
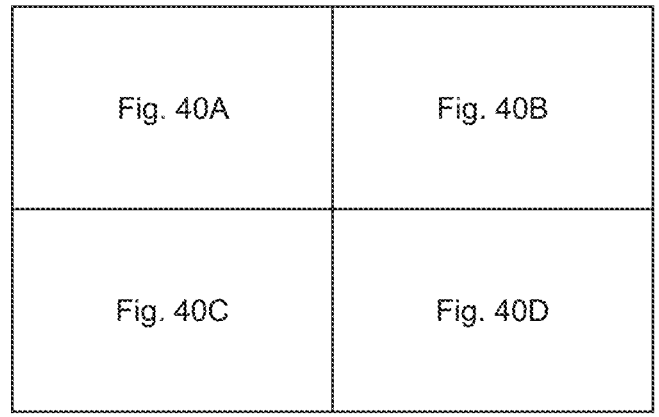
FIG. 40 shows contents of a multi-disease dataset of SRPBS.

FIG. 40 (FIGS. 40A to 40D) shows contents of a multi-disease dataset of SRPBS.

This dataset includes patients of five different diseases and a healthy control cohort (HCs) diagnosed at nine sites, and contains data of the following 805 participants in total:
  482 healthy people from nine sites;
  161 patients of major depressive disorders (MDD) from five sites;
  49 patients of autism (ASD) from one site;
  65 patients of obsessive-compulsive disorder (OCD) from one site; and
  48 patients of schizophrenic disorder (SCZ) from three sites.

Figure 41:
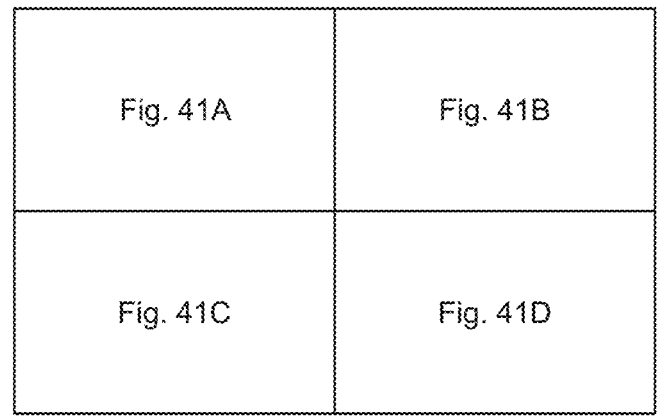
FIG. 41 shows imaging protocols at various measurement sites.

FIG. 41 (FIGS. 41A to 41D) shows imaging protocols at various measurement sites.

The resting state functional MRI data were obtained using standardized imaging protocols except for three sites (http://www.cns.atr.jp/rs-fmri-protocol-2/).

The site-to-site differences of this dataset included both the measurement and the sampling biases.

For evaluating biases, only the data obtained by using the standardized protocol was used.

The OCD patients were not scanned using the standardized protocol and, hence, the disease factor of OCD was not evaluated.

Reference characters in the table are as follows.
  ATT: Siemens TimTrio Scanner at Advanced Telecommunications Research Institute.
  ATV: Siemens Verio Scanner at Advanced Telecommunications Research Institute.
  KUT: Siemens TimTrio Scanner at Kyoto University
  SWA: Showa University
  HUH: Hiroshima University Hospital
  HKH: Hiroshima Kajikawa Hospital
  COI: COI (Hiroshima University)
  KPM: Kyoto Prefectural University of Medicine
  UTO: University of Tokyo
  ASD: Autism Spectrum Disorder
  MDD: Major Depressive Disorder
  OCD: Obsessive Compulsive Disorder
  SCZ: Schizophrenia
  SIE: Siemens fMRI device
  GE: GE fMRI device
  PHI: Philips fMRI device (Traveling Subjects' Dataset)

In order to evaluate the measurement bias across the measurement sites in the SRPBS dataset, the traveling subjects' dataset was obtained.

Healthy nine participants (all male; age 24-32; average age 27±2.6) were imaged at each of 12 sites, which sites included nine sites that imaged SRPBS datasets, and a total of 411 operation sessions were held.

While we tried to acquire the dataset by using the same imaging protocol as that for multi-disease dataset of SRPBS, due to the limitations of the parameter settings of respective sites or the limitations of conventional scanning conditions, the image protocols differ to some extent from site to site.

The differences were, for example, as follows: two directions of phase encoding (P→A and A→P); three different MRI manufacturers (Siemens, GE and Philips); four different numbers of coil channels (8, 12, 24 and 32); and seven scanner types (TimTrio, Verio, Skyra, Spectrum, MR750W, SignaHDxt and Achieva).

Since the same nine participants were imaged at 12 sites, the site-to-site differences of the dataset included only the measurement bias.

(Independent Validation Dataset)

In order to validate the generalizing performance of a model of predicting the participants' age and mental disease classifier based on the resting state functional connectivity MRI data, we obtained data of an independent validation cohort covering two diseases and seven sites.

The data was obtained from a total of 625 participants.

Specifically, data was obtained from 476 healthy controls (HCs) from six sites, 93 patients of MDD from two sites, and 56 patients of SCZ from one site.

(Visualization of Site-to-Site Differences and Disease Effect)

First, by Principal Component Analysis (PCA), the site-to-site differences and disease effect in the SRPBS multi-disease dataset of the resting state functional connectivity MRI were visualized.

Figure 42:
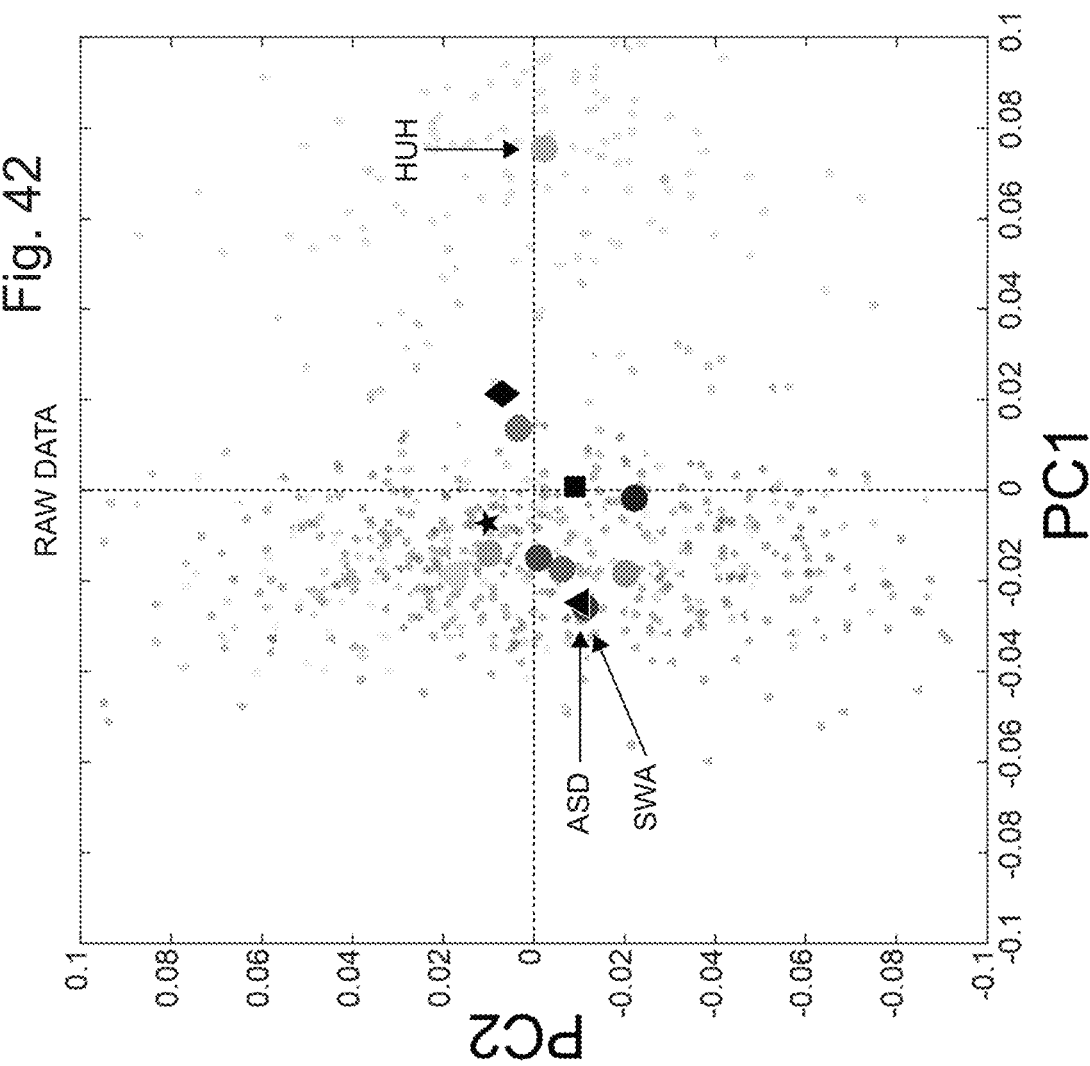
FIG. 42 is a graph visualizing the site-to-site differences and disease effects based on principal component analysis.

FIG. 42 is a graph visualizing the site-to-site differences and the disease effects based on the principal component analysis.

Here, the principal component analysis corresponds to the unsupervised dimensionality reduction method.

The functional connectivity of a subject was calculated as the time-wise correlation (using Pearson's correlation coefficient) of the blood oxygen level dependent (BOLD) signal of the resting state MRI between two brain regions, for each participant.

Functional connectivity is defined based on a functional brain map consisting of 268 nodes (or brain regions) covering the entire brain.

Of a matrix representing the correlation of functional connectivity, 35,778 (that is, (268×267)/2) values of connection strength (connectivity) of the lower triangular part of the matrix are used.

As shown in FIG. 42, the participants' data in the SRPBS multi-disease dataset were all plotted on two axes consisting of the first two principal components.

Specifically, all participants of the SRPBS multi-disease dataset are projected on the first two principal components (PC) as represented by small, light-colored markers.

The principal component 1 was separated by the HUH site so clearly that almost all the data variance could be explained.

Patients of ASD were scanned only at the SWA site. Therefore, the average of the patients of ASD (▲) and that of the healthy controls HCs (●) scanned at this site were plotted almost on the same position.

FIG. 42 shows the dimensional reduction by the PCA in the multi-disease dataset.

(Bias Evaluation)

In order to quantitatively study the site-to-site differences of the resting state functional connectivity MRI data, the measurement bias, the sampling bias and the diagnosis factor were specified.

As described above, the measurement bias of each site was defined as a deviation from an average across all sites of the correlation values for each functional connectivity. It is assumed that the sampling bias of healthy people differs from that of patients of mental disease.

Therefore, the sampling bias of each site was calculated individually for the cohort of healthy controls and the cohorts of patients of each disease.

The disease factors were defined as deviations from the values of healthy controls.

Sampling biases were estimated for patients with MDD and SCZ because only these patients were sampled at multiple sites.

In contrast, the traveling subjects' dataset included only the measurement bias, because the participants were fixed.

By combining the traveling subjects with the SRPBS multi-disease dataset, the sampling and measurement biases were estimated simultaneously, as different factors are affected by different sites. In order to evaluate the effect of disease factor and both types of biases on the functional connectivity, the "Linear Mixed-Effects Model" was used as described in the following.

(Linear Mixed-Effects Model on SRPBS Multi-Disease Dataset)

In the linear mixed-effects model, the correlation value of connectivity of each subject in the SRPBS multi-disease dataset consists of a fixed effect and a random effect.

The fixed effect includes the average correlation value over all participants and across all sites as the base line, and a sum of the measurement bias, the sampling bias and the disease factor.

The effect as a combination of the participant's factor (individual difference) and the scan-to-scan variation is regarded as the random effect.

(Details of Bias and Factor Evaluation)

The participant factor (p), the measurement bias (m), the sampling biases ($s_{hc}$, $s_{mdd}$, $s_{scz}$) and the mental disease factor (d) were evaluated by fitting a regression model to the correlation values of functional connectivity of all participants from the SRPBS multi-disease dataset and the traveling subjects' dataset.

In the following, a vector is denoted by a small letter (for example, m), and it is assumed that every vector is a column vector.

A vector element is denoted by a suffix such as $m_k$.

As described above, in order to represent the characteristics of each participant, a binary code system of 1-of-k is used, and every target vector (for example, $x_m$) for a measurement bias m belonging to a site k has elements all equal to zero except for the element k that is equal to one.

If a participant does not belong to any class, the target vector will be a vector with all elements equal to zero.

Upper suffix T represents transpose of matrix or vector and $x^T$ represents a row vector.

For each connectivity, the regression model can be represented as:

$$\text{Connectivity} = x_m^T m + x_{Shc}^T s_{hc} + \qquad \text{[Equation 22]}$$
$$x_{mdd}^T s_{mdd} + x_{Sscz}^T s_{scz} + x_d^T d + x_p^T p + + const + e,$$
$$\sum_j^9 p_j = 0, \sum_k^{12} m_k = 0, \sum_k^6 s_{hc\,k} = 0, \sum_k^3 s_{mdd\,k} = 0, \sum_k^3 s_{scz\,k} = 0, d_1(HC) = 0.$$

Here, m represents the measurement bias (12 sites×one), $s_{hc}$ represents the sample vector of healthy controls (six sites×one), $s_{mdd}$ represents the sampling bias of patients with MDD (three sites×one), $s_{scz}$ represents the sampling bias of patients with SCZ (three sites×one), d represents the disease factor (three diseases×one), p represents the participant factor (nine traveling subjects×one), const represents the average functional connectivity value across all participants from all measurement sites, and e~N (0, $\gamma^{-1}$) represents noise.

As to the correlation value of each functional connectivity, the respective parameters are evaluated using the least square regression by L2 normalization.

Where normalization was not applied, spurious anticorrelation between the measurement bias and the sampling bias for the group of healthy controls, as well as spurious correlation between the sampling bias for the group of healthy controls and the sampling bias for the patients of mental disease were observed. In order to minimize the absolute average value of these spurious correlations, hyper parameter lambda adjustment was conducted.

(Linear Mixed-Effects Model on Traveling Subjects' Dataset)

In the linear mixed-effects model on the traveling subjects' dataset, the correlation value of connectivity of each subject for a specific scan in the traveling subjects' dataset consists of a fixed effect and a random effect.

The fixed effect includes the average correlation value over all participants and across all sites, and a sum of the participant factor and the measurement bias.

Scan-to-scan variation was regarded as a random effect.

For each participant, the participant factor was defined as a deviation of the brain functional connectivity correlation value from the average of all participants.

By fitting the above-described two regression models simultaneously to the functional connectivity correlation values of two different datasets, all biases and factors were evaluated.

In summary, biases and factors were evaluated as vectors including dimensions reflecting the number of connectivity correlation values (that is, 35,778).

(Analysis of Contribution Size)

In order to quantitatively verify the magnitude relationship among factors, contribution sizes were calculated and compared in the linear mixed-effects model to determine the extent to which each bias type and factor explains the variance of the data.

$$\text{Connectivity}_{a,b} = x_m^{a^T} m^b + x_{s_{hc}}^{a^T} s_{hc}^b + x_{s_{mdd}}^{a^T} s_{mdd}^b + x_{s_{scz}}^{a^T} s_{scz}^b + x_d^{a^T} d^b + x_p^{a^T} p^b + \text{const} + e.$$ [Equation 23]

By way of example, in this model, the contribution size of the measurement bias (the first term) was calculated as follows:

$$\text{Contribution size}_m = \frac{1}{N_m} \frac{1}{N_s \times N} \sum_{a=1}^{N_s} \sum_{b=1}^{N} \frac{(x_m^{a^T} m^b)^2}{(x_m^{a^T} m^b)^2 + (x_{s_{hc}}^{a^T} s_{hc}^b)^2 + (x_{s_{mdd}}^{a^T} s_{mdd}^b)^2 + (x_{s_{scz}}^{a^T} s_{scz}^b)^2 + (x_d^{a^T} d^b)^2 + (x_p^{a^T} p^b)^2 + e^2}.$$ [Equation 24]

Here, $N_m$ represents the number of components for each factor, N represents the number of connectivity, $N_s$ represents the number of subjects, and Contribution size$_m$ represents the magnitude of the contribution size of measurement bias.

These equations were used for evaluating the contribution size of individual factor related to the measurement bias (for example, phase encoding direction, scanner, coil and fMRI manufacturer).

Particularly, the measurement bias was broken down to these factors and thereafter, related parameter was evaluated.

Other parameters were fixed to values evaluated before.

Findings from the contribution size evaluation are as follows.

1) The effect size of measurement bias on functional connectivity is shown to be smaller than that of the participant factor but is mostly larger than the disease factors, suggesting that the measurement bias could be a serious limitation in research regarding mental diseases.

2) The largest variance of the sampling bias is significantly larger than the variance of the MDD factor, and the smallest variance of the sampling bias was ½ of the variance of the disease factor.

This also suggests that the measurement bias could be a serious limitation in research regarding mental diseases.

3) Standard deviation of the participant factor was about twice the standard deviation of the disease factors of SCZ, MDD and ASD. Therefore, individual fluctuation in the population of healthy people was larger than among the patients of SCZ, MDD and ASD, when all functional connectivity is considered.

4) Further, in most cases, the standard deviation of the measurement bias was larger than the standard deviation of disease factors, while the standard deviation of the sampling bias was comparable to the standard deviation of the disease factors.

Such a relation makes it very difficult to develop a classifier based on the resting state functional connectivity MRI directed to mental diseases or developmental difficulty. Generation of a classifier that is robust and generalizable across multiple sites becomes possible only when an abnormal functional connectivity that is site-independent and specific to a small number of very rare diseases can be selected from a large number of connections.

(Hierarchical Clustering Analysis for Measurement Bias)

For each site k, Pearson's correlation coefficients among measurement biases $m_k$ (N×1, here N is the number of functional connectivity) were calculated and hierarchical clustering analysis was conducted based on the correlation coefficients across the measurement biases.

Figure 43:
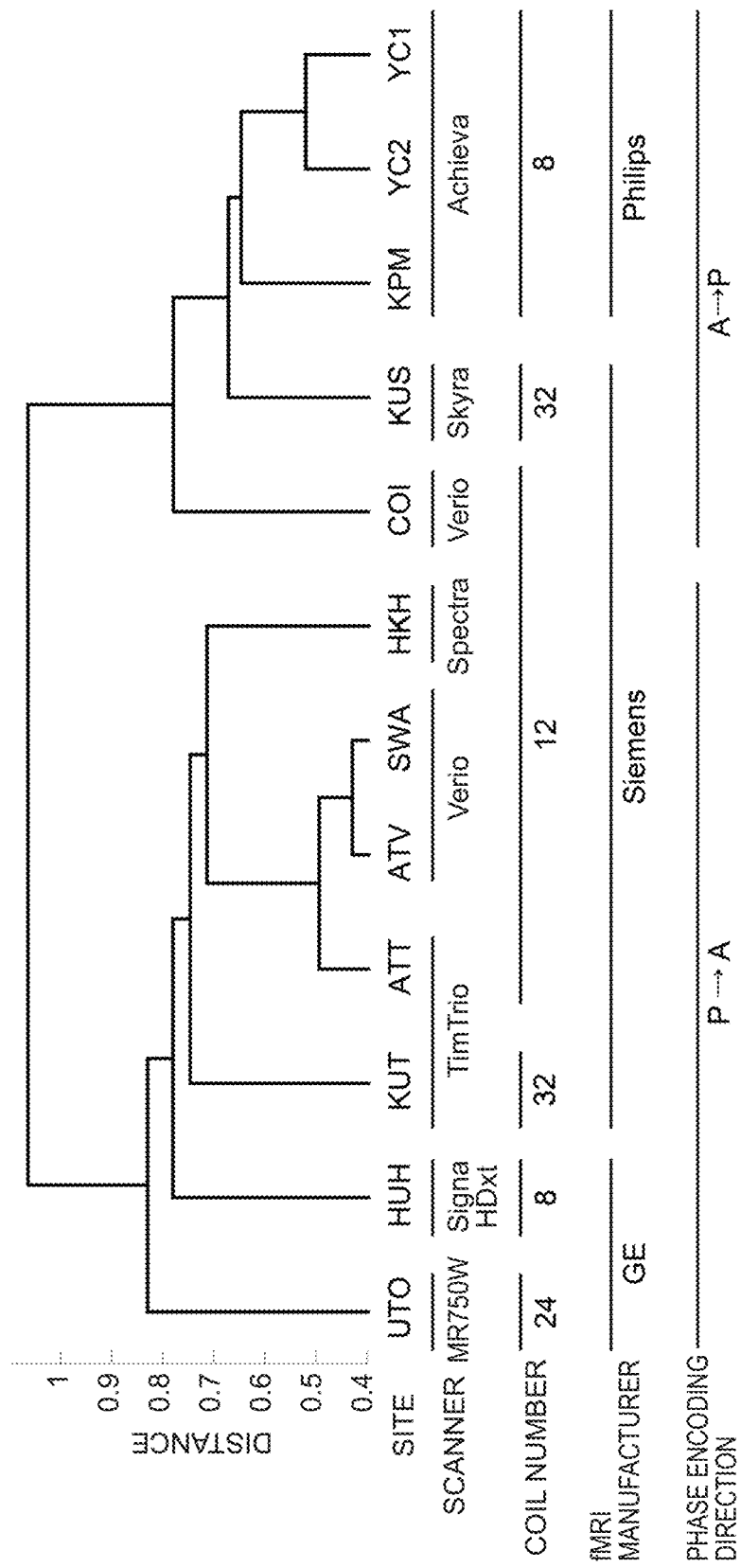
FIG. 43 is a tree diagram based on a hierarchical clustering analysis.

FIG. 43 is a tree diagram derived from the hierarchical clustering analysis.

The height of each linkage in the tree diagram represents dissimilarity (1-$r$) between the clusters coupled by that link.

While studying the characteristics of measurement biases, we examined whether or not the similarity of the measurement bias vectors evaluated for 12 sites reflected specific characteristics of the MRI scanners such as the direction of the phase encoding, the MRI manufacturer, the coil type and the scanner type.

In order to find clusters having the same pattern on the measurement biases, we used the hierarchical cluster analysis.

As a result, as is shown in FIG. 43, measurement biases of the 12 sites were divided into clusters of phase encoding directions at the first level.

At the second level, the measurement biases were divided into fMRI manufacturer clusters, and then further divided into coil type clusters followed by scanner model clusters.

Figure 44:
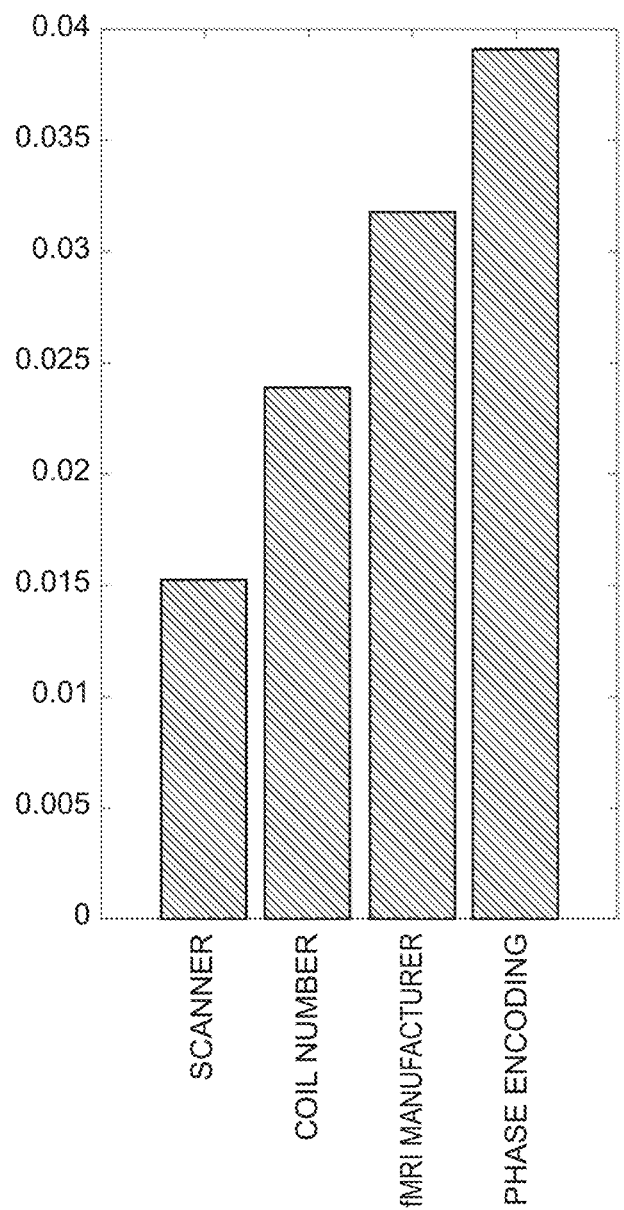
FIG. 44 shows the contribution size of each factor.

FIG. 44 shows the contribution size of each factor.

As shown in FIG. 44, in order to evaluate the contribution of each factor, the magnitude relation of the factors was quantitatively confirmed by using the same model.

The contribution size was the largest for the phase encoding directions (0.0391), followed by the fMRI manufacturers (0.0318), coil types (0.0239) and scanner models (0.0152).

These findings indicate that the main factor influencing measurement bias is the difference in the phase encoding directions, followed by the differences in the fMRI manufacturers, coil types and scanner models.

(Visualization of Harmonization Effect)

Next, we will describe the method of harmonization that allows the removal of the measurement bias only, using the traveling subjects' dataset.

As described above, using the Linear Mixed-Effects Model, measurement bias was evaluated separately from the sampling bias.

By this method, it is possible to remove measurement bias alone from the SRPBS multi-disease dataset, and to maintain sampling bias containing biological information.

(Harmonization of Traveling Subjects)

The phase encoding direction at the HKH site was different between the SRPBS multi-disease dataset and the traveling subject dataset. Therefore, in order to evaluate measurement biases, in the following, separate from the measurement biases, a phase encode factor ($pa_q$) was introduced in the Equation below.

The measurement biases and the phase encode factor were evaluated by applying the regression model to the SRPBS multi-disease dataset and the traveling subject dataset coupled together.

The regression model is as follows:

$$\text{Connectivity} = x_m^T m + x_{Shc}^T s_{hc} + x_{mdd}^T s_{mdd} + \quad \text{[Equation 25]}$$

$$x_{Sscz}^T s_{scz} + x_d^T d + x_p^T p + x_{pa}^T pa + const + e,$$

$$\sum_j^9 p_j = 0, \sum_k^{12} m_k = 0, \sum_k^6 s_{hck} = 0, \sum_k^3 s_{mddk} = 0,$$

$$\sum_k^3 s_{sczk} = 0, d_1(HC) = 0, \sum_q^2 pa_q = 0.$$

Here, "pa" represents the phase encode factor (two phase encoding directions×one).

The correlation value of each functional connectivity was subjected to normalization by the least square regression by normal LS normalization, whereby each parameter was evaluated.

The site-to-site differences were removed by subtracting the evaluated site-to-site differences and the phase encode factor.

Therefore, the correlation value of the functional connectivity with the sampling bias harmonized is represented as:

$$\text{Connectivity}^{sampling} = \text{Connectivity} - x_m^T \hat{m} - x_{pa}^T \hat{pa}. \quad \text{[Equation 26]}$$

Here, "m" represents the evaluated measurement bias, and "pa" (hat) represents the evaluated phase encode factor.

Figure 45:
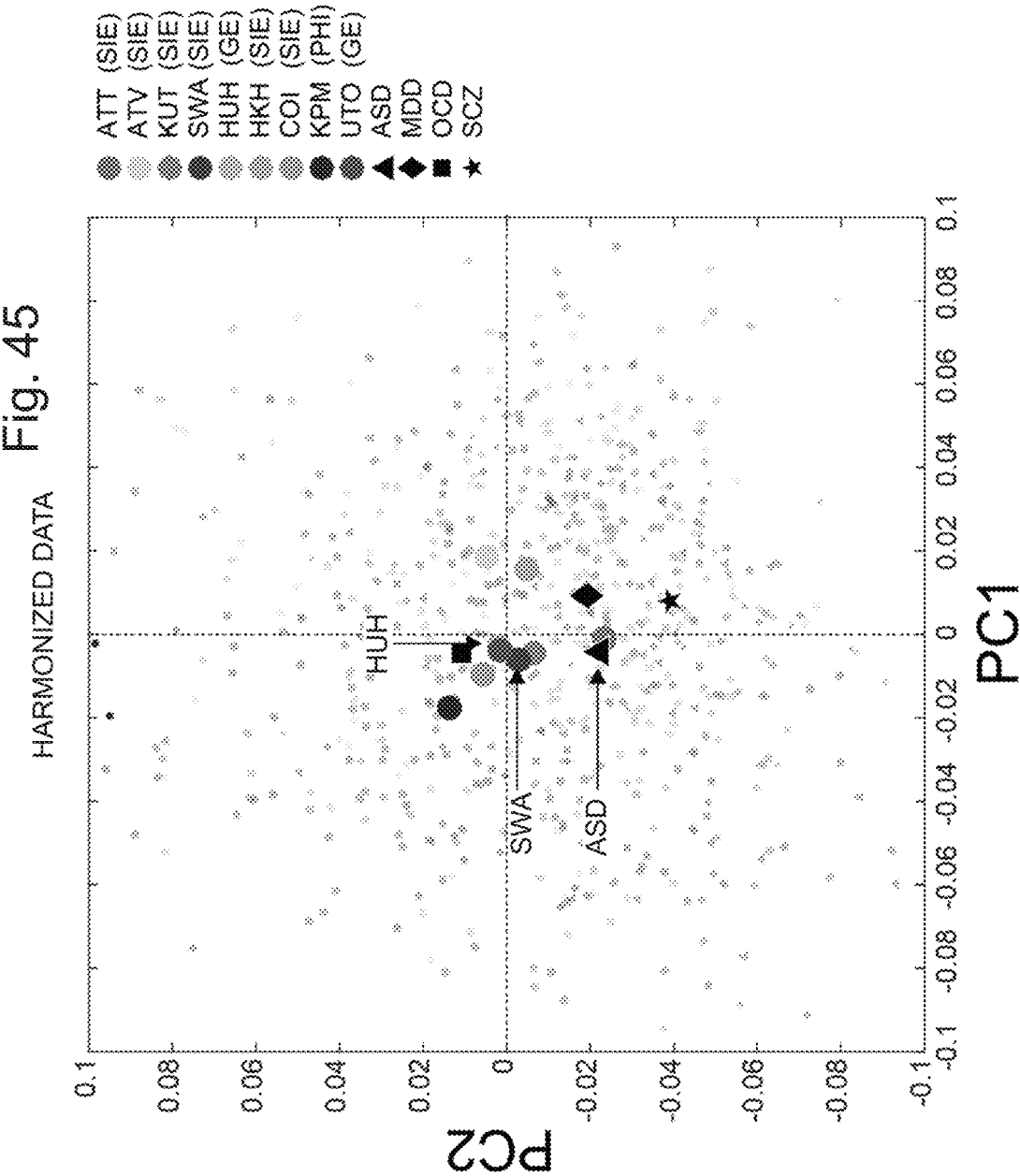
FIG. 45 visualizes the influence of the harmonization process, to be compared with FIG. 42.

FIG. 45 visualizes influence of the harmonization process, to be compared with FIG. 42.

In FIG. 45, from the SRPBS multi-disease dataset, only the measurement bias was removed, and thereafter, the data was plotted.

FIG. 42 reflects data before harmonization. When compared with FIG. 42, in FIG. 45, the HUH site is moved much closer to the origin (that is, to the average of population), and showed no marked separation from the other sites.

The results shown in FIG. 45 indicate that separation of HUH site such as shown in FIG. 42 was caused by the measurement bias, which could be removed by the harmonization.

Further, the harmonization was also effective to distinguish patients from healthy controls scanned at the same site.

Patients of ASD were scanned only at the SWA site and, therefore, the averages for ASD patients (A) and average of healthy people (o) were projected to nearly identical positions in FIG. 17.

These two symbols, however, are clearly separated from one another in FIG. 45.

Embodiment 2

In the configuration described in the first embodiment, the brain activity measuring devices (fMRI devices) measure data of brain activities obtained at a plurality of measuring sites, and based on the brain activity data, generation of biomarkers and estimation (prediction) of diagnosis labels by the biomarkers are realized by distributed processing.

It is noted, however, that the following process steps may be performed in a distributed manner at different sites: i) the measurement of brain activity data for training a biomarker through machine learning (data collection); ii) the process of generating a biomarker through machine learning and the process of estimating (predicting) diagnosis labels by the biomarker for a specific subject (estimation process); and iii) the measurement of brain activity data of the specific subject above (measurement of subject's brain activities).

Figure 46:
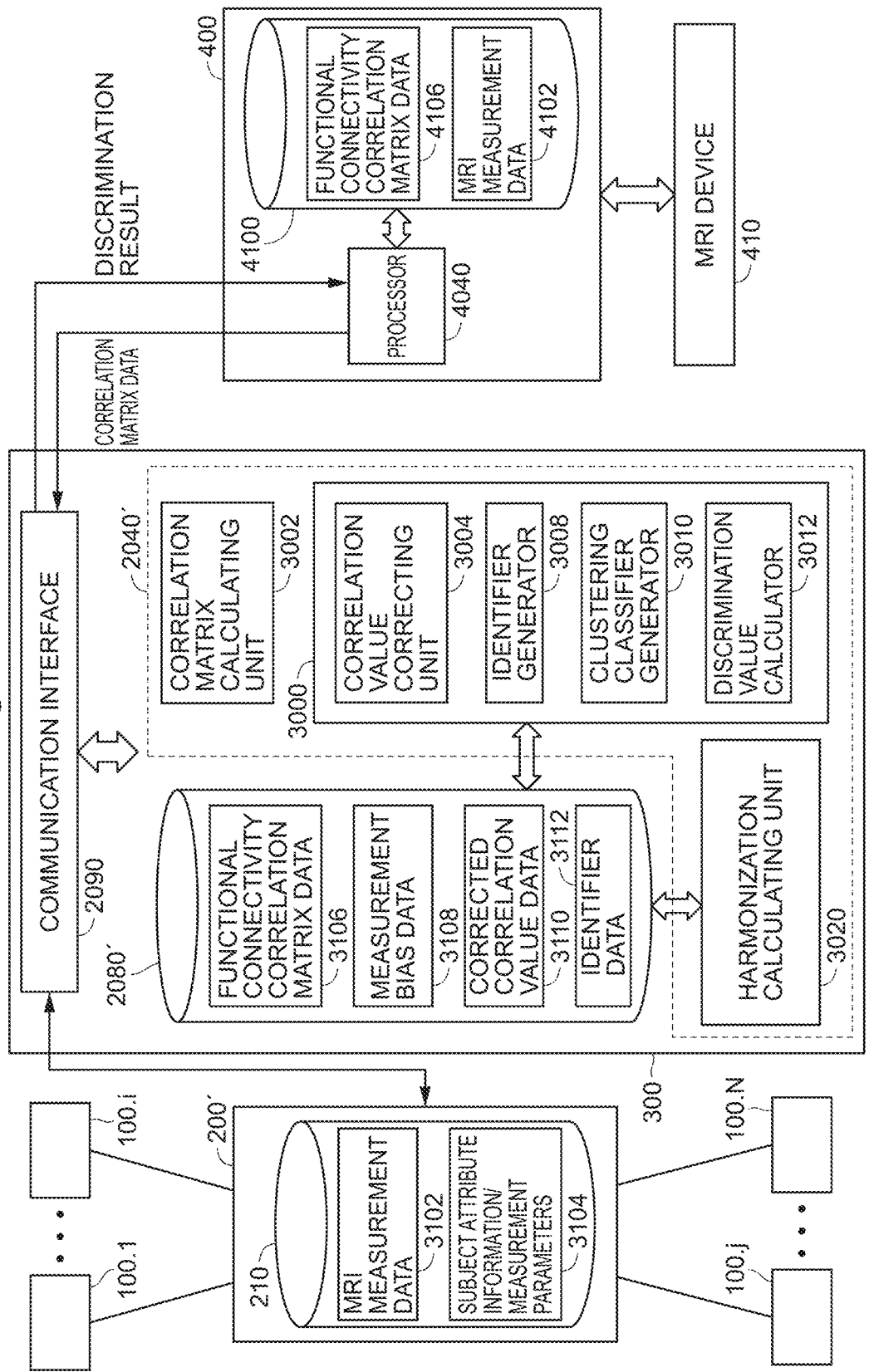
FIG. 46 is a functional block diagram showing an example when the data collection, the estimating process and the measurement of the brain activities of the subjects are processed in a distributed manner.

FIG. 46 is a functional block diagram showing an example when the data collection, the estimating process and the measurement of brain activities of subjects are processed in a distributed manner.

Referring to FIG. 46, sites 100.1 to 100.N represent facilities at which data of healthy cohort and patient cohort are measured by brain activity measuring devices, and a management server 200' manages measurement data from sites 100.1. to 100.$N_s$.

Computing system 300 generates a discriminator from the data stored in server 200.

Harmonization calculating unit 3020 of computing system 300 is assumed to perform the harmonization process including sites 100.1 to 100.$N_s$ and the site of MRI measuring device 410.

An MRI device 410 is provided at a separate site that utilizes the results from the identifier on computing system 300, and measures data of the brain activities of a specific subject.

A computer 400 is provided on a separate site where MRI device 410 is installed, and calculates the correlation data of the brain functional connectivity of the specific subject from the measurement data of MRI device 410, sends the correlation data of functional connectivity to computing system 300, and utilizes the results from the identifier that are sent back.

Data center 200 stores the MRI measurement data 3102 of patient cohort and healthy cohort transmitted from sites 100.1 to 100.$N_s$ as well as the human attribute information 3104 of the subject associated with the MRI measurement data 3102, and in accordance with an access from computing system 300, transmits these data to computing system 300.

Computing system 300 receives MRI measurement data 3102 and human attribute information 3104 of the subject from data center 200 through a communication interface 2090.

Hardware configurations of server 200, computing system 300 and computer 400 are basically the same as the configuration of "data processing unit 32" described with reference to FIG. 5 and, therefore, description thereof will not be repeated here.

Returning to FIG. 46, a correlation matrix calculating unit 3002, correlation value correcting unit 3004, disease identifier generator 3008, clustering classifier generator 3010 and discrimination value calculator 3012, as well as correlation matrix data 3106 of functional connectivity, measurement bias data 3108, corrected correlation value data 3110 and identifier data 3112 are the same as those described in the first embodiment and, therefore, description thereof will not be repeated here.

MRI device 410 measures the brain activity data of a subject whose diagnosis label is to be estimated, while processor 4040 of computer 400 stores the measured MRI measurement data 4102 in a non-volatile storage device 4100.

Further, a processor 4040 of computer 400 calculates functional connectivity correlation matrix data 4106 in the similar manner as correlation matrix calculating unit 3002, based on MRI measurement data 4102, and stores the calculated data in non-volatile storage device 4100.

A disease as an object of diagnosis is designated by a user of computer 400 and in accordance with an instruction of transmission by the user, computer 400 transmits the functional connectivity correlation matrix data 4106 to computing system 300. In response, computing system 300 performs the harmonization process corresponding to the site where the MRI device 410 is installed. Discrimination value calculator 3012 calculates the result of discrimination on the designated diagnosis label and evaluation result on subtypes, and computing system 300 transmits the results to computer 400 through communication interface 2090.

Computer 400 informs the user of the result of the discrimination using a display device or the like, not shown.

By such a configuration, it is possible to provide a larger number of users with the result of the estimation of the diagnosis label by the discriminator, based on the data collected from a larger number of users.

Further, data center 200 and computing system 300 may be managed by separate administrators. In that case, by limiting the computers that can access data center 200, it becomes possible to improve the security of subject information stored in data center 200.

Further, from the viewpoint of the operator of computing system 300, the "service of providing result of the discrimination" becomes possible while not providing any information at all of the identifier or information related to the "measurement biases" to the "side (computer 400) receiving the service of discrimination by the identifier."

In the descriptions of Embodiments 1 and 2 above, it is assumed that real-time fMRI is used as the brain activity detecting apparatus for time-sequentially measuring brain activities by functional brain imaging. It is noted, however, that any of the fMRI described above, a magnetoencephalography, a near-infrared spectroscopy (NIRS), an electroencephalography or any combination of these may be used as the brain activity detecting apparatus. Regarding such a combination, it is noted that fMRI and NIRS detect signals related to change in blood stream in the brain, and have a high spatial resolution. On the other hand, magnetoencephalography and electroencephalography are characterized in that they have a high temporal resolution, for detecting changes in an electromagnetic field associated with the brain activities. Therefore, if fMRI and the magnetoencephalography are combined, brain activities can be measured with both spatially and temporally high resolutions. Alternatively, by combining NIRS and the electroencephalography, a system for measuring the brain activities with both spatially and temporally high resolutions can also be implemented in a small, portable size.

By the configurations above, a brain activity analyzing apparatus and a brain activity analyzing method functioning as a biomarker using brain function imaging for neurological/mental disorders can be realized.

In the foregoing, an example has been described in which a "diagnosis label" is included as an attribute of a subject, and by generating an identifier through machine learning, the identifier is caused to function as a biomarker. The present invention, however, is not necessarily limited to such an example. Provided that a group of subjects whose results of measurements are to be obtained as the object of machine learning is classified into a plurality of classes in advance by an objective method, the correlation of degrees of activities (connection) among brain regions (regions of interest) of the subjects are measured and a discriminator can be generated for classification by machine learning using the measured results, the present invention may be used for other discrimination.

Further, as mentioned above, such a discrimination may indicate probability of the subject having a certain attribute.

Therefore, it is possible to objectively evaluate whether taking a certain "training" or following a certain "behavior pattern" is effective to improve the health of a subject or not. Further, it is also possible to objectively evaluate whether certain ingestions of "food" or "drink" or a certain activity or activities are effective to reach a healthier state before onset of a disease (in the state of "not yet diseased").

Further, even before the onset of a disease, if an indication such as "probability of being healthy: XX %" is output as mentioned above, it is possible to provide the user with an objective numerical value of his/her state of health. Here, the output may not necessarily be the probability. For example, "a continuous value of degree of healthiness, such as probability of being healthy" converted to a score may be displayed. By providing such a display, the apparatus in accordance with the embodiments of the present invention can be used as an apparatus for health management of users.

Embodiment 3

In the foregoing description, it is assumed that the traveling subjects travel to every measurement site and have measurements equally, and thereby measurement biases are evaluated.

Figure 47:
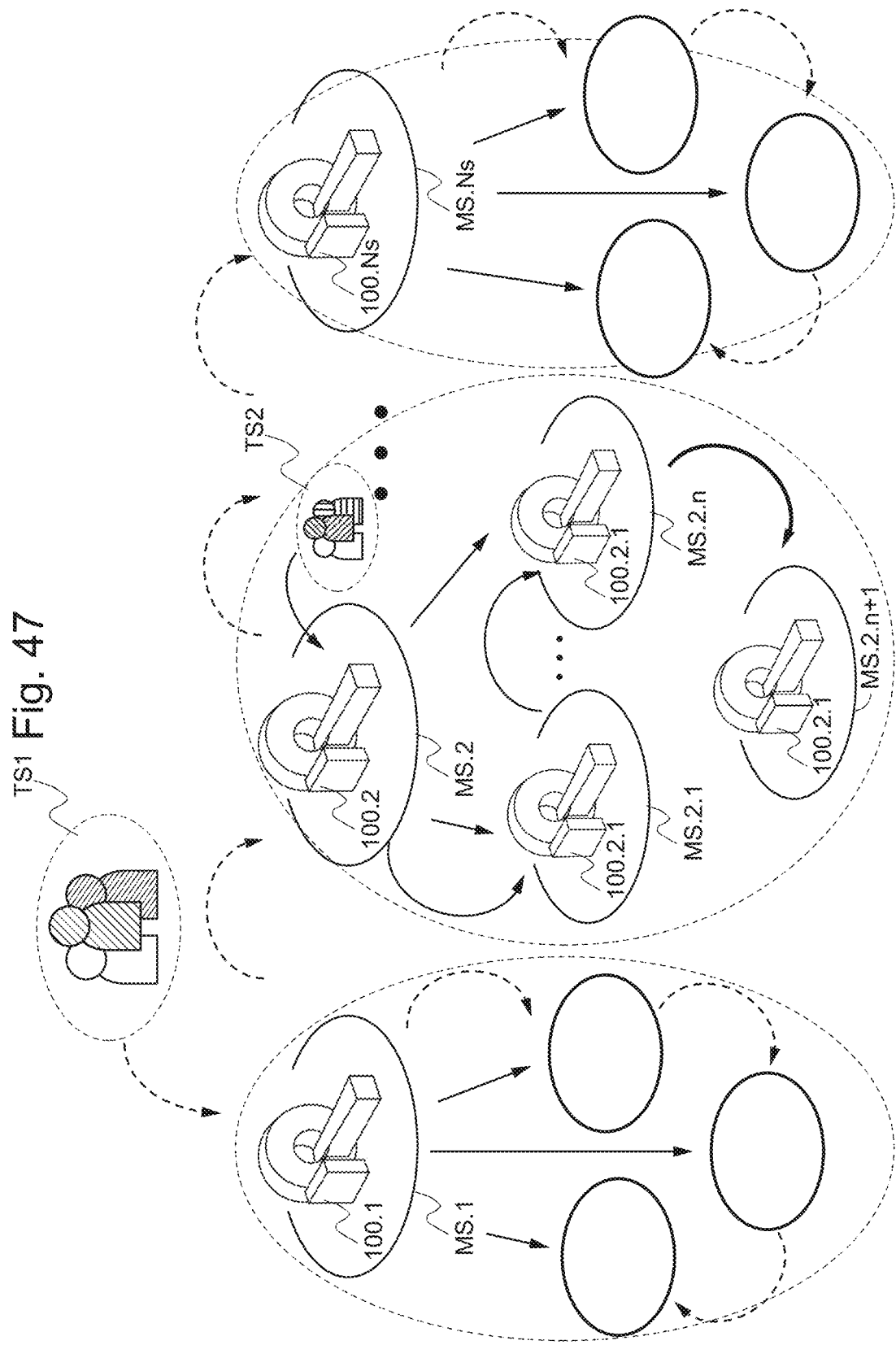
FIG. 47 shows the routing of the traveling subjects.

FIG. 47 shows a circuiting scheme of the traveling subjects in accordance with Embodiment 3.

As shown in FIG. 47, it is assumed that the traveling subject TS1 makes the rounds of the "hub measurement sites MS.1 to MS.$N_s$" serving as lodgments.

In this regard, among these hub measurement sites MS.1 to MS.$N_s$, it is assumed that there are subordinate sites MS2.1 to MS2.$n$ under the hub measurement site MS.2. If a new measurement site "MS.2.$n$+1" is added to the sites under hub measurement site MS.2, a traveling subject TS2 makes the rounds of the sites under the hub measurement site MS.2. The same applies to other hub measurement sites.

Specifically, a configuration is also possible wherein the measurement biases of hub measurement site MS.2 are fixed to the values evaluated concerning the traveling subject TS1 and the measurement biases of the measurement sites MS.2, MS.2.1, MS.2.$n$ and MS2.$n$+1 may be determined based on the measurement results of the traveling subject TS2 making the rounds of these sites.

By way of example, the "hub measurement sites MS.1 to MS.$N_s$" may exist at predetermined regions. For instance, one hub may be located in each of such areas as Hokkaido, Tohoku, Kanto, Kansai, . . . , and Kyushu areas in Japan, and the subordinate sites may be located in one of these areas, for example, in the Kansai area.

Alternatively, the "hub measurement sites MS.1 to MS.$N_s$" may be selected for each of the predetermined types of MRI devices. In that case, the subordinate measurement sites will be the measurement sites where the same type of the MRI device as the hub site is installed.

Alternatively, the "hub measurement sites MS.1 to MS.$N_s$" may be selected for area by predetermined area and type by the predetermined type of MRI devices. In that case, the limb measurement sites are the measurement sites located in the same area as the hub site and having the same MRI device as the hub installed.

By such configurations also, the same effects as in the first embodiment can be attained.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

REFERENCE SIGNS LIST 2 subject, 6 display, 10 MRI device, 11 magnetic field applying mechanism, 12 static magnetic field generating coil, 14 magnetic field gradient generating coil, 16 RF irradiating unit, 18 bed, 20 receiving coil, 21 driving unit, 22 static magnetic field power source, 24 magnetic field gradient power source, 26 signal transmitting unit, 28 signal receiving unit, 30 bed driving unit, 32 data processing unit, 36 storage unit, 38 display unit, 40 input unit, 42 control unit, 44 interface unit, 46 data collecting unit, 48 image processing unit, 50 network interface

The invention claimed is:

1. A clustering device for clustering brain functional connectivity correlation values performing, based on measurement results of brain activities of objects, clustering of objects having at least one prescribed attribute among said objects, comprising
 a computing system for performing a process of said clustering based on measured values of brain activities, on a plurality of subjects including a first cohort of subjects having said prescribed attribute and a second cohort of subjects not having said prescribed attribute, said computing system including a storage device and a processor; wherein
 said processor is configured to perform the steps of
 i) storing, in said storage device, for each of said plurality of subjects, features based on a plurality of brain functional connectivity correlation values respectively representing time-wise correlation of brain activities between each of a prescribed plurality of pairs of brain regions, and
 ii) based on said features stored in said storage device, conducting supervised machine learning for generating an identifier model for discriminating presence/absence of said attribute;
 said processor performs, in the machine learning for generating an identifier model, the steps of
 generating a plurality of training sub-samples by performing under-sampling and sub-sampling from said first cohort of subjects and said second cohort of subjects, and
 selecting, for each of said training sub-samples, from a sum set of features used for generating the identifier by machine learning, features for clustering in accordance with importance of features belonging to said sum set; and
 said processor further performs the step of clustering said first cohort of subjects through multiple co-clustering of unsupervised learning, based on the selected features for clustering, and thereby generates a cluster classifier.

2. The clustering device for clustering brain functional connectivity correlation values according to claim 1, receiving, from a plurality of brain activity measuring devices provided respectively at a plurality of measurement sites, information representing time-wise correlation of brain activities between each of a prescribed plurality of pairs of brain regions of each of a plurality of subjects; wherein
 said computing system includes
 a harmonization calculating means for correcting said plurality of brain functional connectivity correlation values of each of said plurality of subjects to remove measurement bias of said measurement sites and thereby storing corrected adjusted values as said features in said storage device.

3. The clustering device for clustering brain functional connectivity correlation values according to claim 1, wherein
 the process of generating an identifier by the machine learning involves ensemble learning of generating a plurality of identifier sub-models respectively for said plurality of training samples, and integrating said plurality of identifier sub-models to generate said identifier model.

4. The clustering device for clustering brain functional connectivity correlation values according to claim 1, wherein
 said attribute is represented by a label of diagnosis result as having a prescribed psychiatric disorder; and
 said clustering is a process of classifying, by data-driven machine learning, said first cohort of subjects into clusters of at least one subtype.

5. The clustering device for clustering brain functional connectivity correlation values according to claim 1, wherein
 in generating an identifier by said machine learning, said processor performs the steps of
 i) dividing said adjusted values into a training dataset for machine learning and a test dataset for validation;
 ii) performing under-sampling and sub-sampling a prescribed number of times on said training dataset to generate said prescribed number of training sub-samples;
 iii) generating an identifier sub-model for each of said training sub-samples; and
 iv) integrating outputs of said identifier sub-models and generating an identifier model regarding presence/absence of said attribute.

6. The clustering device for clustering brain functional connectivity correlation values according to claim 1, wherein
 the process of generating an identifier by said machine learning is nested cross-validation having external cross-validation and internal cross-validation;
 in said nested cross-validation, said processor performs the steps of:
 i) dividing said adjusted values into a training dataset for machine learning and a test dataset for validation by conducting K-fold cross-validation as said external cross-validation;
 ii) performing under-sampling and sub-sampling a prescribed number of times on said training dataset to generate said prescribed number of training sub-samples;
 iii) in each loop of said K-fold cross-validation, adjusting hyper-parameters by said internal cross-validation and thereby generating an identifier sub-model for each of said training sub-samples; and
 iv) generating an identifier model regarding presence/absence of said attribute based on said identifier sub-models.

7. The clustering device for clustering brain functional connectivity correlation values according to claim 3, wherein
the process of generating an identifier by said machine learning is machine learning with feature selection; and
in selecting a feature for the clustering, importance of a feature belonging to said sum set is determined by a ranking of frequency of said feature being selected when said identifier sub-model is selected.

8. The clustering device for clustering brain functional connectivity correlation values according to claim 3, wherein
the process of generating an identifier by said machine learning is a random forest method; and
in selecting a feature for the clustering, importance of a feature belonging to said sum set is an importance calculated in accordance with Gini impurity in the random forest method for each feature.

9. The clustering device for clustering brain functional connectivity correlation values according to claim 3, wherein
the process of generating an identifier by said machine learning is machine learning by L2 regularization; and
in selecting a feature for the clustering, importance of a feature belonging to said sum set is determined by a ranking based on feature weight in said identifier sub-model calculated by L2 regularization.

10. The clustering device for clustering brain functional connectivity correlation values according to claim 2, wherein:
said storage device stores in advance, for a plurality of traveling subjects as common objects of measurements across said plurality of measurement sites, results of measurements of brain activities of a predetermined plurality of brain regions of each of said traveling subjects;
said processor performs the steps of
for each of said traveling subjects, calculating a prescribed component of a brain functional connectivity matrix representing time-wise correlation of brain activities of said plurality of pairs of brain regions; and
by using Generalized Linear Mixed Model, for each prescribed component of said functional connectivity matrix, calculating said measurement bias as a fixed effect at each measurement site with respect to an average of the component over said plurality of measurement sites and said plurality of traveling subjects.

11. The clustering device for clustering brain functional connectivity correlation values according to claim 4, wherein said processor performs said process of classifying into said subtypes based on measurement data of a subject measured at a measurement site other than said plurality of measurement sites.

12. A clustering system for clustering brain functional connectivity correlation values performing, based on measurement results of brain activities of objects, clustering of objects having at least one prescribed attribute among said objects, comprising
a plurality of brain activity measuring devices provided respectively at a plurality of measurement sites, for time-sequentially measuring brain activities of a plurality of subjects including a first cohort of subjects having said prescribed attribute and a second cohort of subjects not having said prescribed attribute, and
a computing system for performing a process of said clustering based on measured values of brain activities, on said plurality of subjects, said computing system including a storage device and a processor; wherein
said processor is configured to perform the steps of
i) storing, in said storage device, for each of said plurality of subjects, features based on a plurality of brain functional connectivity correlation values respectively representing time-wise correlation of brain activities between each of a prescribed plurality of pairs of brain regions, and
ii) based on said features stored in said storage device, conducting supervised machine learning for generating an identifier model for discriminating presence/absence of said attribute;
said processor performs, in the machine learning for generating an identifier model, the steps of
generating a plurality of training sub-samples by performing under-sampling and sub-sampling from said first cohort of subjects and said second cohort of subjects, and
selecting, for each of said training sub-samples, from a sum set of features used for generating the identifier by machine learning, features for clustering in accordance with importance of features belonging to said sum set; and
said processor further performs the step of clustering said first cohort of subjects through multiple co-clustering of unsupervised learning, based on the selected features for clustering, and thereby generating a cluster classifier.

13. The clustering system for clustering brain functional connectivity correlation values according to claim 12, wherein said computing system receives, from a plurality of brain activity measuring devices provided respectively at a plurality of measurement sites, information representing time-wise correlation of brain activities between each of a prescribed plurality of pairs of brain regions of each of said plurality of subjects; and includes
a harmonization calculating means for correcting said plurality of brain functional connectivity correlation values of each of said plurality of subjects to remove measurement bias of said measurement sites and thereby storing corrected adjusted values as said features in said storage device.

14. The clustering system for clustering brain functional connectivity correlation values according to claim 12, wherein
said attribute is represented by a label of diagnosis result as having a prescribed psychiatric disorder; and
said clustering is a process of classifying, by data-driven machine learning, said first cohort of subjects into clusters of at least one subtype.

15. A clustering method of clustering brain functional connectivity correlation values allowing a computing system to perform, based on measurement results of brain activities of objects, clustering of objects having at least one prescribed attribute among said objects, wherein
said computing system includes a storage device and a processor,
said method comprising the steps of:
said processor storing, in said storage device, for each of said plurality of subjects including a first cohort of subjects having said prescribed attribute and a second cohort of subjects not having said prescribed attribute, features based on brain functional connectivity correlation values representing time-wise correlation of brain activities between each of a prescribed plurality of pairs of brain regions, and based on said features stored in said storage device, said processor conducting supervised machine learning for generating an identifier model for discriminating presence/absence of said attribute; wherein said step of machine learning for generating an identifier model includes the steps of:

generating a plurality of training sub-samples by performing under-sampling and sub-sampling from said first cohort of subjects and said second cohort of subjects, and selecting, for each of said training sub-samples, from a sum set of features used for generating the identifier by machine learning, features for clustering in accordance with importance of features belonging to said sum set;

said method further comprising the step of:

said processor clustering said first cohort of subjects through multiple co-clustering of unsupervised learning, based on the selected features for clustering, and thereby generating a cluster classifier.

16. A brain function marker classifying system, generated by a computing system performing, based on measurement results of brain activities of objects, clustering of objects having at least one prescribed attribute among said objects, allowing a computer to perform classifying of input data into clusters corresponding to the result of clustering, wherein said brain activity marker classifying system has a classifying function allowing the computer to classify into a cluster in which said input data has maximum posterior probability, based on a probability distribution model of each of said clusters;

said computing system includes a storage device and a processor; and in the process of generating said brain activity marker classifying system based on said clustering, said computing system performs the steps of:

said processor storing, in said storage device, for each of a plurality of subjects including a first cohort of subjects having said prescribed attribute and a second cohort of subjects not having said prescribed attribute, features based on a plurality of brain functional connectivity correlation values representing time-wise correlation of brain activities between each of a prescribed plurality of pairs of brain regions, and based on said features stored in said storage device, said processor conducting supervised machine learning for generating an identifier model for discriminating presence/absence of said attribute; wherein said step of machine learning for generating an identifier model includes the steps of:

generating a plurality of training sub-samples by performing under-sampling and sub-sampling from said first cohort of subjects and said second cohort of subjects, and selecting, for each of said training sub-samples, from a sum set of features used for generating the identifier by machine learning, features for clustering in accordance with importance of features belonging to said sum set; and wherein said processor performs clustering of said first cohort of subjects through multiple co-clustering of unsupervised learning, based on the selected features for clustering, and thereby generates a cluster classifier.

17. The brain function marker classifying system according to claim 16, wherein said computing system performs the steps of:

receiving, from a plurality of brain activity measuring devices provided respectively at a plurality of measurement sites, information representing time-wise correlation of brain activities between each of a prescribed plurality of pairs of brain regions of each of said plurality of subjects; and conducting harmonization for correcting a plurality of brain functional connectivity correlation values representing time-wise correlation of said brain activities of each of said plurality of subjects to remove measurement bias of said measurement sites and thereby storing corrected adjusted values as said features in said storage device.

18. The brain function marker classifying system according to claim 16, wherein said attribute is represented by a label of diagnosis result as having a prescribed psychiatric disorder; and said clustering is a process of classifying, by data-driven machine learning, said first cohort of subjects into clusters of at least one subtype.

19. A clustering classifier model for clustering brain functional connectivity correlation values generated by a computing system performing, based on measurement results of brain activities of objects, clustering of objects having at least one prescribed attribute among said objects, allowing a computer to perform classifying of input data into clusters corresponding to the result of clustering, wherein for each of views obtained by partitioning a group of features characterizing said object included in training data, said clustering classifier model has a function of classifying said input data into a cluster in which said input data has maximum posterior probability, in accordance with a value of probability density function calculated for said input data, based on information of said features included in each of said views and based on information specifying cluster-by-cluster probability density function of said object in each of said views;

said computing system includes a storage device and a processor; and in the process of generating said clustering classifier model based on said clustering, said computing system performs the steps of:

said processor storing, in said storage device, for each of a plurality of subjects including a first cohort of subjects having said prescribed attribute and a second cohort of subjects not having said prescribed attribute, features based on a plurality of brain functional connectivity correlation values representing time-wise correlation of brain activities between each of a prescribed plurality of pairs of brain regions, and based on said features stored in said storage device, said processor conducting supervised machine learning for generating an identifier model for discriminating presence/absence of said attribute; wherein said step of machine learning for generating an identifier model includes the steps of:

generating a plurality of training sub-samples by performing under-sampling and sub-sampling from said first cohort of subjects and said second cohort of subjects, and selecting, for each of said training sub-samples, from a sum set of features used for generating the identifier by machine learning, features for clustering in accordance with importance of features belonging to said sum set; and wherein said processor performs clustering of said first cohort of subjects through multiple co-clustering of unsupervised learning, based on the selected features for clustering, partitions said features to said views, and generates the cluster-by-cluster probability density function of said object in each of said views.

\* \* \* \* \*